United States Patent
Shao et al.

(10) Patent No.: US 12,163,960 B2
(45) Date of Patent: Dec. 10, 2024

(54) COMPOSITIONS AND METHODS FOR PREDICTING THERAPEUTIC OUTCOME

(71) Applicant: Washington University, St. Louis, MO (US)

(72) Inventors: Jieya Shao, St. Louis, MO (US); Marc Diamond, St. Louis, MO (US)

(73) Assignee: Washington University, St. Louis, MO (US)

( * ) Notice: Subject to any disclaimer, the term of this patent is extended or adjusted under 35 U.S.C. 154(b) by 670 days.

(21) Appl. No.: 17/315,061

(22) Filed: May 7, 2021

(65) Prior Publication Data

US 2021/0349100 A1 Nov. 11, 2021

Related U.S. Application Data

(60) Provisional application No. 63/021,333, filed on May 7, 2020.

(51) Int. Cl.
| | | |
|---|---|---|
| G01N 33/574 | (2006.01) | |
| C07K 16/40 | (2006.01) | |
| G01N 33/50 | (2006.01) | |

(52) U.S. Cl.
CPC ....... G01N 33/57496 (2013.01); C07K 16/40 (2013.01); C12Y 306/04006 (2013.01); G01N 33/5088 (2013.01); *C07K 2317/565* (2013.01); *G01N 2333/914* (2013.01); *G01N 2440/14* (2013.01)

(58) Field of Classification Search
CPC ......... G01N 33/57496; G01N 2440/14; C07K 2317/565
See application file for complete search history.

(56) References Cited

PUBLICATIONS

Almagro JC, Fransson J. Humanization of antibodies. Front Biosci. Jan. 1, 2008;13:1619-33. (Year: 2008).*
Chen et al., Enhancement and destruction of antibody function by somatic mutation: unequal occurrence is controlled by V gene combinatorial associations. EMBO J. Jun. 15, 1995;14(12):2784-94. (Year: 1995).*
Edwards et al. The remarkable flexibility of the human antibody repertoire; isolation of over one thousand different antibodies to a single protein, BLyS. J Mol Biol Nov. 14, 2003;334(1):103-18. (Year: 2003).*
Koenig et al. Mutational landscape of antibody variable domains reveals a switch modulating the interdomain conformational dynamics and antigen binding. PNAS Jan. 24, 2017 114(4)E486-E495;firstpublished Jan. 5, 2017. (Year: 2017).*
Kussie et al. A single engineered amino acid substitution changes antibody fine specificity.J Immunol. Jan. 1, 1994;152(1): 146-52. (Year: 1994).*
Ausubel F.M., et al., "Short Protocols in Molecular Biology," A Compendium of Methods from Current Protocols in Molecular Biology, 5th Edition, Wiley, vol. 1, 2002, ISBN-10: 0471250929, 692 pages.
Baneyx F., "Protein Expression Technologies," Current Status and Future Trends, Taylor Francis, 2004, ISBN-10: 0954523253, 552 pages.
Brandsma I., et al., "Directing the Use of DDR Kinase Inhibitors in Cancer Treatment," Expert Opinion on Investigational Drugs, 2017, vol. 26, No. 12, 33 pages.
Clackson T., et al., "Making Antibody Fragments using Phage Display Libraries," Nature, Aug. 15, 1991, vol. 352, pp. 624-628.
D. B. Budman, A. H. Calvert, E. K. Rowinsky (editors), "Handbook of Anticancer Drug Development," LWWWV, 2003.
Durant S.T., et al., "The Brain-Penetrant Clinical ATM Inhibitor AZD1390 Radiosensitizes and Improves Survival of Preclinical Brain Tumor Models," Science Advances, Jun. 20, 2018, vol. 4:eaat1719, pp. 1-16.
Elhai J., et al., "Conjugal Transfer of DNAto Cyanobacteria," Methods in Enzymology, Academic Press, Inc, 1988, vol. 167, pp. 747-754.
Gellissen G., "Production of Recombinant Proteins: Novel Microbial and Eukaryotic Expression Systems," Wiley-VCH, Edition 2005, ISBN-10: 3527310363, 419 pages.
Kabat E.A., et al., "Sequences of Proteins of Immunological Interest," US Department of Health and Human Services, Public Health Service, National Institutes of Health, 5th Edition, 1991, vol. 1, 1247 pages.
Kindt T.J., et al., "Kuby Immunology," W.H. Freeman and Company, 6th Edition, 2007, 706 pages.
Koda-Kimble et al., "Applied Therapeutics: The Clinical Use of Drugs," Lippincott Williams Wilkins, 2004, ISBN 0781748453.
Lefranc M-P., "Definition of the FR-IMGT and CDR-IMGT Regions," IMGT Scientific Chart available online at: https://www.imgt.org/IMGTScientificChart/Nomenclature/IMGT-FRCDRdefinition.html, Mar. 25, 1997, 2 pages.
Lefranc M-P., et al., "IMGT, the International ImMunoGeneTics Information System," Nucleic Acids Research, 2009, vol. 37, pp. D1006-D1012, Database issue.
Lefranc M-P., "The IMGT Unique Numbering for Immunoglobulins, T-Cell Receptors, and Ig-Like Domains," The Immunologist, 1999, vol. 7, No. 4, pp. 132-136.
Maccallum R.M., et al., "Antibody-Antigen Interactions: Contact Analysis and Binding Site Topography," Journal of Molecular Biology, Oct. 11, 1996, vol. 262, No. 5, pp. 732-745.
Matsuoka S., et al., "ATM and ATR Substrate Analysis Reveals Extensive Protein Networks Responsive to DNA Damage" Science, May 25, 2007, vol. 316, pp. 1160-1166.
Portolano S., et al., "Lack of Promiscuity in Autoantigen-Specific H and L Chain Combinations as Revealed by Human H and L Chain "Routlette"," Journal of Immunology, Feb. 1, 1993, vol. 150, No. 3, pp. 880-887.

(Continued)

*Primary Examiner* — Aurora M Fontainhas
*Assistant Examiner* — Jennifer A Benavides
(74) *Attorney, Agent, or Firm* — Polsinelli PC

(57) ABSTRACT

The present disclosure provides methods to quantify VCP phosphorylation at specific amino acid residue to predict responsiveness of a subject having a cancer or tumor to a genotoxic treatment, guide treatment decisions, select subjects for clinical trials, and evaluate the clinical efficacy of certain therapeutic interventions.

6 Claims, 57 Drawing Sheets
(40 of 57 Drawing Sheet(s) Filed in Color)
Specification includes a Sequence Listing.

(56) References Cited

PUBLICATIONS

Sambrook and Russel, "Molecular Cloning: A Laboratory Manual," 3rd ed., Cold Spring Harbor Laboratory Press, 2001, ISBN-10: 0879695773.

Stokes M.P., et al., "Profiling of UV-Induced ATM/ATR Signaling Pathways," Proceedings of the National Academy of Sciences, Dec. 11, 2007, vol. 104, No. 50, pp. 19855-19860.

Studier F.W., "Protein Production by Auto-Induction in High-Density Shaking Cultures," Protein Expression and Purification, May 2005, vol. 41, No. 1, pp. 207-234.

Weber A.M., et al., "ATM and ATR as Therapeutic Targets in Cancer," Pharmacology Therapeutics, 2015, vol. 149, pp. 124-138.

Winter M.E., "Basic Clinical Pharmacokinetics," 4th Edition, Lippincott Williams Wilkins, 2003, ISBN 0781741475, 532 pages.

* cited by examiner

IB: pSer$^{137}$-Pfn1 ab

IP: pSer$^{137}$-Pfn1 ab
IB: VCP

SPECS Series (Nuclear Allred)

… (1)

COMPOSITIONS AND METHODS FOR PREDICTING THERAPEUTIC OUTCOME

CROSS REFERENCE TO RELATED APPLICATION

This application claims the benefit of U.S. Provisional Application No. 63/021,333, filed May 7, 2020, the disclosure of which is herein incorporated by reference in its entirety.

GOVERNMENTAL RIGHTS

This invention was made with government support under CA131226 and NS050284 awarded by the National Institutes of Health. The government has certain rights in the invention.

FIELD OF THE TECHNOLOGY

The present disclosure relates, in general, to compositions and methods for predicting outcome of cancer therapeutics. More specifically, the present disclosure provides compositions and methods to quantify valosin-containing protein (VCP) phosphorylation at $Ser^{784}$ to guide treatment decisions, evaluate the clinical efficacy of certain therapeutic interventions, and select subjects for clinical trials.

REFERENCE TO SEQUENCE LISTING

This application contains a Sequence Listing that has been submitted in ASCII format via EFS-Web and is hereby incorporated by reference in its entirety. The ASCII copy, created on May 6, 2021, is named 687885-ST25.txt, and is 13,288 bytes in size.

BACKGROUND

Genotoxic stress, including oxidative stress, causes DNA damage. The evolutionary conservative cellular mechanisms of DNA-damage prevention and response (DNA repair, defense against reactive oxygen species, cell cycle checkpoints, and apoptosis) protect cells from mutations and tissues from acquiring malignancy. On the one hand, genotoxic stress can induce carcinogenesis, on the other hand, it is used to treat cancer. Resistance to genotoxic cancer therapies can result in more frequent relapse poor outcome in cancer subjects. There is a need for improved compositions and methods useful to determine responsiveness to genotoxic cancer therapies.

BRIEF DESCRIPTION OF THE FIGURES

Those of skill in the art will understand that the drawings, described below, are for illustrative purposes only. The drawings are not intended to limit the scope of the present teachings in any way.

The application file contains at least one drawing executed in color. Copies of this patent application publication with color drawing(s) will be provided by the Office upon request and payment of the necessary fee.

FIG. 2A shows representative images of the nuclear staining of human breast tumors by the $pSer^{137}$-Pfn1 antibody. 20× magnification; scale bars, 100 μm. FIG. 2B shows univariate Kaplan-Meier analyses showing an inverse correlation between nuclear staining by the $pSer^{137}$-Pfn1 antibody and patient survival in the SPECS series. FIG. 2C shows univariate Kaplan-Meier analyses showing an inverse correlation between nuclear staining by the pSer137-Pfn1 antibody and patient survival in the UBC series. FIG. 2D depicts univariate Kaplan-Meier analyses showing an inverse correlation between nuclear staining by the pSer137-Pfn1 antibody and patient survival in the TNBC subset of the UBC series. OS, overall survival; RFS, relapse-free survival; BCSS, breast cancer-specific survival; TNBC, triple-negative breast cancer. FIG. 2E shows univariate Kaplan-Meier analysis of the BCCancer series showing the associations between nuclear staining by the $pSer^{137}$-Pfn1 antibody and poor survival outcome (BCSS) of the chemotherapy-treated breast cancer patients. Log-rank and Wilcoxon tests were used. $p<0.05$ was considered statistically significant. Unadjusted p values for the outcome in the chemotherapy-treated group of BCCancer series are displayed.

FIG. 3A shows representative IHC images of cytoplasmic staining of breast tumors by the $pSer^{137}$-Pfn1 antibody. FIG. 3B shows individual nuclear Allred scores of the UBC TMA series were used for Kaplan-Meier analysis for association with the overall (OS) and relapse-free survival (RFS). FIG. 3C shows Nuclear Allred scores from (B) were binarized into low vs. high groups and subjected to Kaplan-Meier analysis for association with RFS as in (B). FIG. 3D shows samples in the UBC series were divided into estrogen receptor negative (ER negative) vs. positive (ER positive) subgroups and subjected to the same survival analysis as in (C) using the binarized nuclear Allred scores. FIG. 3E shows Cytoplasmic staining of the UBC TMA by the pSer137-Pfn1 antibody was scored based on the percentage of positive cells (intensity was similar across tissues) into four groups (0-10%, 11-33%, 34-66%, 67-100%). The scores were used in univariate Kaplan-Meier analysis for association with overall (OS), relapse-free (RFS), and breast cancer-specific survival (BCSS). Log-rank and Wilcoxon tests were used to generate the p values which were considered statistically significant when being less than 0.05. Scale bars, 10 μm.

FIG. 4A shows binarized nuclear Allred scores as described in FIG. 3C-3D were subjected to univariate Kaplan-Meier analysis for association with overall survival. FIG. 4B shows binarized nuclear Allred scores as described in FIG. 3C-3D were subjected to univariate Kaplan-Meier analysis for association with breast cancer-specific survival. FIG. 4C shows binarized nuclear Allred scores as described in FIG. 3C-3D were subjected to univariate Kaplan-Meier analysis for association with relapse-free survival. Log-rank and Wilcoxon tests were used to generate the p values which were considered statistically significant when being less than 0.05. Unadjusted P values for the outcome in the different IHC subtypes are displayed.

FIG. 5A show binarized nuclear Allred scores (low vs. high) were used in the univariate Kaplan-Meier analysis of the BCCancer cohort for breast cancer-specific survival (BCSS), shown for the training (n=1311) and validation (n=1340) sets separately. FIG. 5B show the training set of the BCCancer series (n=1311) was divided into subgroups based on systematic adjuvant treatments and subjected to univariate Kaplan-Meier analysis for BCSS. Shown here are the no treatment (n=562), tamoxifen (n=407) and chemotherapy plus tamoxifen (n=100) groups. No validation for these treatment groups was performed due to the lack of statistically significant association between nuclear scores and survival. FIG. 5C show chemotherapy-treated cases within the whole BCCancer series (n=672) were divided into triple negative vs. non-triple negative subgroups and subjected to the same Kaplan-Meier analysis for the association between binarized nuclear Allred scores and BCSS. Training, validation, and combined datasets are shown. Log-rank and Wilcoxon tests were used to generate the p values which were considered statistically significant when being less than 0.05. Unadjusted P values for the outcome in the different treatment groups of BCCancer series are displayed.

FIG. 6A shows Hela cells were treated with DMSO, 200 nM of SN38, and 5 μM of etoposide for 6 h, followed by staining using the pSer$^{137}$-Pfn1 antibody. DAPI was used to stain DNA. FIG. 6B shows Hela cells were treated with DMSO, 200 nM of SN38, and 1 μM of gemcitabine for 16 h, followed by western blot analysis using the pSer137-Pfn1 antibody. Red arrowhead indicates the DNA-damage-induced ~100-kDa protein. FIG. 6C shows nuclear extracts of DMSO- or SN38-treated (200 nM, 16 h) Hela cells were immunoprecipitated by the pSer137-Pfn1 antibody, followed by SDS-PAGE analysis and silver staining. The drug-induced protein at ~100 kDa was excised and identified as VCP by mass spectrometry. FIG. 6D shows Pull-down samples from (C) were analyzed by western blot using a VCP-specific antibody. FIG. 6E shows Hela cells were infected with shLuc or two distinct shVCPs for 3 days, treated with 5 μM of etoposide for 6 h, and immunostained using the pSer$^{137}$-Pfn1 antibody. FIG. 6F shows HeLa cells were treated with 5 μM of etoposide for 6 h, extracted by the CSK buffer for 5 min, and stained by the pSer$^{137}$-Pfn1 antibody. FIG. 6G shows HEK293T cells were transfected with wild-type or mutant VCP-GFP, treated with 200 nM of SN38 for 16 hr, and immunoprecipitated using the pSer$^{137}$-Pfn1 antibody. Pull-down and input samples were analyzed by western blot using a GFP antibody. FIG. 6H shows input samples from (A) were analyzed by western blot using the pSer$^{137}$-Pfn1 or VCP antibodies. FIG. 6I shows Hela cells were pre-treated for 30 min with DMSO, 10 mM of caffeine, or 10 μM of KU-55933, followed by 30 min of treatment with 50 μM of etoposide. They were lysed by RIPA (without SDS), and the soluble and insoluble fractions were analyzed by western blot. pSer$^{784}$-VCP was detected by the pSer$^{137}$-Pfn1 antibody. All data, except (C), were independently confirmed two to three times. Scale bars, 20 μm (A) and (E) and 10 μm (F).

FIG. 7A shows different breast cancer cell lines were treated with DMSO or etoposide (5 μM) for 6 hr, followed by immunofluorescence staining using the pSer$^{137}$-Pfn1 antibody. FIG. 7B shows Hela cells were treated with various genotoxic agents (1 mM HU, 1 μM cisplatin, 1 μM gemcitabine, 50 μM 5-fluorouracil) for 16 hr, followed by immunofluorescence staining using the pSer137-Pfn1 antibody and counterstaining by DAPI. Scale bars, 20 μm. FIG. 7C shows Hela cells were infected with a control shRNA or two shRNAs targeting human Pfn1. Western blot showing complete Pfn1 knockdown 4 days after infection. FIG. 7D shows Hela cells infected with two control shRNAs (shCtrl and shLacZ) and the two Pfn1-specific shRNAs were treated with 5 μM etoposide for 6 h, followed by immunofluorescence staining using the pSer$^{137}$-Pfn1 antibody and counterstaining by DAPI. Scale bars, 40 μm.

FIG. 8A shows BT549 cells were treated with DMSO, 5 μM etoposide, and 1 mM HU for 12 hr, followed by Western blot analysis using the pSer$^{137}$-Pfn1 antibody. FIG. 8B shows MDA-MB-231, T47D, and MCF-7 cells were treated with DMSO or 200 nM SN38 for 16 hr, followed by Western blot analysis using the pSer$^{137}$-Pfn1 antibody. Red arrowheads indicate the DNA damage-induced 100 kDa protein. FIG. 8C shows HeLa cells were treated with 200 nM SN38 for 16 hr, lysed in SDS-free RIPA, and treated with or without alkaline phosphatase (AP) at 37° C. for 1 hr. Lysates were immunoprecipitated by the pSer137-Pfn1 antibody followed by Western blot analysis of proteins bound to the antibody and present in the inputs using a VCP-specific antibody. FIG. 8D shows Hela cells were treated with DMSO or 50 μM etoposide for 24 hours, lysed in denaturing buffer (1% SDS, 20 mM Tris-HCl, pH 7.4, 150 mM NaCl), and heated at 95° C. for 10 min. Samples were diluted 20-fold with ice cold buffer containing 20 mM Tris-HCl, pH 7.4, 150 mM NaCl, protease and phosphatase inhibitors, and clarified at >16,000 g for 10 min. Supernatants were subjected to immunoprecipitation by control IgG or VCP pan antibody. FIG. 8E shows Hela cells were treated with DMSO or 50 μM etoposide for 24 hours, lysed in denaturing buffer (1% SDS, 20 mM Tris-HCl, pH 7.4, 150 mM NaCl), and heated at 95° C. for 10 min. Samples were diluted 20-fold with ice cold buffer containing 20 mM Tris-HCl, pH 7.4, 150 mM NaCl, protease and phosphatase inhibitors, and clarified at >16,000 g for 10 min. Supernatants were subjected to immunoprecipitation by the pSer$^{137}$-Pfn1 antibody. IP samples from (D) were analyzed by Western blot using the pSer$^{137}$-Pfn1 or VCP pan antibodies. IP and input samples from (E) were analyzed by Western blot using the VCP pan antibody. FIG. 8F shows Hela cells were infected with shLuc or two distinct shRNAs targeting human VCP. Western blot showing effective VCP knockdown after 4 days. Cells were treated with 5 μM etoposide for 6 hr followed by immunofluorescence staining by the pSer$^{784}$-VCP antibody and counterstaining by DAPI. Scale bars, 10 μm. FIG. 8G shows U2OS cells were treated with 50 μM etoposide for 1 hr, recovered for 90 min, detergent-extracted, fixed, and subjected to double immunofluorescence labeling using the pSer$^{137}$-Pfn1 (rabbit, detecting pSer$^{784}$-VCP) antibody and a BRCA1-specific (mouse) antibody. DAPI was used for counterstaining. Representative images showing partial co-localization of pSer$^{784}$-VCP and BRCA1 in DNA damage foci of <10% of the cells and no co-localization in >90% of the cells. More than 100 cells per condition have been analyzed. Scale bars, 4 μm.

FIG. 9A shows Hela cells treated with DMSO or SN38 (200 nM, 16 h) were analyzed by western blot using the pSer$^{137}$-Pfn1 or pSer784-VCP antibodies. FIG. 9B shows Hela cells treated with etoposide (50 μM, 1 h) were lysed, incubated at 37° C. for 1 h with or without calf intestinal alkaline phosphatase, and analyzed by western blot using the pSer$^{137}$-Pfn1, pSer$^{784}$-VCP, or pan-VCP antibodies. FIG. 9C shows Hela cells treated with DMSO or etoposide (50 μM, 6 h) were subjected to immunoprecipitation by control immunoglobulin G (IgG) or pan-VCP antibody, followed by western blot using the pSer$^{137}$-Pfn1, pSer$^{784}$-VCP, and pan-VCP antibodies. FIG. 9D shows Hela cells treated with DMSO or SN38, as in (A), were subjected to immunoprecipitation using the pSer$^{137}$-Pfn1 or pSer$^{784}$-VCP antibodies, followed by western blot using a pan-VCP antibody. FIG. 9E shows HeLa cells were treated with 200 nM of SN38 for 16 h and immunostained with the pSer$^{784}$-VCP antibody. FIG. 9F shows Hela cells were treated with 50 μM of etoposide for 1 h, followed by double immunostaining using the pSer$^{137}$-Pfn1 and pSer$^{784}$-VCP antibodies.

FIG. 9G shows U2OS cells were treated with 50 μM of etoposide for 1 h, recovered for 90 min, and detergent-extracted before fixation and double staining by the pSer$^{137}$-Pfn1 and 53BP1 antibodies. FIG. 9H shows U2OS cells were treated with 50 μM of etoposide for 1 h, recovered for 90 min, and detergent-extracted before fixation and double staining by pSer$^{784}$-VCP and γH2AX (H) antibodies. FIG. 9I shows representative images in the SPECS TMA immunostained in parallel by the pSer$^{137}$-Pfn1 and pSer$^{784}$-VCP antibodies. FIG. 9J shows univariate Kaplan-Meier analysis of the SPECS TMA stained in (G). Nuclear Allred scores were binarized into low (0-4) versus high (5-8) groups. Two extra interpretable cases stained by the pSer137-Pfn1 antibody (n=46) (but not by pSer784-VCP, n=44) were included in the analysis. p values were based on Log-rank test. More than 100 cells per experiment were analyzed for (D)-(F). Data in (A)-(H) have been independently confirmed 2-3 times. Scale bars, 20 μm (E), 4 μm (F-H), and 10 μm (I).

FIG. 10A shows BT549 cells were laser micro-irradiated and double labeled at various time points by the pSer$^{784}$-VCP/NBS1 or VCP/NBS1 antibody pairs. Experiment was independently performed twice with similar results. FIG. 10B shows Hela cells were treated continuously with 50 M of etoposide, lysed by RIPA buffer (no SDS) at the indicated time points, and analyzed for soluble and insoluble fractions by western blot. Band intensities were plotted over time for each indicated antibody. Data were independently confirmed three times. Scale bars, 10 μm.

FIG. 11A shows U2OS cells were laser micro-irradiated, fixed at different time points, and subjected to double immunofluorescence staining using the pSer$^{784}$-VCP/NBS1 antibody pair. FIG. 11B shows U2OS cells were laser micro-irradiated, fixed at different time points, and subjected to double immunofluorescence staining using the VCP/NBS1 antibody pair. FIG. 11C shows Hela cells were treated with 10 mM hydroxyurea for the indicated amounts of time and analyzed by Western blot for pSer$^{784}$-VCP and pSer$^{345}$-Chk1.

FIG. 12A shows HeLa cells stably expressing GFP or RNAi-resistant VCP-GFP (WT or mutants) were infected with shLuc or shVCP1 and 2 combined. Cells were analyzed 4 days later by western blot using antibodies against VCP (detecting both endogenous VCP and exogenous VCP-GFP) or actin. FIG. 12B shows cells in (A) were treated with 50 μM of etoposide for 30 min, recovered for 1 h, lysed by RIPA buffer (no SDS), and analyzed for soluble and insoluble fractions by western blot using a K48-linkage-specific polyubiquitin antibody controlled by histone H3 or GAPDH. FIG. 12C shows etoposide-treated Hela cells, as in (B), were subjected to subcellular fractionation, followed by western blot analysis of the resulting cytoplasmic, nucleoplasmic, and chromatin fractions using the K48-ubiquitin antibody controlled by GAPDH, actin, and histone H3. Densitometry was performed to quantify K48-polyubiquitin levels in (B) and (C), which were subsequently normalized over the internal controls. FIG. 12D shows Chromatin fractions from (C) were analyzed by western blot for Ku70. FIG. 12 E shows VCP knockdown and rescue Hela cells were treated with 50 μM of etoposide for 30 min, recovered for 2 h in the presence of 20 μM of MG-132, and lysed with RIPA buffer. Soluble and insoluble fractions were analyzed by western blot for HIF1α and K48-ubiquitin, with tubulin and H3 as loading controls.

FIG. 13A shows RIPA lysis of Hela cells as described in FIG. 5B. Samples were blotted for tubulin (soluble marker) and histone H3 (insoluble marker). FIG. 13B shows HeLa samples were blotted for tubulin (cytosolic marker), PELP1 (nuclear marker), and histone H3 (chromatin marker). FIG. 13C show equal numbers of HeLa cells were treated with 5 μM NMS-873 for 1 hr and subjected to subcellular fractionation. Cytoplasm, nucleoplasm, and chromatin fractions were analyzed by Western blot using an antibody specific to K48-linked polyubiquitin. FIG. 13D show U20S cells stably expressing GFP or RNAi-resistant VCP-GFP (WT or mutants) were infected with shLuc or shVCP #1 and #2 combined. Cells were analyzed 4 days later by Western blot using antibodies against VCP (detecting both endogenous VCP and exogenous VCP-GFP) or actin. FIG. 13E shows cells in (G) were treated with 50 μM etoposide for 30 min, recovered for 1 hr, and subjected to subcellular fractionation followed by Western blot analysis of the cytoplasmic, nucleoplasmic, and chromatin fractions using the K48-ubiquitin antibody controlled by GAPDH, actin, and histone H3. FIG. 13F shows RIPA lysed HeLa samples from FIG. 5E were blotted for tubulin (soluble marker) and histone H3 (insoluble marker). FIG. 13G shows HeLa cells expressing RNAi-resistant wild type or mutant VCP were infected with shVCP #1, treated with 50 μM etoposide for 30 min, recovered for 2 h in the presence of 20 μM MG-132, and subjected to RT-qPCR for HIF1 using GAPDH for normalization. Shown are mean±SD of three technical replicates of one biological replicate. FIG. 13H shows RIPA lysed HeLa samples from FIG. 6C were blotted for tubulin (soluble marker) and histone H3 (insoluble marker). FIG. 13I shows nucleoplasmic and chromatin fractions of Hela cells from FIG. 6D were blotted for histone H3. Note that for (A, B, F, H, I) same samples from the experiments described in the main figures were rerun and reanalyzed here. Same results were confirmed by three biologically independent experiments.

FIG. 14A shows Hela cells were treated with 5 μM etoposide or 1 mM HU for 20 hr, lysed with SDS-free RIPA buffer, and immunoprecipitated by either the pSer784-VCP antibody or a pan VCP antibody. Antibody-bound proteins were analyzed by Western blot for K48-ubiquitin, total VCP and pSer784-VCP. Same amount of control IgG was used to bind the etoposide-treated HeLa samples to control for non-specific binding. FIG. 14B shows MDA-MB-231 cells were treated with 5 μM etoposide for 22 hr, lysed, and immunoprecipitated by the VCP or pSer784-VCP antibodies, controlled by non-specific IgG as in (A). Samples were analyzed by Western blot for K48-ubiquitin, NPL4, and UFD1. Total VCP bound by the antibodies were visualized by silver staining. FIG. 14C shows western blot showing similar expression levels of VCP-FLAG (WT and mutants) relative to endogenous VCP in the stable MDA-MB-231 cells. YFP-FLAG was expressed as a control. FIG. 14D shows MDA-MB-231 stable cells from (C) were treated with DMSO or 5 μM etoposide for 12 hr, subjected to chromatin fractionation, and analyzed by Western blot using anti-VCP or FLAG antibodies, with histone H3 as the loading control.

FIG. 15A shows Hela cells were treated with 5 μM of etoposide overnight, lysed with SDS-free RIPA, and immunoprecipitated first with the pSer$^{784}$-VCP antibody; the supernatant of which was subsequently immunoprecipitated by the VCP pan-antibody. FIG. 15B shows MDA-MB-231 cells stably expressing YFP-FLAG or VCP-FLAG (S784A versus S784D) were treated with 200 nM of SN38 overnight, and nucleoplasmic fractions were immunoprecipitated by the anti-FLAG antibody. FIG. 15C shows Hela cells expressing RNAi-resistant VCP-GFP were infected with combined shVCP1 and 2, treated with 50 μM of etoposide for 45 min, recovered for 1 h, lysed with SDS-free RIPA buffer, and analyzed by western blot. FIG. 15D shows similarly treated Hela cells as in (C) were fractionated and analyzed by western blot using nucleoplasm and chromatin fractions. Data were independently confirmed two to three times.

FIG. 16A shows shLuc- or shVCP-infected stable Hela cells were treated with 50 μM of etoposide for 30 min, recovered for 1 h, lysed by RIPA, and analyzed by western blot. FIG. 16B shows shLuc- or shVCP-infected stable U2OS cells were treated with vehicle or different drugs for 16 h, and subjected to colony formation assays for 10-14 days. Relative effects represent normalized drug/vehicle percentages. Shown are means±SEM of three technical replicates of single biological experiments for each drug. p Values were based on unpaired t tests (S784A versus WT or S784D). FIG. 16C shows shVCP2-infected U2OS stable cells were treated with 25 μM of etoposide for 30 min followed by 1 h of recovery or 1 mM HU for 16 h. Cells were subjected to the comet assay under the alkaline condition, and tail DNA percentages were calculated. Shown are single biological experiments with 150-300 cells analyzed per condition. Error bars represent SEM. p Values were based on unpaired t tests. * p<0.05,  p<0.01, * p<0.001, **** p<0.0001. Results in (B) and (C) were confirmed by three biological replicates. FIG. 16D shows working model of enhanced substrate extraction from chromatin by VCP upon DNA-damage-induced Ser784 phosphorylation. In this model, Ser784 phosphorylation is a relatively late DDR event that occurs either in the nucleoplasm or on chromatin after VCP binding to polyubiquitinated substrates (both scenarios are depicted). Ser784 phosphorylation does not abolish chromatin recruitment of VCP but promotes substrate extraction and subsequent degradation at least partially because of its weakened interaction with cofactors NPL4 and UFD1, which directly bind substrates. Dissociated pSer$^{784}$-VCP can regain access to chromatin and extract more substrates.

FIG. 17A shows MDA-MB-231 cells were pre-treated with NMS-873 for 30 min followed by 20 min treatment with 25 μM etoposide. Cells were lysed by SDS-free RIPA buffer, and soluble fractions were analyzed by Western blot for the indicated proteins. Red asterisks indicate pS/TQ motif-containing proteins whose levels are reduced by NMS-873. FIG. 17B shows Hela cells stably expressing GFP or VCP-GFP (WT and mutants) were infected with shLuc, shVCP #1, or shVCP #2 individually. Four days later, they were treated with 1 mM HU for 4 hr, lysed by SDS-free RIPA buffer, followed by Western blot analysis of the soluble proteins with the indicated antibodies. FIG. 17C shows VCP knockdown and rescue Hela cells were treated with 50 μM etoposide for 30 min, recovered for 1 hr, and subjected to cellular fractionation. Nucleoplasm and chromatin fractions were analyzed by Western blot using the indicated antibodies. PELP1 and histone H3 were blotted as loading controls. FIG. 17D shows VCP knockdown and rescue Hela cells were treated with 5 mM HU for 4 hr and subjected to cellular fractionation and Western blot for ATR similarly to (C). FIG. 17E shows nucleoplasm and chromatin fractions from (C) were loaded proportionally to show the relative abundance of total ATM in either compartment. FIG. 17F shows VCP knockdown and rescue Hela cells were treated for 15 min with 50 μM etoposide, recovered for 1 hr or 2 hr, detergent extracted, fixed with paraformaldehyde, and immunostained for pSer1981-ATM. Shown are single biological replicates containing ~2000 cells per condition. Error bars represent SD. Similar results were confirmed by three biologically independent experiments. P values were based on 2-tailed unpaired t-test. *, p<0.05; ****, p<0.0001.

FIG. 18A shows Hela cells stably expressing GFP or RNAi-resistant VCP-GFP (WT or mutants) were infected with shLuc or shVCP #1 and #2 combined. Same number of cells were plated and grown without treatment for 10 days in colony formation assays. FIG. 18B shows HeLa and U2OS stable cells expressing GFP or RNAi-resistant VCP-GFP (WT and mutants) were infected with shVCP #1 and #2 combined and grown in colony formation assays for 10 days as in (A). Viable cells were quantified by Alamar blue. FIG. 18C shows Stable U20S cells expressing RNAi-resistant VCP-GFP (S784A vs. S784D) were infected with shVCP #2 for 4 days, treated with vehicle or PARP inhibitors olaparib or niraparib at the indicated concentrations for 16 hr, and allowed to grow in colony formation assays for 10-14 days. Colonies were stained and quantified, and relative survival was calculated by normalizing drug-treated values over vehicle controls. FIG. 18D shows Stable HeLa cells expressing RNAi-resistant VCP-GFP (S784A vs. S784D) were infected with combined shVCP #1 and shVCP #2, treated with HU and 5FU at the indicated concentrations for 16 hr, and subjected to colony formation for 7-10 days and quantification as in (C). Values in (B-D) represent mean±SEM of three technical replicates of single experiments. Results were confirmed by three biologically independent experiments. P values were based on unpaired student's t-test at the indicated drug concentrations. *<0.05, <0.01, * p<0.001.

DETAILED DESCRIPTION

Figure 1:
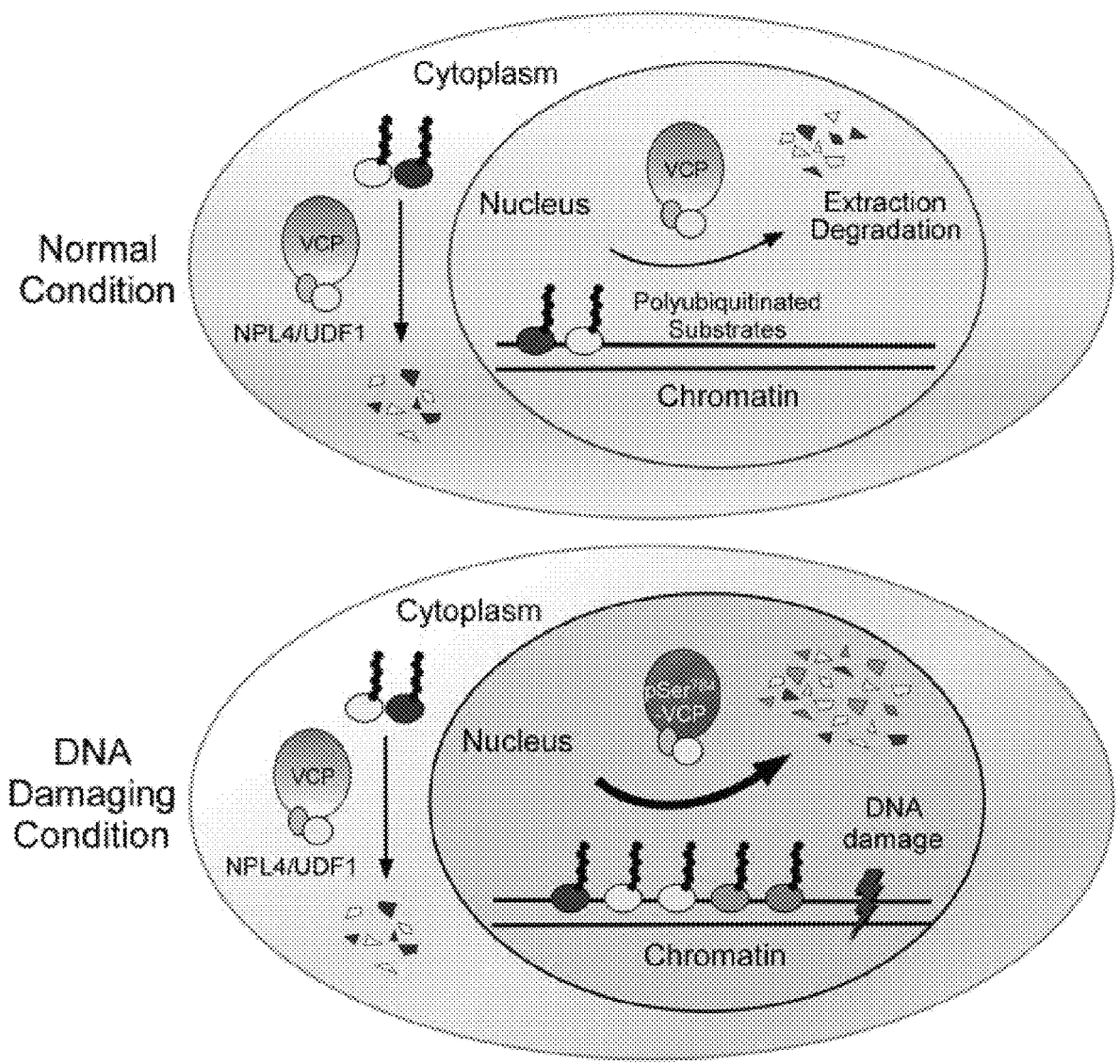
FIG. 1 depicts graphically the functional effects of valosin-containing protein (VCP) under normal conditions and the functional effects of VCP-$Ser^{784}$ phosphorylation during DNA damaging conditions.

The evolutionarily conserved DNA damage response (DDR) consists of intimately connected cellular processes which collectively maintain genome stability and determine cell fate. Many DDR events are orchestrated by proteostatic changes influencing protein level and localization in a spatiotemporally choreographed manner. An important aspect of proteostasis during DDR is proteasomal degradation of lysine 48 (K48)-linked polyubiquitinated proteins. This is best understood on chromatin, especially around DNA damage sites, where rapid protein reorganization takes place to enable DNA repair and checkpoint signaling. Valosin-Containing Protein (VCP) regulates the efficient degradation of many chromatin-associated proteins to facilitate their turnover. Though the mechanisms which regulate VCP activity and function are not fully understood. Applicant has discovered compositions and certain methods to quantify VCP phosphorylation at $Ser^{784}$ can be used to select subjects who can benefit from genotoxic therapies or those that would benefit from sensitization by phosphatidylinositol 3-kinase-related kinases (PIKK) inhibitors. The present disclosure encompasses use of the compositions and methods to quantify VCP phosphorylation at $Ser^{784}$ to guide treatment decisions, select subjects for clinical trials, and evaluate the clinical efficacy of certain therapeutic interventions.

Discussed below are components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules of the compound are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Other aspects and iterations of the invention are described more thoroughly below.

I. Definitions

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation of in the numerical quantity that can occur, for example, through typical measuring techniques and equipment, with respect to any quantifiable variable, including, but not limited to, mass, volume, time, distance, and amount. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations, which can be up to ±5%, but can also ±4%, 3%, 2%, 1%, etc. Whether or not modified by the term "about," the claims include equivalents to the quantities.

The term "antibody," as used herein, is used in the broadest sense and encompasses various antibody and antibody-like structures, including but not limited to full-length monoclonal, polyclonal, and multispecific (e.g., bispecific, trispecific, etc.) antibodies, as well as heavy chain antibodies and antibody fragments provided they exhibit the desired antigen-binding activity. The domain(s) of an antibody that is involved in binding an antigen is referred to as a "variable region" or "variable domain," and is described in further detail below. A single variable domain may be sufficient to confer antigen-binding specificity. Preferably, but not necessarily, antibodies useful in the discovery are produced recombinantly. Antibodies may or may not be glycosylated, though glycosylated antibodies may be preferred. An "isolated" antibody is one which has been separated from a component of its natural environment. In some embodiments, an antibody is purified to greater than 95% or 99% purity as determined by methods known in the art.

In addition to antibodies described herein, it may be possible to design an antibody mimetic or an aptamer using methods known in the art that functions substantially the same as an antibody of the invention. An "antibody mimetic" refers to a polypeptide or a protein that can specifically bind to an antigen but is not structurally related to an antibody. Antibody mimetics have a mass of about 3 kDa to about 20 kDa. Non-limiting examples of antibody mimetics are affibody molecules, affilins, affimers, alphabodies, anticalins, avimers, DARPins, and monobodies. Aptamers are a class of small nucleic acid ligands that are composed of RNA or single-stranded DNA oligonucleotides and have high specificity and affinity for their targets. Aptamers interact with and bind to their targets through structural recognition, a process similar to that of an antigen-antibody reaction. Aptamers have a lower molecular weight than antibodies, typically about 8-25 kDa.

The terms "full length antibody" and "intact antibody" may be used interchange-ably, and refer to an antibody having a structure substantially similar to a native anti-body structure or having heavy chains that contain an Fc region as defined herein. The basic structural unit of a native antibody comprises a tetramer. Each tetramer is composed of two identical pairs of polypeptide chains, each pair having one "light" chain (about 25 kDa) and one "heavy" chain (about 50-70 kDa). Light chains are classified as gamma, mu, alpha, and lambda. Heavy chains are classified as gamma, mu, alpha, delta, or epsilon, and define the antibody's isotype as IgG, IgM, IgA, IgD and IgE, respectively. The amino-terminal portion of each light and heavy chain includes a variable region of about 100 to 110 or more amino acid sequences primarily responsible for antigen recognition (VL and VH, respectively). The carboxy-terminal portion of each chain defines a constant region primarily responsible for effector function. Within light and heavy chains, the variable and constant regions are joined by a "J" region of about 12 or more amino acid sequences, with the heavy chain also including a "D" region of about 10 more amino acid sequences. Intact antibodies are properly cross-linked via disulfide bonds, as is known in the art.

The variable domains of the heavy chain and light chain of an antibody generally have similar structures, with each domain comprising four conserved frame-work regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, anti-bodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clark-son et al., Nature 352:624-628 (1991).

"Framework region" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence: FR1-HVR1-FR2-HVR2-FR3-HVR3-FR4. The FR domains of a heavy chain and a light chain may differ, as is known in the art.

The term "hypervariable region" or "HVR" as used herein refers to each of the regions of a variable domain which are hypervariable in sequence (also commonly referred to as "complementarity determining regions" or "CDR") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). As used herein, "an HVR derived from a variable region" refers to an HVR that has no more than two amino acid substitutions, as compared to the corresponding HVR from the original variable region. Exemplary HVRs herein include: (a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987)); (b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991)); (c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262:732-745 (1996)); (d) CDR1-IMGT (positions 27-38), CDR2-IMGT (positions 56-65), and CDR3-IMGT regions (positions 105-116 or 105-117), which are based on IMGT unique numbering (Lefranc, "The IMGT unique numbering for Immunoglobulins, T cell receptors and Ig-like domains," The Immunologist, 1999, 7:132-136; Lefranc et al., Nucleic Acids Research, 2009, 37 (Database issue): D1006-D1012; Ehrenmann et al., "Chapter 2: Standardized Sequence and Structure Analysis of Antibody Using IMGT," in Antibody Engineering Volume 2, Eds. Roland E. Kontermann and Stefan Dubel, 2010, Springer-Verlag Berlin Heidelberg, doi: 10.1007/978-3-642-01147-4; www.imgt.org/IMGTScientificChart/Nomenclature/IMGT-FRCDRdefinition.html), and (e) combinations of (a), (b), (c), and/or (d), as defined below for various antibodies of this disclosure. Unless otherwise indicated, HVR residues and other residues in the variable domain (e.g., FR residues) that are assigned sequence identification numbers are numbered based on IMGT unique numbering, supra.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

A "variant Fc region" comprises an amino acid sequence that can differ from that of a native Fc region by virtue of one or more amino acid substitution(s) and/or by virtue of a modified glycosylation pattern, as compared to a native Fc region or to the Fc region of a parent polypeptide. In an example, a variant Fc region can have from about one to about ten amino acid substitutions, or from about one to about five amino acid substitutions in a native sequence Fc region or in the Fc region of the parent polypeptide. The variant Fc region herein may possess at least about 80% homology, at least about 90% homology, or at least about 95% homology with a native sequence Fc region and/or with an Fc region of a parent polypeptide.

An "antibody fragment" refers to a molecule other than an intact antibody that comprises a portion of an intact antibody that binds the antigen to which the intact antibody binds. Non-limiting examples of antibody fragments include but are not limited to Fv, Fab, Fab', Fab'-SH, F(ab')2; single-chain forms of antibodies and higher order variants thereof; single-domain antibodies, and multispecific antibodies formed from antibody fragments.

Single-chain forms of antibodies, and their higher order forms, may include, but are not limited to, single-domain antibodies, single chain variant fragments (scFvs), divalent scFvs (di-scFvs), trivalent scFvs (tri-scFvs), tetravalent scFvs (tetra-scFvs), diabodies, and triabodies and tetrabodies. ScFv's are comprised of heavy and light chain variable regions connected by a linker. In most instances, but not all, the linker may be a peptide. A linker peptide is preferably from about 5 to 30 amino acids in length, or from about 10 to 25 amino acids in length. Typically, the linker allows for stabilization of the variable domains without interfering with the proper folding and creation of an active binding site. In preferred embodiments, a linker peptide is rich in glycine, as well as serine or threonine. ScFvs can be used to facilitate phage display or can be used for flow cytometry, immunohistochemistry, or as targeting domains. Methods of making and using scFvs are known in the art. ScFvs may also be conjugated to a human constant domain (e.g. a heavy constant domain is derived from an IgG domain, such as IgG1, IgG2, IgG3, or IgG4, or a heavy chain constant domain derived from IgA, IgM, or IgE). Diabodies, triabodies, and tetrabodies and higher order variants are typically created by varying the length of the linker peptide from zero to several amino acids. Alternatively, it is also well known in the art that multivalent binding anti-body variants can be generated using self-assembling units linked to the variable domain.

A "single-domain antibody" refers to an antibody fragment consisting of a single, monomeric variable antibody domain.

Multispecific antibodies include bi-specific antibodies, tri-specific, or anti-bodies of four or more specificities. Multispecific antibodies may be created by combining the heavy and light chains of one antibody with the heavy and light chains of one or more other antibodies. These chains can be covalently linked.

"Monoclonal antibody" refers to an antibody that is derived from a single copy or clone, including e.g., any eukaryotic, prokaryotic, or phage clone. "Monoclonal antibody" is not limited to antibodies produced through hybridoma technology. Monoclonal antibodies can be produced using hybridoma techniques well known in the art, as well as recombinant technologies, phage display technologies, synthetic technologies or combinations of such technologies and other technologies readily known in the art. Furthermore, the monoclonal antibody may be labeled with a detectable label, immobilized on a solid phase and/or conjugated with a heterologous compound (e.g., an enzyme or toxin) according to methods known in the art.

A "heavy chain antibody" refers to an antibody that consists of two heavy chains. A heavy chain antibody may be an IgG-like antibody from camels, llamas, alpacas, sharks, etc., or an IgNAR from a cartilaginous fish.

A "humanized antibody" refers to a non-human antibody that has been modified to reduce the risk of the non-human antibody eliciting an immune response in humans following administration but retains similar binding specificity and affinity as the starting non-human antibody. A humanized antibody binds to the same or similar epitope as the non-human antibody. The term "humanized antibody" includes an antibody that is composed partially or fully of amino acid sequences derived from a human antibody germline by altering the sequence of an antibody having non-human hypervariable regions ("HVR"). The simplest such alteration may consist simply of substituting the constant region of a human antibody for the murine constant region, thus resulting in a human/murine chimera which may have sufficiently low immunogenicity to be acceptable for pharmaceutical use. Preferably, the variable region of the antibody is also humanized by techniques that are by now well known in the art. For example, the framework regions of a variable region can be substituted by the corresponding human framework regions, while retaining one, several, or all six non-human HVRs. Some framework residues can be substituted with corresponding residues from a non-human VL domain or VH domain (e.g., the non-human antibody from which the HVR residues are derived), e.g., to restore or improve specificity or affinity of the humanized antibody. Substantially human framework regions have at least about 75% homology with a known human framework sequence (i.e. at least about 75%, at least about 80%, at least about 85%, at least about 90%, at least about 95%, or at least about 99% sequence identity). HVRs may also be randomly mutated such that binding activity and affinity for the antigen is maintained or enhanced in the context of fully human germline framework regions or framework regions that are substantially human. As mentioned above, it is sufficient for use in the methods of this discovery to employ an antibody fragment. Further, as used herein, the term "humanized antibody" refers to an antibody comprising a substantially human framework region, at least one HVR from a nonhuman antibody, and in which any constant region present is substantially human. Substantially human constant regions have at least about 90% with a known human constant sequence (i.e. about 90%, about 95%, or about 99% sequence identity). Hence, all parts of a humanized antibody, except possibly the HVRs, are substantially identical to corresponding pairs of one or more germline human immunoglobulin sequences.

If desired, the design of humanized immunoglobulins may be carried out as follows, or using similar methods familiar to those with skill in the art (for example, see Almagro, et al. Front. Biosci. 2008, 13 (5): 1619-33). A murine antibody variable region is aligned to the most similar human germline sequences (e.g. by using BLAST or similar algorithm). The CDR residues from the murine antibody sequence are grafted into the similar human "acceptor" germline. Subsequently, one or more positions near the CDRs or within the framework (e.g., Vernier positions) may be reverted to the original murine amino acid in order to achieve a humanized antibody with similar binding affinity to the original murine antibody. Typically, several versions of humanized antibodies with different re-version mutations are generated and empirically tested for activity. The humanized antibody variant with properties most similar to the parent murine antibody and the fewest murine framework reversions is selected as the final humanized antibody candidate.

The term "specifically binds," as used herein with regards to epitope binding agents, means that an epitope binding agent does not cross react to a significant extent with other epitopes on the protein of interest (e.g., VCP), or on other proteins in general.

The terms "Valosin-Containing Protein" or "VCP" encompasses all VCP isoforms, whether full-length, truncated, or post-translationally modified. In many animals, including but not limited to humans, non-human primates, rodents, fish, cattle, frogs, goats, and chicken, VCP is encoded by the gene VCP gene. The gene encoding VCP is located on chromosome 9 (band 9p13.3) in humans. VCP is also known as or p97 in mammals and CDC48 in *S. cerevisiae*, is an ATPase enzyme present in all eukaryotes and archaebacteria. Its main function is to segregate protein molecules from large cellular structures such as protein assemblies, organelle membranes and chromatin, and thus facilitate the degradation of released polypeptides by the multi-subunit protease proteasome. p97/CDC48 is a member of the AAA+ (extended family of ATPases associated with various cellular activities) ATPase family. Enzymes of this family are found in all species from bacteria to humans. Many of them are important chaperones that regulate folding or unfolding of substrate proteins. p97/CDC48 is a type II AAA+ ATPase, which means that it contains two tandem ATPase domains (named D1 and D2, respectively). The two ATPase domains are connected by a short polypeptide linker. A domain preceding the D1 domain (N-terminal domain) and a short carboxyl-terminal tail are involved in interaction with cofactors. The N-domain is connected to the D1 domain by a short N-D1 linker. Most known substrates of p97/CDC48 are modified with ubiquitin chains and degraded by the 26S proteasome. Accordingly, many p97/CDC48 coenzymes and adaptors have domains that can recognize ubiquitin. It has become evident that the interplays between ubiquitin and p97/CDC48 cofactors are critical for many of the proposed functions, although the precise role of these interactions remains to be elucidated.

In an exemplary aspect, the a full length VCP polypeptide, which is 806 amino acids in length includes the amino acid sequence of SEQ ID NO: 20
(MASGADSKGDDLSTAILKQKNRPNRLIVDEAINEDNSVVSLSQPKMDEL
QLFRGDTVLLKGKKRREAVCIVLSDDTCSDEKIRMNRVVRNNLRVRLGDV
ISIQPCPDVKYGKRIHVLPIDDTVEGITGNLFEVYLKPYFLEAYRPIRKG
DIFLVRGGMRAVEFKVVETDPSPYCIVAPDTVIHCEGEPIKREDEEESLN
EVGYDDIGGCRKQLAQIKEMVELPLRHPALFKAIGVKPPRGILLYGPPGT
GKTLIARAVANETGAFFFLINGPEIMSKLAGESESNLRKAFEEAEKNAPA
IIFIDELDAIAPKREKTHGEVERRIVSQLLTLMDGLKQRAHVIVMAATNR
PNSIDPALRRFGRFDREVDIGIPDATGRLEILQIHTKNMKLADDVDLEQV
ANETHGHVGADLAALCSEAALQAIRKKMDLIDLEDETIDAEVMNSLAVTM
DDFRWALSQSNPSALRETVVEVPQVTWEDIGGLEDVKRELQELVQYPVEH
PDKFLKFGMTPSKGVLFYGPPGCGKTLLAKAIANECQANFISIKGPELLT
MWFGESEANVREIFDKARQAAPCVLFFDELDSIAKARGGNIGDGGGAADR
VINQILTEMDGMSTKKNVFIIGATNRPDIIDPAILRPGRLDQLIYIPLPD
EKSRVAILKANLRKSPVAKDVDLEFLAKMTNGFSGADLTEICQRACKLAI
RESIESEIRRERERQTNPSAMEVEEDDPVPEIRRDHFEEAMRFARRSVSD
NDIRKYEMFAQTLQQSRGFGSFRFPSGNQGGAGPSQGSGGGTGGSVYTED
NDDDLYG).

The terms "treat," "treating," or "treatment" as used herein, refer to both therapeutic treatment and prophylactic or preventative measures, wherein the object is to prevent or slow down (lessen) an undesired physiological change or disease/disorder. Beneficial or desired clinical results include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the disease, condition, or disorder as well as those prone to have the disease, condition or disorder or those in which the disease, condition or disorder is to be prevented.

II. pSer$^{784}$-VCP Antibody

A "pSer$^{784}$-VCP antibody," as used herein, refers to an isolated antibody that binds to VCP which is phosphorylated on the serine residue at position 784 with an affinity constant or affinity of interaction (KD) between about 0.1 pM to about 10 μM, preferably about 0.1 pM to about 1 μM, more preferably about 0.1 pM to about 100 nM. Methods for determining the affinity of an antibody for an antigen are known in the art, and further illustrated in the Examples. Thus, the pSer$^{784}$-VCP antibodies of the present disclosure are phospho-specific antibodies, i.e. detect only the phosphorylated forms of VCP, specifically, phosphorylation at serine residue 784. pSer$^{784}$-VCP antibodies useful herein include those which are suitable for methods to guide treatment decisions, select subjects for clinical trials, and evaluate the clinical efficacy of certain therapeutic interventions as described herein.

In one example, a pSer$^{784}$-VCP antibody comprises a VL that has one or more HVRs derived from SEQ ID NO: 17 or a VH that has one or more HVRs derived from SEQ ID NO: 16. The HVR derived from SEQ ID NO: 17 may be a VL CDR1, a VL CDR2, a VL CDR3, or any combination thereof. In certain embodiments, the VL may comprise a CDR1 of SEQ ID NO: 13, a CDR2 of SEQ ID NO: 14, a CDR3 of SEQ ID NO: 15, or any combination thereof (e.g. antibodies 1-7 in Table A). The HVR derived from SEQ ID NO: 17 may be a VH CDR1, a VH CDR2, a VH CDR3, or any combination thereof. In certain embodiments, the VH may comprise a CDR1 of SEQ ID NO: 10, a CDR2 of SEQ ID NO: 11, a CDR3 of SEQ ID NO: 12, or any combination thereof (e.g. antibodies 8-14 in Table A). In various embodiments above, the antibody may be a humanized antibody, or the antibody may have a VL with 90, 91, 92, 93, 94, 95, 96, 97, 98, 99, or 100% identity to SEQ ID NO: 17 and/or a VH with 90, 91, 92, 93, 94, 95, 96, 97, 98, 99 or 100% identity to SEQ ID NO: 16. In each of the above embodiments, the pSer$^{784}$-VCP antibody may optionally comprise one or more constant regions, or a portion of a constant region, that is substantially human (i.e. at least 90%, 95%, or 99% sequence identity with a known human framework sequence). The present disclosure also encompasses the corresponding nucleic acid sequences of SEQ ID NO: 18, and 19, which can readily be determined by one of skill in the art, and may be incorporated into a vector or other large DNA molecule, such as a chromosome, in order to express an antibody of the disclosure.

TABLE A

|  | Light Chain HVR | | | Heavy Chain HVR | | |
| --- | --- | --- | --- | --- | --- | --- |
| Antibody | CDR1 | CDR2 | CDR3 | CDR1 | CDR2 | CDR3 |
| 1 | SEQ ID NO: 13 | | | | | |
| 2 | SEQ ID NO: 13 | SEQ ID NO: 14 | | | | |
| 3 | SEQ ID NO: 13 | SEQ ID NO: 14 | SEQ ID NO: 15 | | | |
| 4 | | SEQ ID NO: 14 | | | | |
| 5 | | SEQ ID NO: 14 | SEQ ID NO: 15 | | | |
| 6 | | | SEQ ID NO: 15 | | | |
| 7 | SEQ ID NO: 13 | | SEQ ID NO: 15 | | | |
| 8 | | | | SEQ ID NO: 10 | | |
| 9 | | | | SEQ ID NO: 10 | SEQ ID NO: 11 | |
| 10 | | | | SEQ ID NO: 10 | SEQ ID NO: 11 | SEQ ID NO: 12 |
| 11 | | | | | SEQ ID NO: 11 | |
| 12 | | | | | SEQ ID NO: 11 | SEQ ID NO: 12 |
| 13 | | | | | | SEQ ID NO: 12 |
| 14 | | | | SEQ ID NO: 10 | | SEQ ID NO: 12 |

TABLE A-continued

| Antibody | Light Chain HVR CDR1 | CDR2 | CDR3 | Heavy Chain HVR CDR1 | CDR2 | CDR3 |
|---|---|---|---|---|---|---|
| 15 | SEQ ID NO: 13 | | | SEQ ID NO: 10 | | |
| 16 | SEQ ID NO: 13 | | | SEQ ID NO: 10 | SEQ ID NO: 11 | |
| 17 | SEQ ID NO: 13 | | | SEQ ID NO: 10 | SEQ ID NO: 11 | SEQ ID NO: 7 |
| 18 | SEQ ID NO: 13 | | | | SEQ ID NO: 11 | |
| 19 | SEQ ID NO: 13 | | | | SEQ ID NO: 11 | SEQ ID NO: 12 |
| 20 | SEQ ID NO: 13 | | | | | SEQ ID NO: 12 |
| 21 | SEQ ID NO: 13 | | | SEQ ID NO: 10 | | SEQ ID NO: 12 |
| 22 | SEQ ID NO: 13 | SEQ ID NO: 14 | | SEQ ID NO: 10 | | |
| 23 | SEQ ID NO: 13 | SEQ ID NO: 14 | | SEQ ID NO: 10 | SEQ ID NO: 11 | |
| 24 | SEQ ID NO: 13 | SEQ ID NO: 14 | | SEQ ID NO: 10 | SEQ ID NO: 11 | SEQ ID NO: 12 |
| 25 | SEQ ID NO: 13 | SEQ ID NO: 14 | | | SEQ ID NO: 11 | |
| 26 | SEQ ID NO: 13 | SEQ ID NO: 14 | | | SEQ ID NO: 11 | SEQ ID NO: 12 |
| 27 | SEQ ID NO: 13 | SEQ ID NO: 14 | | | | SEQ ID NO: 12 |
| 28 | SEQ ID NO: 13 | SEQ ID NO: 14 | | SEQ ID NO: 10 | | SEQ ID NO: 12 |
| 29 | SEQ ID NO: 13 | SEQ ID NO: 14 | SEQ ID NO: 15 | SEQ ID NO: 10 | | |
| 30 | SEQ ID NO: 13 | SEQ ID NO: 14 | SEQ ID NO: 15 | SEQ ID NO: 10 | SEQ ID NO: 11 | |
| 31 | SEQ ID NO: 13 | SEQ ID NO: 14 | SEQ ID NO: 15 | SEQ ID NO: 10 | SEQ ID NO: 11 | SEQ ID NO: 12 |
| 32 | SEQ ID NO: 13 | SEQ ID NO: 14 | SEQ ID NO: 15 | | SEQ ID NO: 11 | |
| 33 | SEQ ID NO: 13 | SEQ ID NO: 14 | SEQ ID NO: 15 | | SEQ ID NO: 11 | SEQ ID NO: 12 |
| 34 | SEQ ID NO: 13 | SEQ ID NO: 14 | SEQ ID NO: 15 | SEQ ID NO: 10 | | SEQ ID NO: 12 |
| 35 | SEQ ID NO: 13 | SEQ ID NO: 14 | SEQ ID NO: 15 | | | SEQ ID NO: 12 |
| 36 | | SEQ ID NO: 14 | | SEQ ID NO: 10 | | |
| 37 | | SEQ ID NO: 14 | | SEQ ID NO: 10 | SEQ ID NO: 11 | |
| 38 | | SEQ ID NO: 14 | | SEQ ID NO: 10 | SEQ ID NO: 11 | SEQ ID NO: 12 |
| 39 | | SEQ ID NO: 14 | | | SEQ ID NO: 11 | |
| 40 | | SEQ ID NO: 14 | | | SEQ ID NO: 11 | SEQ ID NO: 12 |
| 41 | | SEQ ID NO: 14 | | | | SEQ ID NO: 12 |
| 42 | | SEQ ID NO: 14 | | SEQ ID NO: 10 | | SEQ ID NO: 12 |
| 43 | | SEQ ID NO: 14 | SEQ ID NO: 15 | SEQ ID NO: 10 | | |
| 44 | | SEQ ID NO: 14 | SEQ ID NO: 15 | SEQ ID NO: 10 | SEQ ID NO: 11 | |
| 45 | | SEQ ID NO: 14 | SEQ ID NO: 15 | SEQ ID NO: 10 | SEQ ID NO: 11 | SEQ ID NO: 12 |
| 46 | | SEQ ID NO: 14 | SEQ ID NO: 15 | | SEQ ID NO: 11 | |
| 47 | | SEQ ID NO: 14 | SEQ ID NO: 15 | | SEQ ID NO: 11 | SEQ ID NO: 12 |
| 48 | | SEQ ID NO: 14 | SEQ ID NO: 15 | | | SEQ ID NO: 12 |
| 49 | | SEQ ID NO: 14 | SEQ ID NO: 15 | SEQ ID NO: 10 | | SEQ ID NO: 12 |
| 50 | | | SEQ ID NO: 15 | SEQ ID NO: 10 | | |
| 51 | | | SEQ ID NO: 15 | SEQ ID NO: 10 | SEQ ID NO: 11 | |
| 52 | | | SEQ ID NO: 15 | SEQ ID NO: 10 | SEQ ID NO: 11 | SEQ ID NO: 12 |
| 53 | | | SEQ ID NO: 15 | | SEQ ID NO: 11 | |
| 54 | | | SEQ ID NO: 15 | | SEQ ID NO: 11 | SEQ ID NO: 12 |
| 55 | | | SEQ ID NO: 15 | | | SEQ ID NO: 12 |
| 56 | | | SEQ ID NO: 15 | SEQ ID NO: 10 | | SEQ ID NO: 12 |
| 57 | SEQ ID NO: 13 | | SEQ ID NO: 15 | SEQ ID NO: 10 | | |
| 58 | SEQ ID NO: 13 | | SEQ ID NO: 15 | SEQ ID NO: 10 | SEQ ID NO: 11 | |
| 59 | SEQ ID NO: 13 | | SEQ ID NO: 15 | SEQ ID NO: 10 | SEQ ID NO: 11 | SEQ ID NO: 12 |
| 60 | SEQ ID NO: 13 | | SEQ ID NO: 15 | | SEQ ID NO: 11 | |
| 61 | SEQ ID NO: 13 | | SEQ ID NO: 15 | | SEQ ID NO: 11 | SEQ ID NO: 12 |
| 62 | SEQ ID NO: 13 | | SEQ ID NO: 15 | | | SEQ ID NO: 12 |
| 63 | SEQ ID NO: 13 | | SEQ ID NO: 15 | SEQ ID NO: 10 | | SEQ ID NO: 12 |

TABLE B

Sequence Listing

| SEQ ID NO: | Description | Sequence |
|---|---|---|
| 1 | pSer784_VCP antibody imunogen | GGAGPpSQGSGGGTGC |
| 10 | 3E4 HC CDR1 | DYAMH |
| 11 | 3E4 HC CDR2 | WTNTETGEPTYADDFKG |
| 12 | 3E4 HC CDR3 | GWSFAY |
| 13 | 3E4 LC CDR1 | KSSQSLLYSNGKTYLN |
| 14 | 3E4 LC CDR2 | LVSKLDS |
| 15 | 3E4 LC CDR3 | VQGTHFPRT |
| 16 | 3E4 HC | QIQLVQSGPELKKPGETVKISCKASG YTFTDYAMHWVKQAPGKGLKWM GWTNTETGEPTYADDFKGRFAFSLET SASTAYLQINNLKNEDTATYFCARGWSF AYWGQGTLVTVSA |
| 17 | 3E4 LC | DVVMTQTPLTLSVTIGQPASISCKSS QSLLYSNGKTYLNWLLQRPGQS PKRLIYLVSKLDSGVPDRFTGSGSGTD FTLKISRVEAEDLGVYYCVQG THFPRTFGGGTKLEIK |
| 18 | 3E4 HC | CAGATCCAGTTGGTGCAGTCTGGA CCTGAGCTGAAGAAGCCTGGAGAGA CAGTCAAGATCTCCTGCAAGGCCTC |

TABLE B-continued

Sequence Listing

| SEQ ID NO: | Description | Sequence |
|---|---|---|
| 19 | 3E4 LC | TGGTTATACCTTCACAGACTATGCAATGCACTGGGTGAAGCAGGCTCCAGGAAAGGGTTTAAAGTGGATGGGCTGGACAAACACTGAGACTGGTGAGCCAACATATGCAGATGACTTCAAGGGACGGTTTGCCTTCTCTTTGGAAACCTCTGCCAGCACTGCCTATTTGCAGATCAACAACCTCAAAAATGAGGACACGGCTACATATTTCTGTGCTAGGGGCTGGTCGTTTGCTTACTGGGGCCAAGGGACTCTGGTGACTGTCTCTGCAGATGTTGTGATGACCCAGACTCCACTCACTTTGTCGGTTACCATTGGACAACCAGCCTCTATCTCTTGCAAGTCAAGTCAGAGCCTCTTATATAGTAATGGAAAAACCTATTTGAATTGGTTATTACAGAGGCCAGGCCAGTCTCCAAAGCGCCTAATCTATCTGGTGTCTAAACTGGACTCTGGAGTCCCTGACAGGTTCACTGGCAGTGGATCAGGAACAGATTTTACACTGAAAATCAGCAGAGTGGAGGCTGAGGATTTGGGAGTTTATTACTGCGTGCAAGGTACACATTTTCCTCGGACGTTCGGTGGAGGCACCAAGCTGGAAATCAAA |

In one embodiment, an antibody of the disclosure may comprise a light chain variable region comprising a CDR1 of amino acid sequence SEQ ID NO: 13 with zero to two amino acid substitutions, a CDR2 of amino acid sequence SEQ ID NO: 14 with zero to two amino acid substitutions, and a CDR3 of amino acid sequence SEQ ID NO: 15 with zero to two amino acid substitutions, or may comprise a heavy chain variable region comprising a CDR1 of amino acid sequence SEQ ID NO: 10 with zero to two amino acid substitutions, a CDR2 of amino acid sequence SEQ ID NO: 11 with zero to two amino acid substitutions, and a CDR3 of amino acid sequence SEQ ID NO: 12 with zero to two amino acid substitutions. In an exemplary embodiment, an antibody of the invention may comprise a light chain variable region comprising a CDR1 of amino acid sequence SEQ ID NO: 13, a CDR2 of amino acid sequence SEQ ID NO: 14, a CDR3 of amino acid sequence SEQ ID NO: 15, a heavy chain variable region comprising a CDR1 of amino acid sequence SEQ ID NO: 10, a CDR2 of amino acid sequence SEQ ID NO: 11, and a CDR3 of amino acid sequence SEQ ID NO: 12.

In other examples, a pSer$^{784}$-VCP antibody of the present disclosure is 3E4. The antibody heavy chain of the 3E4 antibody is encoded by SEQ ID NO: 18 and the light chain is encoded by SEQ ID NO: 19. In still other examples, pSer$^{784}$-VCP antibody of the present disclosure is a humanized antibody derived from 3E4.

In other examples, pSer$^{784}$-VCP antibody of the present disclosure competitively inhibits binding of a reference antibody to its epitope. An antibody is said to competitively inhibit binding of a reference antibody to a given epitope if the antibody preferentially binds to that epitope to the extent that it blocks binding of the reference antibody to the epitope by at least 50%, at least 60%, at least 70%, at least 80%, or at least 90%. Competitive inhibition can be determined by any method known in the art, for example, competition ELISA assays.

III. Measuring VCP Ser784 Phosphorylation in an Biological Sample

In some embodiments, the methods disclosed herein may comprise obtaining a biological sample from a subject and assaying the biological sample to measure the level of VCP-Ser784 phosphorylation, as disclosed herein. As used herein, the term "biological sample" may be, in non-limiting examples, a biological fluid, a tissue, a tissue homogenate, cells, a cellular lysate, a tissue or cell biopsy, skin cells, tumor or cancer cells, or any combination thereof. Any biological sample containing tumor or cancer cells to be assayed, is suitable. Numerous types of biological samples are known in the art. In some embodiments, the biological sample is a tissue sample such as a tissue biopsy. In some embodiments, the biological sample is a tissue sample such as a tissue biopsy. The tissue biopsy may be a biopsy of liver tissue. The biopsied tissue may be fixed, embedded in paraffin or plastic, and sectioned, or the biopsied tissue may be frozen and cryosectioned. Alternatively, the biopsied tissue may be processed into individual cells or an explant, or processed into a homogenate, a cell extract, a membranous fraction, or a protein extract. In other embodiments, the sample may be a bodily fluid containing tumor or cancer cells to be assayed. Non-limiting examples of suitable bodily fluids includes blood, plasma, or serum. In a specific embodiment, the biological sample is blood. The fluid may be used "as is", the cellular components may be isolated from the fluid, or a fraction may be isolated from the fluid using standard techniques. In some embodiments, the subject has a cancer or tumor diagnosis and the biological sample is a tumor or cancer biopsy.

Once a sample is obtained, it is processed in vitro in order to detect and measure the amount of one or more VCP polypeptides using an pSer$^{784}$-VCP antibody. All suitable methods for detecting and measuring an amount of protein using an antibody known to one of skill in the art are contemplated within the scope of the invention. Methods for detecting and measuring an amount of protein using an antibody (i.e. "antibody-based methods") are well known in the art. Non-limiting examples include an ELISA, a lateral flow assay, a sandwich immunoassay, a radioimmunoassay, an immunoblot or Western blot, flow cytometry, immunohistochemistry, and an array. A lateral flow assay may be a device intended to detect the presence (or absence) of a target analyte in sample.

In general, an antibody-based method of detecting and measuring an amount of VCP-Ser$^{784}$ phosphorylation comprises contacting some or all of the sample comprising a VCP polypeptide with a pSer$^{784}$-VCP antibody under conditions effective to allow for formation of a complex between the antibody and the VCP polypeptide. Typically, the entire sample is not needed, allowing one skilled in the art to repeatedly detect and measure the amount of VCP-Ser$^{784}$ phosphorylation in the sample over time. The method may occur in solution, or the antibody or VCP polypeptide may be immobilized on a solid surface. Non-limiting examples of suitable surfaces include microtitre plates, test tubes, beads, resins, and other polymers. Attachment to the substrate may occur in a wide variety of ways, as will be appreciated by those in the art. For example, the substrate and the antibody may be derivatized with chemical functional groups for subsequent attachment of the two. For example, the substrate may be derivatized with a chemical functional group including, but not limited to, amino groups, carboxyl groups, oxo groups or thiol groups. Using these functional groups, the antibody may be attached directly using the functional groups or indirectly using linkers. A pSer$^{784}$-VCP antibody may also be attached to the substrate non-covalently. For example, a biotinylated pSer$^{784}$-VCP antibody may be prepared, which may bind to surfaces covalently coated with streptavidin, resulting in attachment. Alternatively, an antibody may be synthesized on the surface using techniques such as photopolymerization and photolithography.

Contacting the sample with an antibody under effective conditions for a period of time sufficient to allow formation of a complex generally involves adding the pSer$^{784}$-VCP composition to the sample and incubating the mixture for a period of time long enough for the pSer$^{784}$-VCP antibody to bind to any antigen present. After this time, the complex may be washed and then the complex is detected and the amount measured by any method well known in the art. Methods of detecting and measuring an amount of an antibody-polypeptide complex are generally based on the detection of a label or marker. The term "label", as used herein, refers to any substance attached to an antibody, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, streptavidin, protein A, protein G, antibodies or fragments thereof, polyhistidine, Ni$^{2+}$, Flag tags, myc tags, heavy metals, and enzymes (including alkaline phosphatase, peroxidase, glucose oxidase and luciferase). Methods of detecting and measuring an amount of an antibody-polypeptide complex based on the detection of a label or marker are well known in the art.

In some embodiments, an antibody-based method is an immunoassay. Immunoassays can be run in a number of different formats. Generally speaking, immunoassays can be divided into two categories: competitive immunoassays and non-competitive immunoassays. In a competitive immunoassay, an unlabeled analyte in a sample competes with labeled analyte to bind an antibody. Unbound analyte is washed away and the bound analyte is measured. In a non-competitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled). Suitable labels are described above.

In other embodiments, an antibody-based method is an immunoblot or Western blot. In yet other embodiments, an antibody-based method is flow cytometry. In different embodiments, an antibody-based method is immunohistochemistry (IHC). IHC uses an antibody to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

In alternative embodiments, an antibody-based method is an array. An array comprises at least one address, wherein at least one address of the array has disposed thereon a pSer$^{784}$-VCP antibody. Arrays may comprise from about 1 to about several hundred thousand addresses. Several substrates suitable for the construction of arrays are known in the art, and one skilled in the art will appreciate that other substrates may become available as the art progresses. Suitable substrates are also described above. In some embodiments, the array comprises at least one anti-pSer$^{784}$-VCP antibody attached to the substrate is located at one or more spatially defined addresses of the array. For example, an array may comprise at least one, at least two, at least three, at least four, or at least five pSer$^{784}$-VCP antibodies, each antibody recognizing the same or different epitope, and each antibody may be may be at one, two, three, four, five, six, seven, eight, nine, ten or more spatially defined addresses.

For each of the foregoing embodiments, a VCP polypeptide may be first isolated or enriched before detection. For instance, a VCP polypeptide may be enriched or isolated using liquid chromatography, by precipitation, electrophoresis, or affinity purification. In some embodiments, a VCP polypeptide may be enriched or purified using liquid chromatography. In other embodiments, a VCP polypeptide may be enriched or purified using electrophoresis.

In an embodiment, a VCP polypeptide may be enriched or purified by affinity purification before detection. In another embodiment, a VCP polypeptide may be enriched or purified by affinity purification using an antibody of the invention. Methods of enriching a sample for a protein or purifying a protein using affinity purification are known in the art. In short, affinity purification comprises incubating a sample with a solid support, such as beads, a culture plate, or a membrane, that facilitates later steps. A solid support may be coated with an antibody of the invention, causing a VCP polypeptide to attach to the solid support. Alternatively, a sample may be incubated with an antibody of the invention, and the VCP-antibody complex may be isolated by incubating with a solid support coated with a second antibody with specificity to an antibody of the invention, causing a protein-antibody complex to attach to the solid support. A VCP polypeptide may then be purified or enriched by washing other material in the sample that is not bound to the solid support, or, if the solid support is superparamagnetic beads, a VCP polypeptide attached to the beads (expressing the antigen) may be separated from the sample by attraction to a strong magnetic field. Upon enrichment or purification, an VCP polypeptide may then be detected in the enriched or purified sample using any of the methods described above.

The below examples disclose a sensitive method using a pSer$^{784}$-VCP antibody quantify the abundance of VCP phosphorylation within immuno-based techniques, such as, immunohistochemistry and immunoblotting. However, the present disclosure is not limited to any one particular method to quantitatively assess VCP Ser$^{784}$ phosphorylation. Suitable methods include other epitope binding agent-based methods, such as ELISA or other quantitative methods such as mass spectrometry. Other methods known in the art may also be used. In some embodiments, the methods include a pSer$^{784}$-VCP antibody of the disclosure. Suitable pSer$^{784}$-VCP antibodies are discussed in Section II and incorporated into this section by reference.

IV. Methods for Assessing Responsiveness to a Genotoxic Therapy

As shown in the below examples, the level of phosphorylation of VCP at Ser$^{784}$ can be used as a predictive marker to select subjects who can benefit from genotoxic therapies or subject who can benefit from sensitization by PIKK inhibitors. For example, the level of phosphorylation of VCP at Ser$^{784}$ of a candidate subject can be compared with a reference value.

A reference value may represent the same level of phosphorylation of VCP at Ser$^{784}$ of a control subject or represent the level of phosphorylation of VCP at Ser$^{784}$ of a control population. In some examples, the same level of phosphorylation of VCP at $Ser^{784}$ of a control subject or a control population may be determined by the same method as used for determining the level of phosphorylation of VCP at $Ser^{784}$ of the candidate subject. In some instances, the control subject or control population may be a subject having cancer or a tumor or a subject population having cancer or a tumor who is responsive to a genotoxic therapy. In other instances, the control subject or control population may be a subject having cancer or a tumor or a subject population having cancer or a tumor who is non-responsive to a genotoxic therapy. Alternatively, the control subject or control population may refer to a healthy subject or healthy subject population. In a preferred embodiment, the control subject or control population is of the same species (e.g., a human subject or human subject population) as the candidate subject. As used herein, assessing "responsiveness" or "non-responsiveness" to a genotoxic therapy refers to the determination of the likelihood of a subject for responding or not responding to the genotoxic agent. For example, a responsive subject will have a therapeutic effect as a result of administration of a genotoxic agent. In some embodiments, a therapeutic effect includes to prevent or slow down (lessen) an undesired physiological change or disease/disorder. Beneficial or desired clinical results include, but are not limited to, alleviation of symptoms, diminishment of extent of disease, stabilized (i.e., not worsening) state of disease, a delay or slowing of disease progression, amelioration or palliation of the disease state, and remission (whether partial or total), or can also mean prolonging survival as compared to expected survival if not receiving treatment or a non-responsive subject or population.

As used herein, the term "genotoxic therapy" refers to the treatment of cancer or tumor cell by utilizing the destructive properties of the genotoxic agent to induce DNA damage with the genome of the cancer or tumor cell. In some instances, as a result of the DNA damage, the cancer or tumor cell will undergo apoptosis. Comet assays are one of the most common tests for genotoxicity. The technique involves lysing cells using detergents and salts. The DNA released from the lysed cell is electrophoresed in an agarose gel under neutral pH conditions. Cells containing DNA with an increased number of double-strand breaks will migrate more quickly to the anode. Non-limiting examples of genotoxic therapies include alkylating agents, platinum drugs, antimetabolites, topoisomerase inhibitors, photodynamic therapies, reactive oxygen species, and ionizing radiation. Specific examples include but are not limited to cyclophosphamide, methotrexate, anthracycline hydroxyurea (HU), 5-fluorouracil (5FU), cisplatin, and gemcitabine.

It is to be understood that the methods provided herein do not require that a reference value be measured every time a candidate subject is tested. Rather, in some embodiments, it is contemplated that the reference value can be obtained and recorded and that any test level can be compared to such a reference level. The reference level may be a single-cutoff value or a range of values.

By comparing level of phosphorylation of VCP at $Ser^{784}$ in a candidate subject as disclosed herein with a reference value as also described herein, the subject can be identified as responsive or likely to be responsive or as not responsive or not likely to be responsive to a genotoxic therapy based on the assessing.

For example, when the reference value represents the level of phosphorylation of VCP at $Ser^{784}$ who are responsive to a genotoxic therapy, derivation from such a reference value would indicate non-responsiveness to the therapy. In an exemplary embodiment, when the reference value represents level of phosphorylation of VCP at $Ser^{784}$ who are responsive to a therapy, an elevated level of phosphorylation of VCP at $Ser^{784}$ in a candidate subject indicates the subject would be non-responsive to a genotoxic therapy. In another embodiment, when the reference value represents the level of phosphorylation of VCP at $Ser^{784}$ who are responsive to a genotoxic therapy, about the same level of phosphorylation of VCP at $Ser^{784}$ in a candidate subject would indicate responsiveness to the therapy.

Alternatively, when the reference value represents the level of phosphorylation of VCP at $Ser^{784}$ who are non-responsive to a genotoxic therapy, derivation from such a reference value would indicate responsiveness to the therapy. In an exemplary embodiment, when the reference value represents level of phosphorylation of VCP at $Ser^{784}$ who are non-responsive to a therapy, a reduced level of phosphorylation of VCP at $Ser^{784}$ in a candidate subject indicates the subject would be responsive to a genotoxic therapy. In another embodiment, when the reference value represents the level of phosphorylation of VCP at $Ser^{784}$ who are non-responsive to a genotoxic therapy, about the same level of phosphorylation of VCP at $Ser^{784}$ in a candidate subject would indicate non-responsiveness to the therapy.

In some instances, derivation means that the level of phosphorylation of VCP at $Ser^{784}$ (e.g., represented by a value) of a candidate subject is elevated or reduced as relative to a reference value, for example, by at least 5%, 10%, 20%, 30%, 40%, 50%, 60%, 70%, 80%, 90%, 100%, 150%, 200%, 300%, 400%, 500% or more above or below the reference value.

Thus, the present disclosure provides a method for assessing responsiveness to a genotoxic therapy in a subject having a cancer or tumor. In one embodiment, a method for assessing responsiveness to a genotoxic therapy may comprises (a) providing a biological sample obtained from a subject and measuring, in the cancer cell or tumor cell of the sample, the level of VCP phosphorylation at $Ser^{784}$; and (b) determining the subjects responsiveness to the genotoxic therapy when the measured phosphorylation level deviates from a reference value.

In another embodiment, a method for assessing responsiveness to a genotoxic therapy may comprises (a) providing a biological sample obtained from a subject who was treated with a genotoxic agent before the sample was obtained and measuring, in the cancer cell or tumor cell of the sample, the level of VCP phosphorylation at Ser784; and determining the subjects responsiveness to the genotoxic therapy when the measured phosphorylation level deviates from a reference value. Such a method allows for the measurement of induced levels of VCP phosphorylation at $Ser^{784}$.

VCP-$Ser^{784}$-phosphorylation levels may be used in various mathematical operations to assess responsiveness. For instance, VCP-$Ser^{784}$-phosphorylation values can be used in various statistical models (e.g., linear regressions, LME curves, LOESS curves, etc.) in conjunction with other known biomarkers. Selection of measurements and choice of mathematical operations may be optimized to maximize specificity of the method. For instance, diagnostic accuracy may be evaluated by area under the ROC curve and in some embodiments, an ROC AUC value of 0.7 or greater is set as a threshold (e.g., 0.7, 0.75, 0.8, 0.85, 0.9, 0.95, etc.).

Methods for measuring VCP-$Ser^{784}$-phosphorylation levels are described in Section III and incorporated into this section by reference. For instance, using the protocol detailed for Example 1 VCP-$Ser^{784}$-phosphorylation levels in genotoxic responsive and non-responsive were measured by immunoblotting and immunostaining of cells and tissues.

A subject of the disclosure may be a subject having a cancer or tumor. Non-limiting examples of cancer or tumor that may be treated with a method of the invention may include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-cell lymphoma (cutaneous), T-cell leukemia and lymphoma, testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, or Wilms tumor (childhood). In an exemplary embodiment, the subject has a breast cancer. In one aspect, the breast cancer is a triple negative breast cancer.

V. Methods of Treatment

Another aspect of the present disclosure is a method for treating a subject in need thereof. The terms "treat," "treating," or "treatment" as used herein, refers to the provision of medical care by a trained and licensed professional to a subject in need thereof. The medical care may be a diagnostic test, a therapeutic treatment, and/or a prophylactic or preventative measure. The object of therapeutic and prophylactic treatments is to prevent or slow down (lessen) an undesired physiological change or disease/disorder. Beneficial or desired clinical results of therapeutic or prophylactic treatments include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the disease, condition, or disorder as well as those prone to have the disease, condition or disorder or those in which the disease, condition or disorder is to be prevented. In some embodiments, a subject receiving treatment may be diagnosed as having a cancer or tumor.

In one embodiment, a method for treating a subject as described above may comprise (a) providing a biological sample obtained from a subject and measuring, in a cancer cell or tumor cell of the sample, the level of VCP phosphorylation at $Ser^{784}$; (b) determining the subjects responsiveness to a genotoxic therapy when the measured phosphorylation level deviates from a reference value; and (c) administering a pharmaceutical composition to the subject as determined by the subject's responsiveness to the genotoxic therapy.

Thus, the present disclosure provides methods of selecting a treatment based on a subject's responsiveness to a genotoxic treatment. In some embodiments, a method of selecting a treatment may comprise (a) providing a biological sample obtained from a subject and measuring, in a cancer cell or tumor cell of the sample, the level of VCP phosphorylation at $Ser^{784}$; (b) determining the subjects responsiveness to a genotoxic therapy when the measured phosphorylation level deviates from a reference value; and (c) administering a pharmaceutical composition comprising a genotoxic agent to the subject when the measured phosphorylation level is reduced relative to the reference value of a control subject or control population who are non-responsive to a genotoxic therapy.

In another embodiment, a method of selecting a treatment may comprise (a) providing a biological sample obtained from a subject and measuring, in a cancer cell or tumor cell of the sample, the level of VCP phosphorylation at $Ser^{784}$; (b) determining the subjects responsiveness to a genotoxic therapy when the measured phosphorylation level deviates from a reference value; and (c) administering a pharmaceutical composition comprising a genotoxic agent to the subject when the measured phosphorylation level is about the same as a reference value of a control subject or control population who are responsive to a genotoxic therapy.

In another embodiments, a method of selecting a treatment may comprise (a) providing a biological sample obtained from a subject and measuring, in a cancer cell or tumor cell of the sample, the level of VCP phosphorylation at $Ser^{784}$; (b) determining the subjects responsiveness to a genotoxic therapy when the measured phosphorylation level deviates from a reference value; and (c) administering a pharmaceutical composition comprising an inhibitor of phosphatidylinositol 3-kinase-related kinases (PIKKs) to the subject when the measured phosphorylation level is elevated relative to a reference value of a control subject or control population who are responsive to a genotoxic therapy. The method may further comprise administering a genotoxic treatment to the subject after or concurrently with the administration of the PIKK inhibitor.

In another embodiments, a method of selecting a treatment may comprise (a) providing a biological sample obtained from a subject and measuring, in a cancer cell or tumor cell of the sample, the level of VCP phosphorylation at $Ser^{784}$; (b) determining the subjects responsiveness to a genotoxic therapy when the measured phosphorylation level deviates from a reference value; and (c) administering a pharmaceutical composition comprising an inhibitor of phosphatidylinositol 3-kinase-related kinases (PIKKs) to the subject when the measured phosphorylation level is about the same as a reference value of a control subject or control population who are non-responsive to a genotoxic therapy. The method may further comprise administering a genotoxic treatment to the subject after or concurrently with the administration of the PIKK inhibitor.

In each of the above embodiments, a pharmaceutical composition may comprise an active pharmaceutical ingredient. Non-limiting examples of active pharmaceutical ingredients include genotoxic agents such as alkylating agents, platinum drugs, antimetabolites, topoisomerase inhibitors, photodynamic therapies, reactive oxygen species, and ionizing radiation. In another alternative, a pharmaceutical composition may comprise an inhibitor of one or more phosphatidylinositol 3-kinase-related kinases (e.g., ATM, ATR, CHEK1, CHEK2, WEE1, and DNA-PKcs). Non-limiting examples include AZD0156, KU-55933, VE-821, AZD6738, VX970, VX-984, MK8776 (SCH900776), LY2603618, CCT245737, GDC-0575, PV1019, CCT241533, AZD7762, ETP-46464, NU6027, BAY-1895344, NSC2490484A (M3814), and AZD1775.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

The concentration of the composition of the present disclosure in the fluid pharmaceutical formulations can vary widely, i.e., from less than about 0.05% usually or at least about 2-10% to as much as 30 to 50% by weight and will be selected primarily by fluid volumes, viscosities, etc., in accordance with the particular mode of administration selected. For example, the concentration may be increased to lower the fluid load associated with treatment. The amount of nanoparticle pharmaceutical composition administered will depend upon the particular therapeutic entity entrapped inside the nanoparticle, the type of nanoparticle being used, and the judgment of the clinician. Generally the amount of nanoparticle pharmaceutical composition administered will be sufficient to deliver a therapeutically effective dose of the particular therapeutic entity.

The quantity of a pharmaceutical composition necessary to deliver a therapeutically effective dose can be determined by routine in vitro and in vivo methods, common in the art of drug testing. See, for example, D. B. Budman, A. H. Calvert, E. K. Rowinsky (editors). Handbook of Anticancer Drug Development, L W W, 2003. Therapeutically effective dosages for various therapeutic entities are well known to those of skill in the art; and according to the present disclosure a therapeutic entity delivered via the pharmaceutical liposome composition of the present invention provides at least the same, or 2-fold, 4-fold, or 10-fold higher activity than the activity obtained by administering the same amount of the therapeutic entity in its routine non-liposome formulation. Typically the dosages for the nanoparticle pharmaceutical composition of the present disclosure range between about 0.005 and about 500 mg of the therapeutic entity per kilogram of body weight, most often, between about 0.1 and about 100 mg therapeutic entity/kg of body weight.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Administration of a composition of the disclosure can occur as a single event or over a time course of treatment. For example, one or more of a nanoparticle composition can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for a cancer or tumor.

The present disclosure encompasses pharmaceutical compositions comprising compounds as disclosed above, so as to facilitate administration and promote stability of the active agent. For example, a compound of this disclosure may be admixed with at least one pharmaceutically acceptable carrier or excipient resulting in a pharmaceutical composition which is capably and effectively administered (given) to a living subject, such as to a suitable subject (i.e. "a subject in need of treatment" or "a subject in need thereof"). For the purposes of the aspects and embodiments of the invention, the subject may be a human or any other animal.

Methods for measuring VCP phosphorylation at $Ser^{784}$ and methods for assessing a subject's responsiveness are described in Section III and Section IV, respectively, and incorporated into this section by reference. In an exemplary embodiment, a protocol outlined in the Examples is used.

VI. Clinical Trials

Another aspect of the present disclosure is a method for enrolling a subject into a clinical trial, in particular a clinical trial for an genotoxic or PIKK inhibitor therapy, provided all other criteria for the clinical trial have been met. In one embodiment, a method for a method for enrolling a subject into a clinical trial may comprise (a) providing a biological sample obtained from a subject and measuring, in a cancer cell or tumor cell of the sample, the level of VCP phosphorylation at $Ser^{784}$; and (b) enrolling the subjects the subject into a clinical trial when the measured phosphorylation level deviates from a reference value.

The design of clinical trials for cancer or tumor therapies can be greatly aided by the methods disclosed herein. Many clinical trials are designed to test the efficacy of therapeutic agents that cause DNA damage or inhibit PIKKs. As discussed herein, the efficacy of these various agents can be improved by administering the agents to subjects that have certain levels of VCP phosphorylation at $Ser^{784}$, as measured by methods disclosed herein and illustrated. Accordingly, measuring VCP-$Ser^{784}$ phosphorylation levels as described herein prior to enrolling a subject in a clinical trial, in particular into a treatment arm of a clinical trial, may result in smaller trials and/or improved outcomes. In some instances, methods described herein may be developed and used as a companion diagnostic for a therapeutic agent.

In each of the above embodiments, a subject may be enrolled into a treatment arm of the clinical trial. The "treatment" is defined in Section V. Subjects enrolled in the treatment arm of a clinical trial may be administered a pharmaceutical composition. In some embodiments, a pharmaceutical composition may comprise a genotoxic agent. In some embodiments, a pharmaceutical composition may comprise a PIKK inhibitor.

VII. KITS

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to polyclonal and monoclonal antibodies of $pSer^{784}$-VCP. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium or video. Detailed instructions may not be physically associated with the kit; instead, a user may be directed to an Internet web site specified by the manufacturer or distributor of the kit.

A control sample or a reference sample as described herein can be a sample from a healthy subject. A reference value can be used in place of a control or reference sample, which was previously obtained from a healthy subject or a group of healthy subjects. A control sample or a reference sample can also be a sample with a known amount of a detectable compound or a spiked sample. A control sample or a reference sample can also be from a genotoxic treatment responsive subject or population. A control sample or a reference sample can also be from a genotoxic treatment non-responsive subject or population.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10:0879697717; Ausubel et al. (2002) Short Protocols in Molecular Biology, 5th ed., Current Protocols, ISBN-10:0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41 (1), 207-234; Gellissen, ed. (2005) Production of Recombinant Proteins: Novel Microbial and Eukaryotic Expression Systems, Wiley-VCH, ISBN-10:3527310363; Baneyx (2004) Protein Expression Technologies, Taylor & Francis, ISBN-10:0954523253).

Specific embodiments disclosed herein may be further limited in the claims using "consisting of" or "consisting essentially of" language, rather than "comprising". When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As various changes could be made in the above-described materials and methods without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Phospho-Ser$^{784}$-VCP is Required for DNA Damage Response and is Associated with Poor Prognosis of Chemotherapy-Treated Breast Cancer Spatiotemporal protein reorganization at DNA damage sites induced by genotoxic chemotherapies is crucial for DNA damage response (DDR), which influences treatment response by directing cancer cell fate. This process is orchestrated by valosin-containing protein (VCP), an AAA+ ATPase that extracts polyubiquinated chromatin proteins and facilitates their turnover. However, because of the essential and pleiotropic effects of VCP in global proteostasis, it remains challenging practically to understand and target its DDR-specific functions. The present example establishes a DNA-damage-induced phosphorylation event (Ser$^{784}$), which selectively enhances chromatin-associated protein degradation mediated by VCP and is required for DNA repair, signaling, and cell survival. These functional effects of Ser$^{784}$ phosphorylation on DDR correlate with a decrease in VCP association with chromatin, cofactors NPL4/UFD1, and polyubiquitinated substrates. As shown herein, high phospho-Ser$^{784}$-VCP levels are significantly associated with poor clinical outcomes among chemotherapy-treated breast cancer patients. Thus, Ser$^{784}$ phosphorylation is a DDR-specific enhancer of VCP function and a predictive biomarker for genotoxic treatments.

Figure 2A:
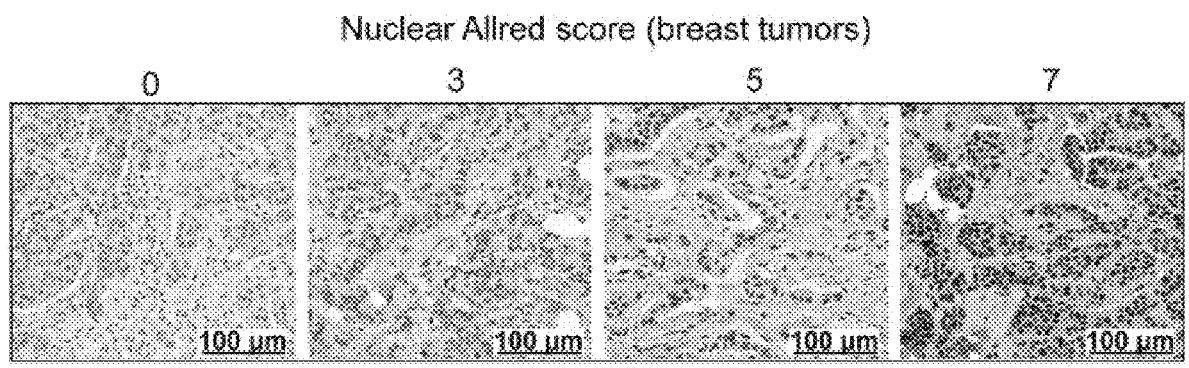
FIG. 2A-2E show nuclear antigen recognized by the $pSer^{137}$-Pfn1 antibody associates with poor survival among chemotherapy-treated breast cancer patients.
Figure 2B:
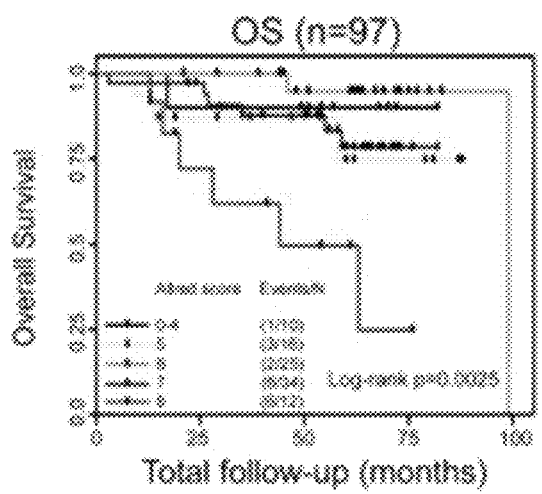
Figure 2B:
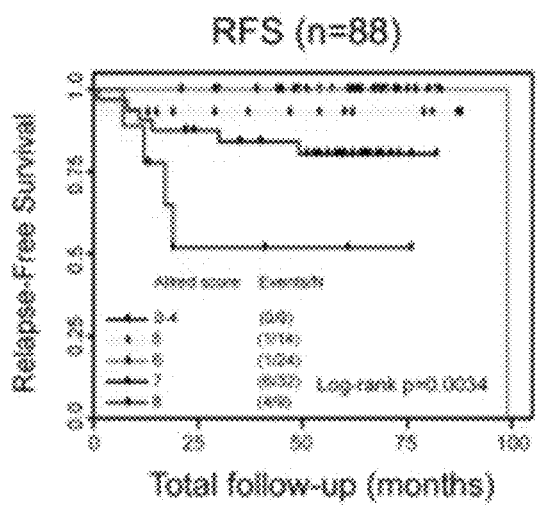
Figure 2C:
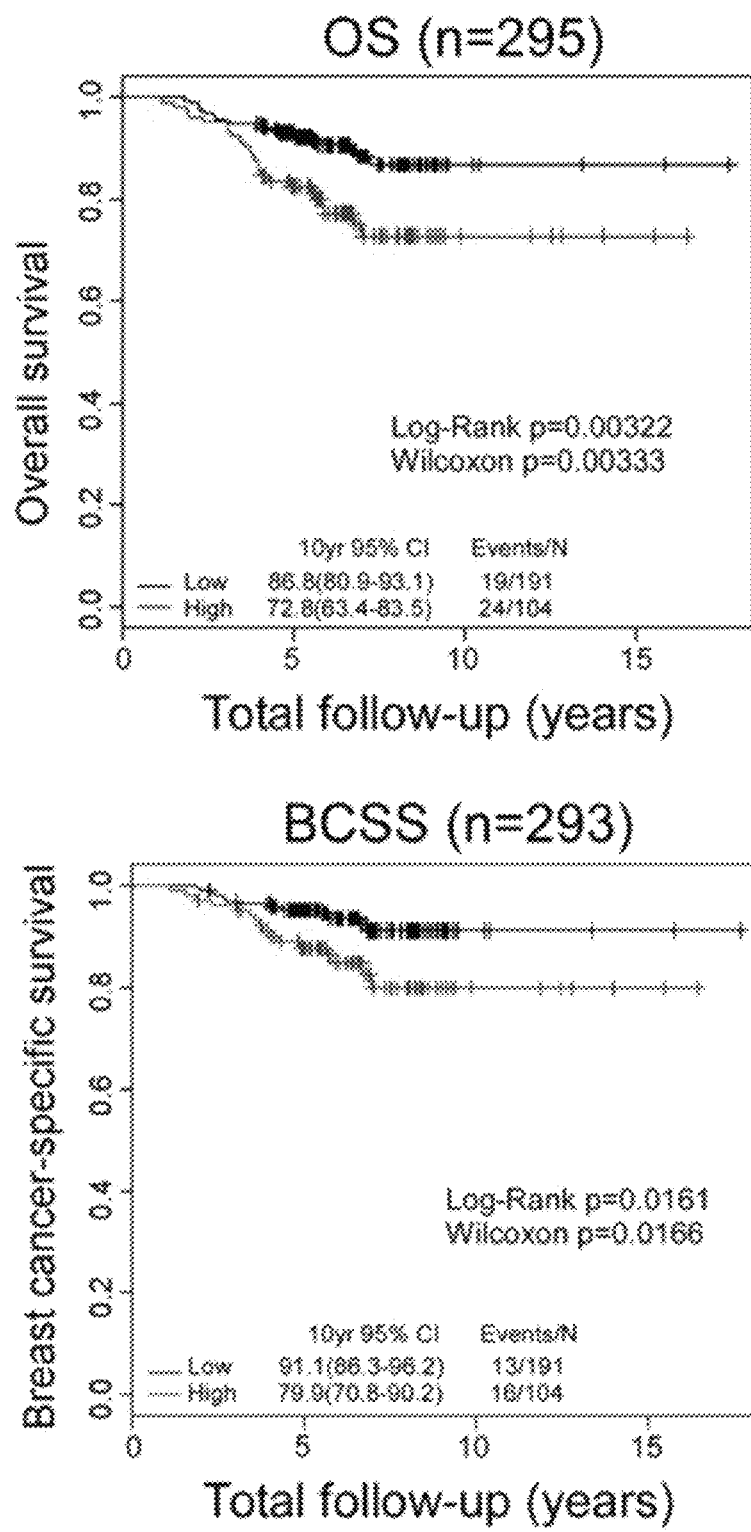
Figure 3A:
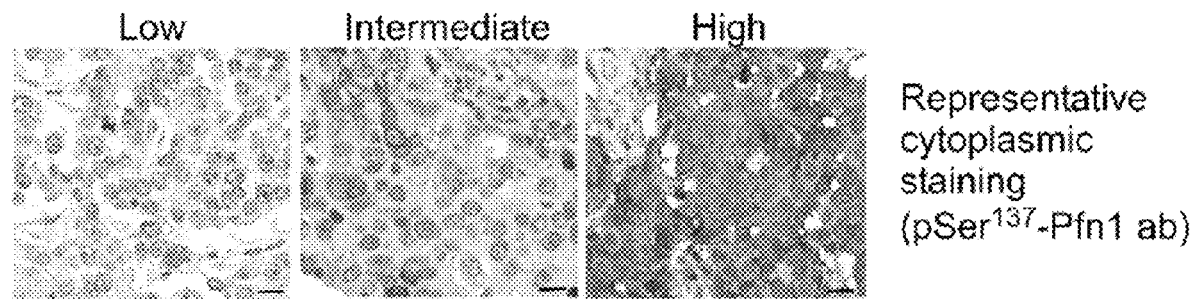
FIG. 3A-3E show nuclear antigen recognized by the $pSer^{137}$-Pfn1 antibody inversely correlates with breast cancer survival in the UBC series, related to FIG. 2C and FIG. 2D.
Figure 3B:
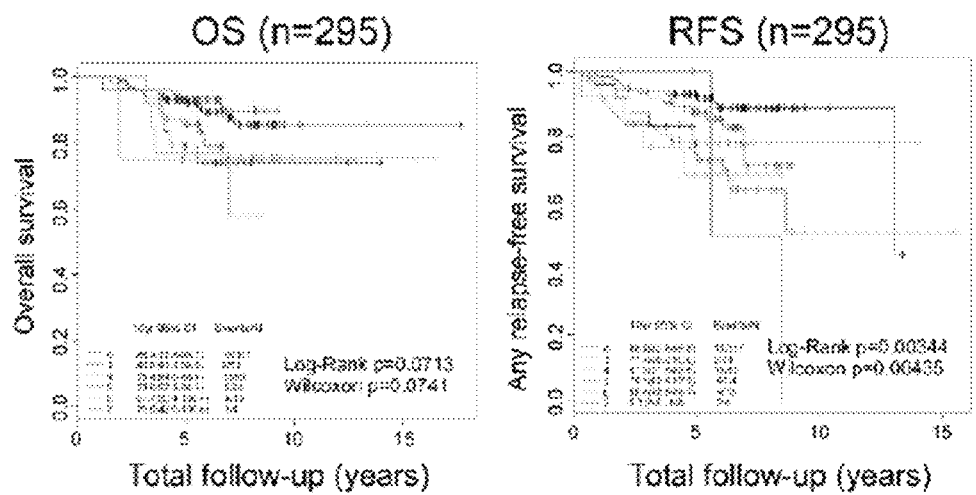
Figure 3C:
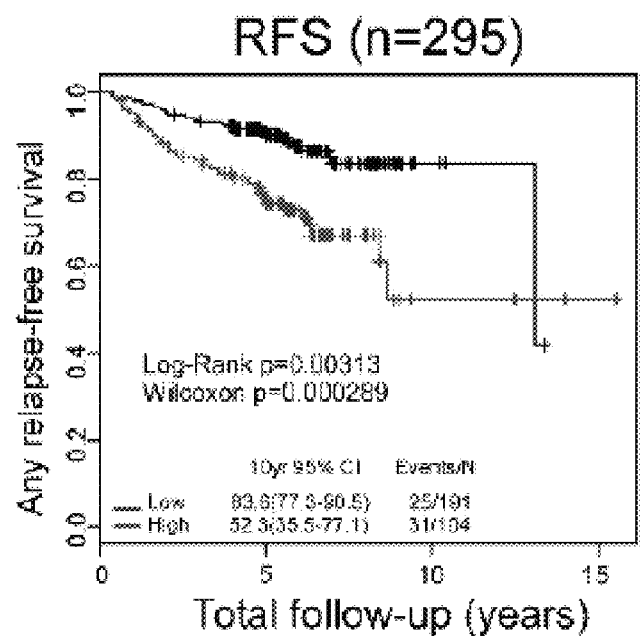
Figure 3D:
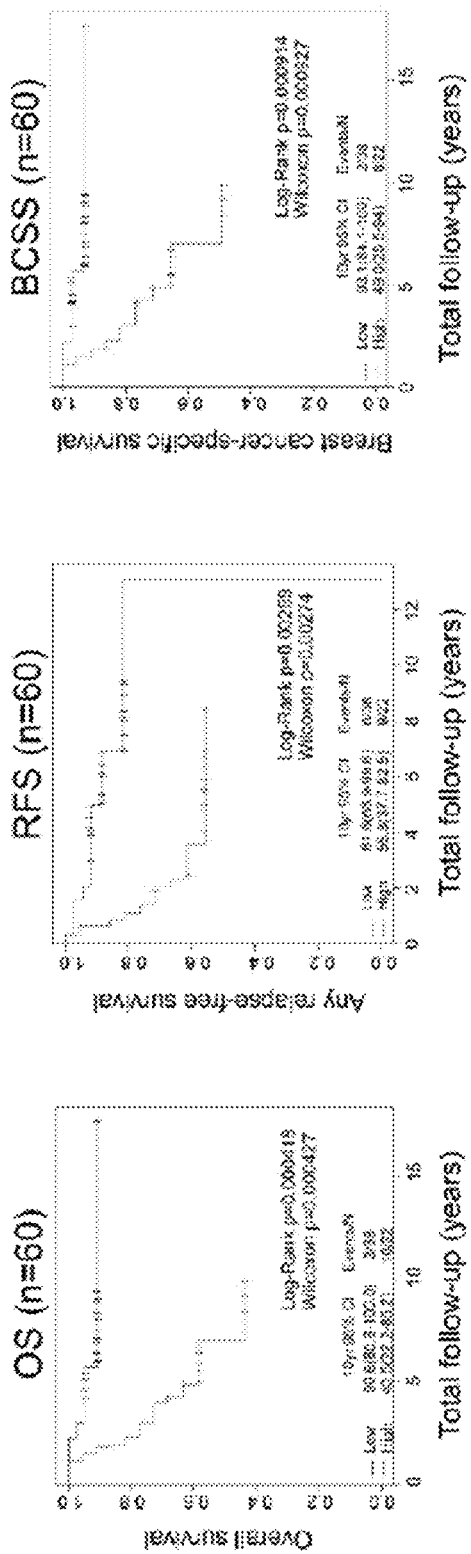
Figure 3D:
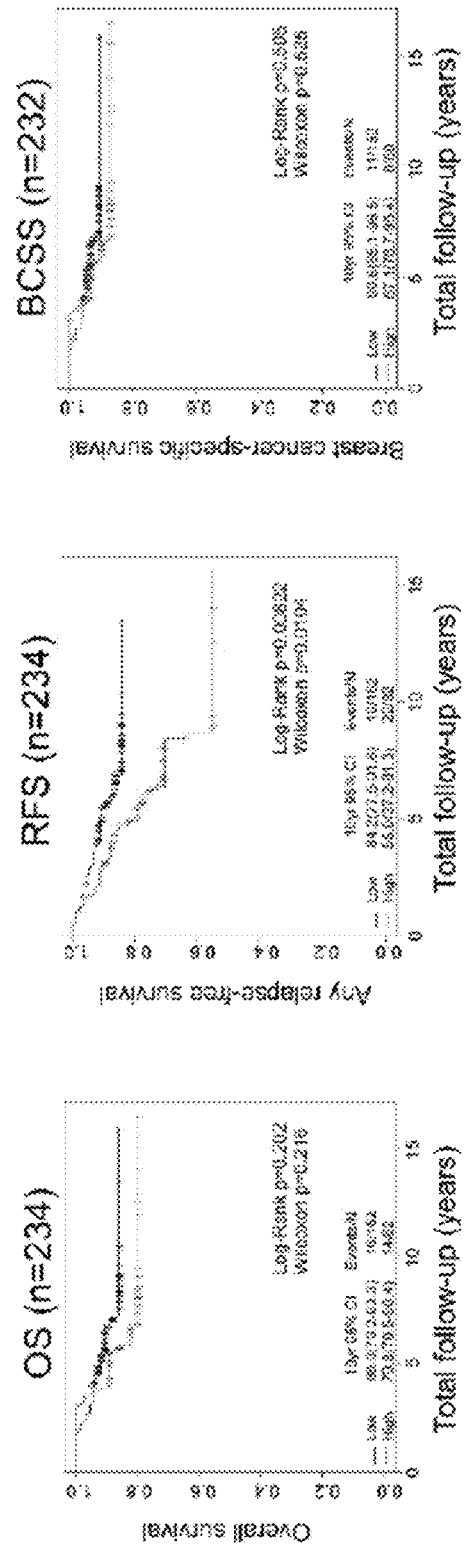
Figure 3E:
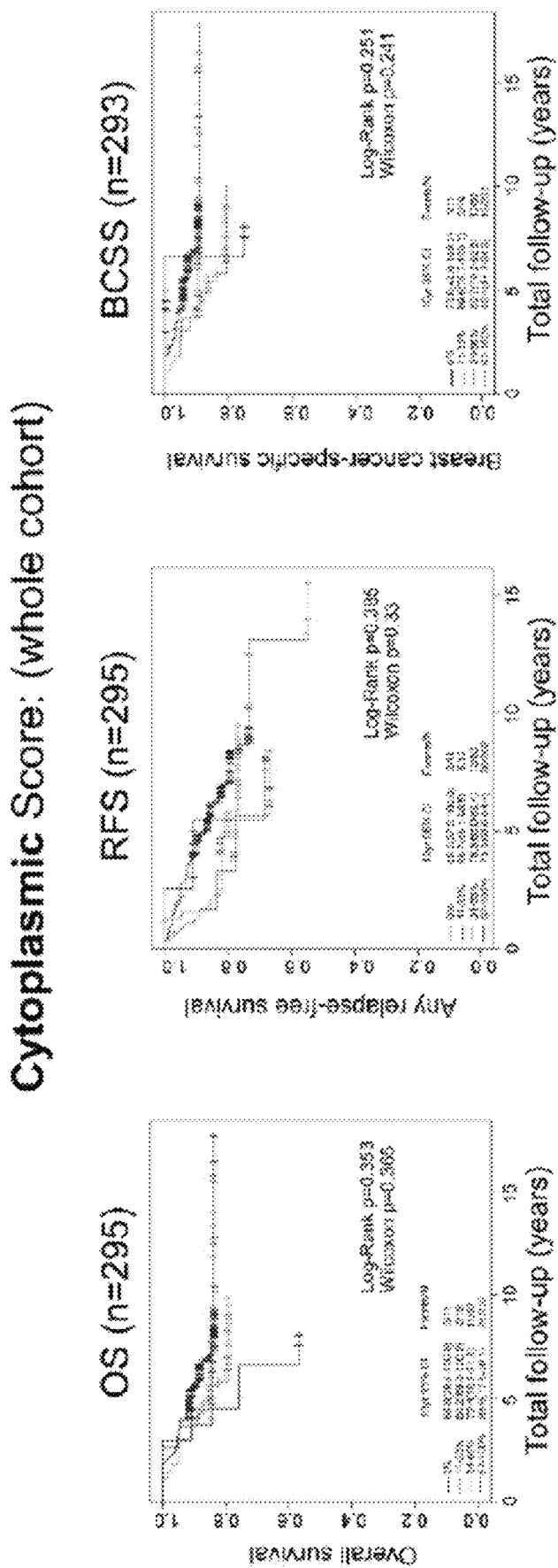

Results:

Nuclear Antigen Recognized by the pSer$^{137}$-Pfn1 Antibody Associates with Poor Survival on Chemotherapy in Breast Cancer: A polyclonal antibody targeting phospho-Ser$^{137}$ of the actin-binding factor profilin-1 (Pfn1) was previously generated. Using that antibody to stain a few breast cancer samples, positive signals in a subset of cases were observed. However, both the intensity and the subcellular location of the signals varied (FIG. 1A and FIG. 2A). Intrigued by the nuclear staining because of interest in nuclear Pfn1 functions, a clinically annotated invasive breast cancer tissue microarray (TMA) were stained (Strategic Partnering to Evaluate Cancer Signatures [SPECS]) and scored the nuclear signals using the Allred method (intensity+proportion). Univariate survival analysis revealed an inverse and statistically significant correlation between the individual nuclear Allred scores and clinical outcomes of overall survival (OS) (n=97, p=0.0025) and relapse-free survival (RFS) (n=88, p=0.0034) by the log-rank test (F 1B). To confirm that result, a larger and independent breast cancer TMA (UBC series) was stained. Similar results were observed, namely that high individual nuclear Allred scores were significantly associated with a lower RFS (n=295, p=0.0034) and trended toward a lower OS (n=295, p=0.071) (Table 1; FIG. 3B). To simplify the analysis, the nuclear Allred scores were binarized into low (0-3) (n=191, 65%) versus high (4-8) (n=104, 35%) subgroups (Table 2). No significant association was observed between nuclear Allred scores and patient age at diagnosis, tumor size, nodal status, or ER, PR, HER2, or Ki67 status in this dataset. However, there was a significant association between nuclear Allred scores and histologic grade (Table 2). Univariate survival analyses revealed that cases with high Allred scores displayed significantly lower OS (n=295, p=0.0032), RFS (n=295, p=0.0003), and breast-cancer-specific survival (BCSS) (n=293, p=0.016) (FIGS. 1C and S1C). Multivariate analyses, adjusted for the clinicopathological variables of age, tumor grade and size, lymphovascular invasion, nodal status, and ER, PR, HER2, and Ki67 confirmed these results and revealed that the prognostic value of the nuclear staining is independent of those variables (Tables 3, Table 4, and Table 5). Interestingly, the association of nuclear scores with patient survival was mainly observed in the ER-negative subgroup (FIG. 3D). There was no detectable association between the cytoplasmic staining and survival outcomes (FIG. 3E).

TABLE 1

Distributions of the level of the nuclear antigen of pSer$^{137}$-Pfn1 antibody in the UBC series.

| Allred score | Nuclear Allred scores of the antigen of the pSer$^{137}$-Pfa1 antibody |
|---|---|
| Allred 0 | 117 (39.67%) |
| Allred 2 | 0 (0%) |
| Allred 3 | 74 (25.08%) |
| Allred 4 | 63 (21.35%) |
| Allred 5 | 24 (8.14%) |
| Allred 6 | 13 (4.41%) |
| Allred 7 | 4 (1.35%) |
| Alleed 8 | 0 (0%) |
| Total | 295 |

TABLE 2

Clinicopathologic characteristics of the nuclear antigen of the pSer137-Pfn1 antibody in the UBC series.

| Clinicopathologic characteristic | Alfred score (0-3) (n = 191) | Alfred score (4-8) (n = 104) | Total (n = 295) | P-value |
|---|---|---|---|---|
| Age, years | | | | 0.80 |
| >50 | 19 (15%) | 14 (13%) | 33 (14%) | |
| ≥50 | 111 (85%) | 90 (87%) | 201 (86%) | |
| Tumor Size, cm | | | | 0.55 |
| ≤2 | 19 (11%) | 14 (33%) | 33 (12%) | |
| >2 | 153 (898%) | 90 (87%) | 243 (88%) | |
| Involved lymph nodes | | | | |
| Negative | 128 (67%) | 61 (59%) | 189 (64%) | 0.14 |
| Positive | 62 (33%) | 43 (41%) | 105 (36%) | |
| Tumor grade | | | | 0.02 |
| 1 | 44 (24%) | 11 (11%) | 55 (19%) | |
| 2 | 70 (37%) | 42 (40%) | 112 (38%) | |
| 3 | 74 (39%) | 51 (49%) | 125 (43%) | |
| Lympho-vascular Invasion | | | | 0.16 |
| Negative | 144 (79%) | 72 (71%) | 216 (76%) | |
| Positive | 39 (21%) | 29 (29%) | 68 (24%) | |
| ER Status | | | | 0.81 |
| Negative | 38 (20%) | 22 (21%) | 60 (31%) | |
| Positive | 152 (80%) | 82 (79%) | 134 (69%) | |
| PR Status | | | | 0.20 |
| Negative | 57 (30%) | 39 (38%) | 96 (33%) | |
| Positive | 132 (70%) | 63 (62%) | 197 (67%) | |
| HER2 Status | | | | 0.28 |
| Negative | 176 (95%) | 91 (92%) | 267 (94%) | |
| positive | 9 (5%) | 8 (8%) | 17 (6%) | |
| Ki67 | | | | 0.66 |
| <14% | 111 (59%) | 59 (57%) | 170 (58%) | |
| ≥14% | 76 (41%) | 45 (43%) | 121 (42%) | |
| IHC Subtype | | | | |
| Luminal A | 99 (55%) | 52 (54%) | 151 (54%) | (Luminal A vs, others) = 0.82 |
| Luminal B (high Ki67, HER2−) | 46 (25%) | 24 (24%) | 70 (25%) | (Luminal B vs. others) = 0.94 |
| Luminal B (HER2+) | 4 (2%) | 2 (2%) | 6 (2%) | |
| Her2-Enriched | 5 (3%) | 6 (6%) | 11 (4%) | (Her2-Enriched vs. others) = 0.20 |
| Triple Negative | 27 (15%) | 15 (13%) | 42 (15%) | (Triple Negative vs. others) = 0.90 |
| Basal like | 18 (10%) | 10 (10%) | 28 (10%) | (Basal-like vs. others) = 0.87 |

TABLE 3

Univariate and multivariate analysis of overall survival (OS) for the level of nuclear antigen of pSer$^{137}$-Pfn1 antibody in the UBC series.

Univariate analysis for OS In the UBC series

| | Hazard ratio | Lower (95% CI) | Upper (95% CI) | P-value |
|---|---|---|---|---|
| pSer$^{137}$-Pfn1 (nuclear) | 2.4 | 1.3 | 4.4 | <0.01 |

Multivariate analysis for OS in the UBC series

| | Hazard ratio | Lower (95% CI) | Upper (95% CI) | P-value |
|---|---|---|---|---|
| pSer$^{137}$-Pfn1 (nuclear) | 2.51 | 1.31 | 4.83 | <0.01 |
| Age | 1.06 | 1.03 | 1.09 | <0.01 |
| Tumor grade | 1.29 | 0.60 | 2.80 | 0.05 |
| Nodal status | 1.15 | 0.54 | 2.45 | 0.07 |
| Tumor size | 1.46 | 1.19 | 1.80 | <0.01 |
| Lympho-vascular invasion | 2.82 | 1.37 | 5.82 | <0.01 |
| ER status | 0.92 | 0.33 | 2.57 | 0.09 |
| PR status | 0.61 | 0.27 | 1.42 | 0.03 |
| HER2 status | 1.57 | 0.49 | 5.08 | 0.05 |

TABLE 4

Univariate and multivariate analysis of breast cancer specific survival (BCSS) for the level of nuclear antigen of pSer137-Pfn1 antibody in the UBC series.

Univariate analysis for BCSS in the UBC series

| | Hazard ratio | Lower (95% CI) | Upper (95% CI) | P-value |
|---|---|---|---|---|
| pSer$^{137}$-Pfn1 (nuclear) | 2.39 | 1.15 | 4.97 | <0.01 |

Multivariate analysis for BCSS in the UBC series

| | Hazard ratio | Lower (95% CI) | Upper (95% CI) | P-value |
|---|---|---|---|---|
| pSer$^{137}$-Pfn1 (nuclear) | 2.30 | 1.03 | 5.10 | <0.01 |
| Age | 1.02 | 0.99 | 1.06 | 0.02 |
| Tumor grade | 1.70 | 0.68 | 4.25 | 0.03 |
| Nodal status | 1.56 | 0.60 | 4.07 | 0.04 |
| Tumor size | 1.58 | 1.27 | 1.98 | <0.01 |
| Lympho-vascular invasion | 2.93 | 1.20 | 7.15 | <0.01 |
| ER status | 1.04 | 0.32 | 3.32 | 0.09 |
| PR status | 0.58 | 0.21 | 1.59 | 0.03 |
| HER2 status | 1.46 | 0.38 | 5.60 | 0.06 |

TABLE 5

Univariate and multivariate analysis of relapse free survival (RFS) for the level of nuclear antigen of pSer137-Pfn1 antibody in the UBC series.

Univariate analysis for RFS in the UBC series

| | Hazard ratio | Lower (95% CI) | Upper (95% CI) | P-value |
|---|---|---|---|---|
| pSer$^{137}$-Pfn1 (nuclear) | 2.55 | 1.51 | 4.33 | <0.01 |

Multivariate analysis for RFS in the UBC series

| | Hazard radio | Lower (95% CI) | Upper (95% CI) | P-value |
|---|---|---|---|---|
| pSer$^{137}$-Pfn1 (nuclear) | 2.30 | 1.31 | 4.04 | <0.01 |
| Age | 1.00 | 0.98 | 1.03 | 0.08 |
| Tumor grade | 1.13 | 0.61 | 2.10 | 0.07 |

TABLE 5-continued

| | | | | |
|---|---|---|---|---|
| Nodal status | 1.19 | 0.62 | 2.29 | 0.06 |
| Tumor size | 1.29 | 1.09 | 1.52 | <0.01 |
| Lympho-vascular invasion | 2.10 | 1.09 | 4.06 | <0.01 |
| ER status | 0.95 | 0.38 | 2.33 | 0.09 |
| PR status | 0.73 | 0.34 | 1.56 | 0.04 |
| HER2 status | 1.49 | 0.54 | 4.12 | 0.04 |

Figure 2D:
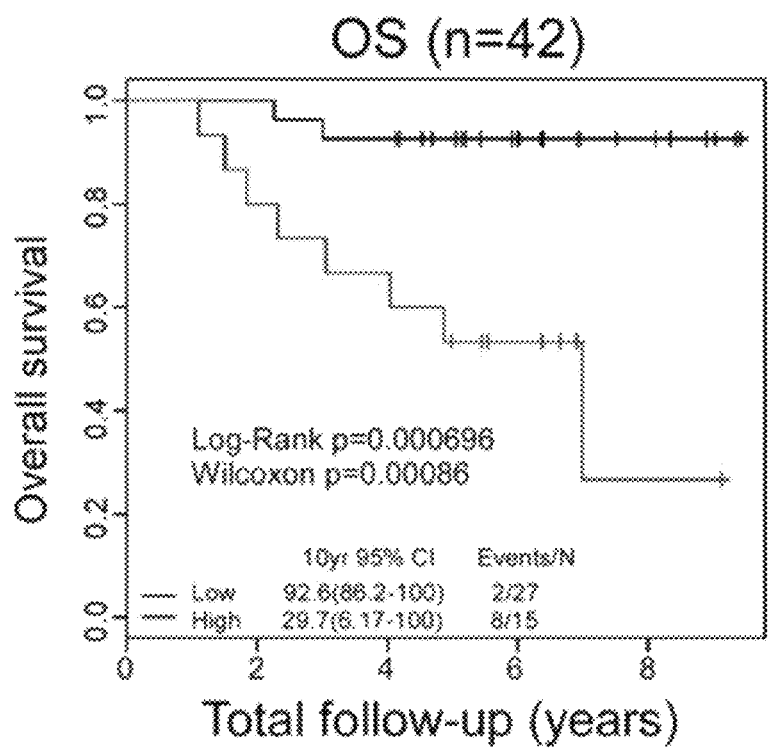
Figure 2D:
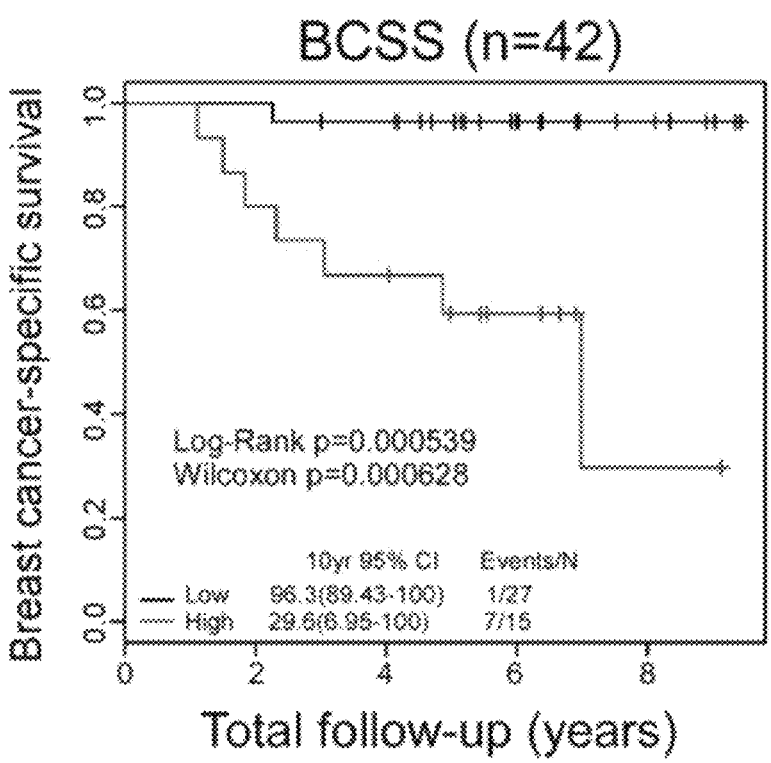
Figure 2E:
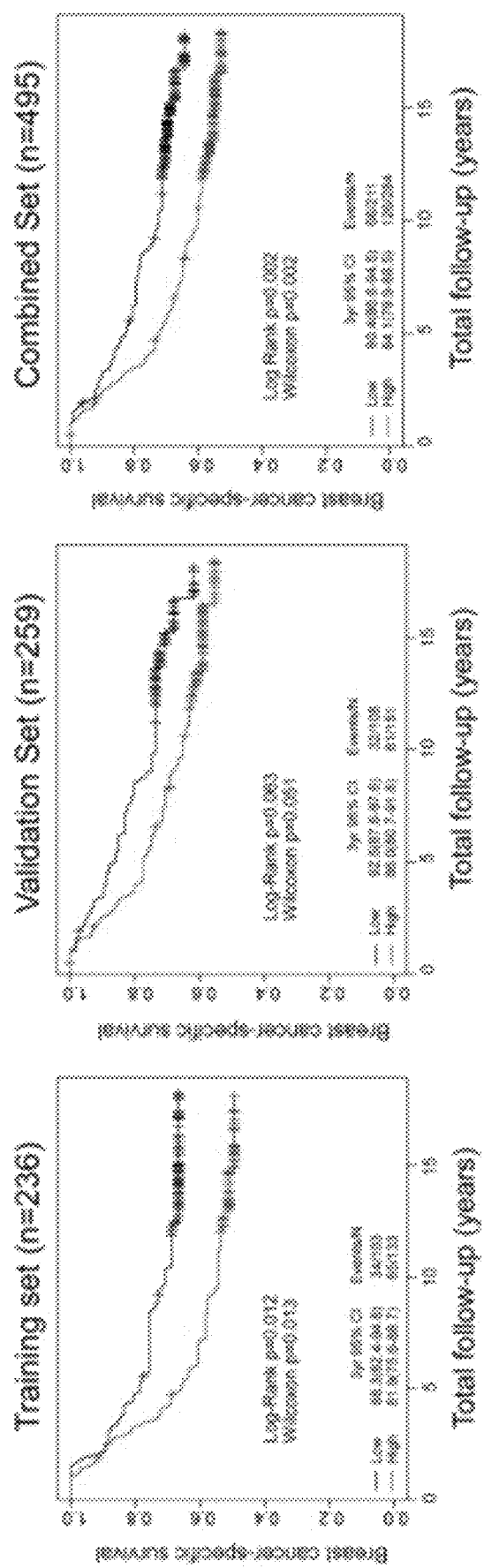
Figure 4A:
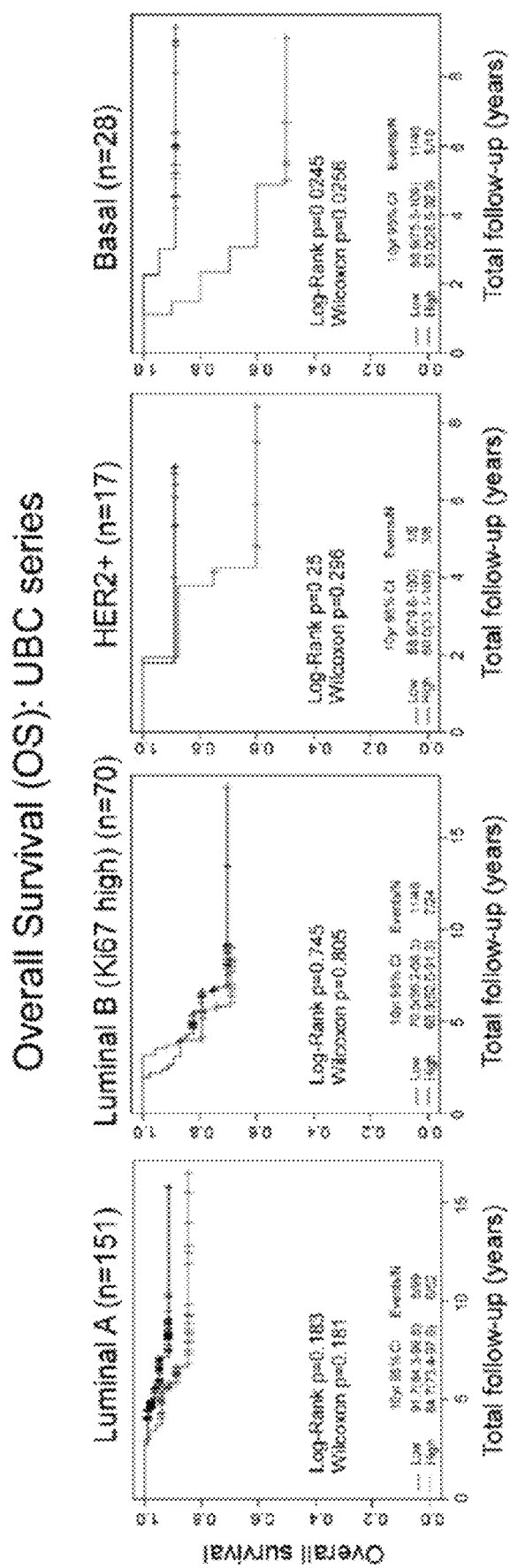
FIG. 4A-4C show the association between the nuclear antigen recognized by the $pSer^{137}$-Pfn1 antibody and breast cancer survival according to IHC subtype in the UBC series. The UBC series was divided into different breast cancer subtypes (luminal A, luminal B, HER2+, and basal) as previously described. Luminal A: ER+ and/or PR+, HER2−, and ki67<14%; luminal B: ER+ and/or PR+, HER2−, and ki67>14% or ER+ and/or PR+, any ki67 and HER2+; HER2+: ER−, PR−, HER2+; triple negative: ER−, PR−, HER2−; basal-like: ER−, PR, HER2− and [EGFR+ or CK5+].
Figure 4B:
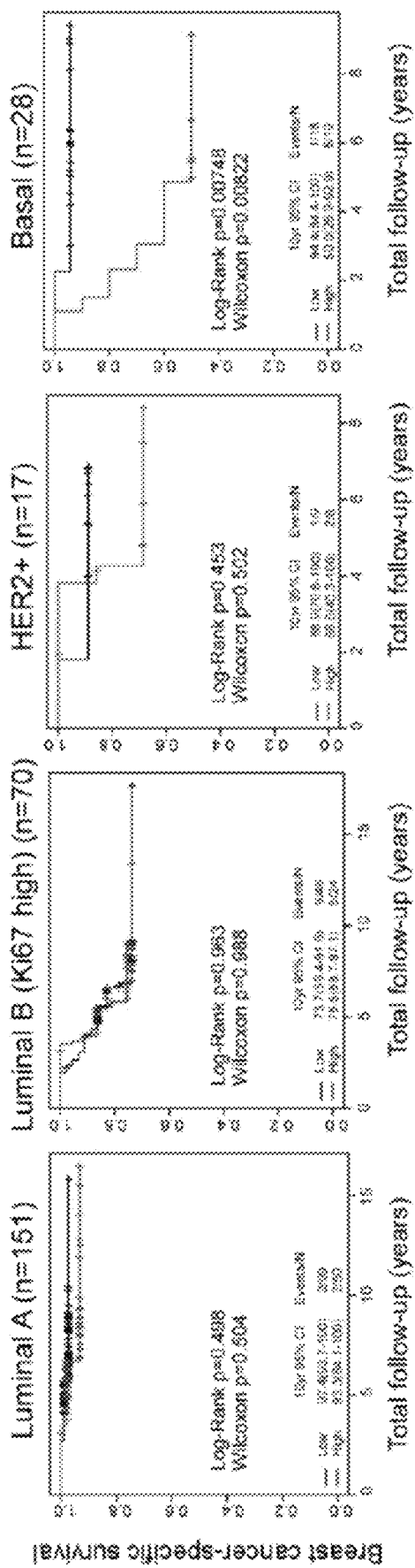
Figure 4C:
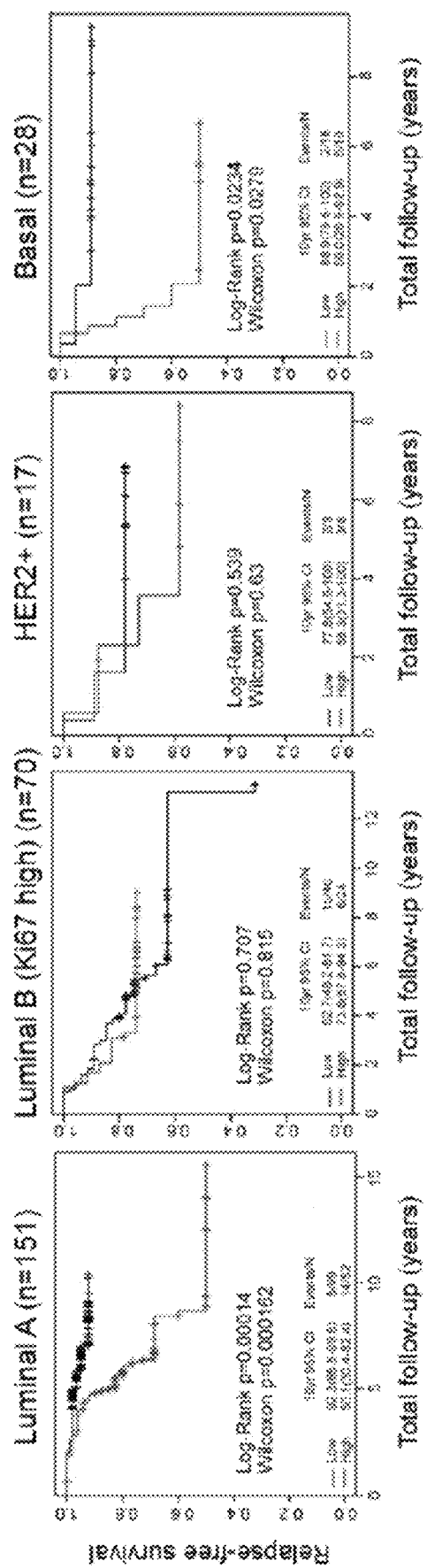

To further investigate the potential clinical relevance of nuclear staining by the pSer[137]-Pfn1 antibody, its association with survival outcomes across the major immunohistochemical subtypes of breast cancer were evaluated. A significant association between nuclear scores and survival was only detected in those with triple-negative breast cancer (TNBC: n=42; OS, p=0.0007; BCSS, p=0.0005; OS-adjusted p=0.003; BCSS-adjusted p=0.002) and basal cases (n=28; OS, p=0.02; BCSS, p=0.007; OS-adjusted p=0.10; BCSS-adjusted p=0.03) (FIG. 2D, FIG. 4A, and FIG. 4B), although a significant correlation with RFS was also detected in luminal A cases (n=151; p=0.0001; adjusted p=0.0006) (FIG. 4C). No significant correlation with survival was observed in luminal B and HER2+ tumors (FIG. 4A-4C).

To investigate these observations according to treatment, the pSer[137]-Pfn1 antibody was used to stain a third and substantially larger breast cancer TMA (BCCancer series). This dataset was split into training and validation sets, each constituting approximately 50% of the total cases. The distribution of nuclear Allred scores in the training set of the BCCancer series, compared with the UBC series, showed a shift to higher levels, possibly because they had been snap frozen before fixation (Table 6). Thus, the binarization method was modified to retain a comparable number of cases in the "low (0-4)" versus "high (5-8)" nuclear score groups and thereby maximize study power in the validation set. A statistically significant association between high nuclear scores and multiple poor prognostic factors, including high grade, ER negativity, HER2 positivity, non-luminal subtype, and triple-negative phenotype was detected (Table 7, Table 8, and Table 9).

TABLE 7

Clinicopathologic characteristics of the nuclear antigen of the pSer[137]-Pfn1 antibody in the training set of the BCCancer series.

| Clinicopathologic characteristic | Nuclear p-PFN1 Allred score (0-4) (n = 515) | Nuclear p-PFN1 Allred score (5-8) (n = 796) | Total (n = 1311) | P-value |
|---|---|---|---|---|
| Age, years | | | | 0.66 |
| <50 | 147 (29%) | 218 (27%) | 365 (28%) | |
| ≥50 | 368 (71%) | 578 (73%) | 946 (72%) | |
| Tumor Size, cm | | | | 0.04 |
| ≤2 | 281 (55%) | 387 (49%) | 668 (51%) | |
| >2 | 232 (45%) | 406 (51%) | 638 (49%) | |
| Involved lymph nodes | | | | 0.43 |
| Negative | 267 (54%) | 433 (57%) | 700 (56%) | |
| 1-3 | 142 (29%) | 218 (29%) | 360 (29%) | |
| 4-9 | 66 (13%) | 79 (11%) | 145 (12%) | |
| ≥10 | 17 (4%) | 25 (3%) | 42 (3%) | |
| Stage | | | | 0.36 |
| I | 186 (36%) | 264 (33%) | 450 (34%) | |
| II | 295 (58%) | 473 (60%) | 768 (59%) | |
| II | 30 (6%) | 58 (7%) | 88 (7%) | |

TABLE 7-continued

Clinicopathologic characteristics of the nuclear antigen of the pSer[137]-Pfn1 antibody in the training set of the BCCancer series.

| Clinicopathologic characteristic | Nuclear p-PFN1 Allred score (0-4) (n = 515) | Nuclear p-PFN1 Allred score (5-8) (n = 796) | Total (n = 1311) | P-value |
|---|---|---|---|---|
| Tumor grade | | | | 0.002 |
| 1-2 | 256 (52%) | 331 (43%) | 578 (46%) | |
| 3 | 233 (48%) | 435 (57%) | 668 (54%) | |
| Lympho-vascular | | | | 1.00 |
| Negative | 273 (55%) | 421 (55%) | 556 (44%) | |
| Positive | 219 (45%) | 337 (45%) | 694 (56%) | |
| ER Status | | | | 0.02 |
| Negative | 121 (24%) | 237 (30%) | 358 (27%) | |
| Positive | 394 (76%) | 557 (70%) | 951 (73%) | |
| HER2 Status | | | | 0.001 |
| Negative | 48 (10%) | 125 (16%) | 173 (13%) | |
| Positive | 454 (90%) | 657 (84%) | 1111 (87%) | |
| Ki67 | | | | 0.18 |
| <14% | 264 (56%) | 391 (52%) | 655 (54%) | |
| ≥14% | 205 (44%) | 358 (48%) | 563 (46%) | |
| Subtype | | | | (Luminal vs. non-luminal) = 0.004 |
| Luminal A | 225 (44%) | 306 (38%) | 531 (41%) | |
| Luminal B | 151 (29%) | 242 (30%) | 393 (30%) | |
| Her2-Enriched | 22 (4%) | 65 (8%) | 87 (7%) | |
| Triple Negative | 70 (14%) | 138 (17%) | 208 (16%) | (Triple negative vs. non-triple negative) = 0.07 |
| Basal-like | 34 (7%) | 90 (11%) | 124 (9%) | |

TABLE 8

Clinicopathologic characteristics of the nuclear antigen of the pSer137-Pfn1 antibody in the validation set of the BCCancer series.

| Clinicopathologic characteristic | Nuclear p-PFN1 Allred score (0-4) (n = 533) | Nuclear p-PFN1 Allred score (5-8) (n = 807) | Total (n = 1340) | P-value |
|---|---|---|---|---|
| Age, years | | | | 0.007 |
| <50 | 179 (34%) | 215 (27%) | 394 (29%) | |
| ≥50 | 354 (66%) | 592 (73%) | 946 (71%) | |
| Tumor Size, cm | | | | 0.29 |
| ≤2 | 285 (54%) | 406 (51%) | 691 (52%) | |
| >2 | 245 (46%) | 395 (49%) | 640 (48%) | |
| Involved lymph nodes | | | | 0.34 |
| Negative | 285 (56%) | 426 (55%) | 711 (56%) | |
| 1-3 | 158 (31%) | 222 (29%) | 380 (30%) | |
| 4-9 | 48 (10%) | 91 (12%) | 139 (11%) | |
| ≥10 | 15 (38%) | 32 (4%) | (4%) | |
| Stage | | | | 0.22 |
| I | 192 (36%) | 258 (32%) | 450 (34%) | |
| II | 291 (55%) | 478 (60%) | 769 (58%) | |
| II | 47 (9%) | 65 (8%) | 112 (8%) | |
| Tumor grade | | | | 0.001 |
| 1-2 | 250 (49%) | 312 (40%) | 562 (43%) | |
| 3 | 259 (51%) | 474 (60%) | 733 (57%) | |
| Lympho-vascular Invasion | | | | 0.65 |
| Negative | 272 (53%) | 404 (52%) | 676 (32%) | |
| Positive | 240 (47%) | 378 (48%) | 618 (48%) | |
| ER Status | | | | <0.001 |
| Negative | 102 (19%) | 267 (33%) | 369 (28%) | |
| Positive | 429 (81%) | 539 (67%) | 968 (72%) | |
| HER2 Status | | | | <0.001 |
| Negative | 472 (90%) | 653 (83%) | 1125 (86%) | |

TABLE 8-continued

Clinicopathologic characteristics of the nuclear antigen of the pSer137-Pfn1 antibody in the validation set of the BCCancer series.

| Clinicopathologic characteristic | Nuclear p-PFN1 Allred score (0-4) (n = 533) | Nuclear p-PFN1 Allred score (5-8) (n = 807) | Total (n = 1340) | P-value |
|---|---|---|---|---|
| Positive Ki67 | 51 (10%) | 133 (17%) | 184 (14%) | <0.001 |
| <14% | 292 (60%) | 377 (4%) | 669 (53%) | |
| ≥14% | 197 (40%) | 384 (51%) | 581 (47%) | |
| Subtype | | | | (Luminal vs. non-luminal) <0.001 |
| Luminal A | 251 (31%) | 295 (39%) | 546 (40%) | |
| Luminal B | 160 (33%) | 230 (31%) | 390 (28%) | |
| Her2-Enriched | 22 (5%) | 76 (10%) | 98 (7%) | |
| Triple Negative | 56 (11%) | 153 (20%) | 209 (15%) | (Triple negative vs. non-triple negative) <0.001 |
| Basal-like | 24 (5%) | 105 (21%) | 129 (10%) | |

TABLE 9

Clinicopathologic characteristics of the nuclear antigen of the pSer137-Pfn1 antibody in the whole BCCancer series (only significant results on both training + validation sets are presented).

| Clinicopathologic characteristic | Allred score (0-4) (n = 1048) | Allred score (5-8) (n = 1603) | Total (n = 2651) | P-value |
|---|---|---|---|---|
| Tumor grade | | | | <0.001 |
| 1-2 | 506 (51%) | 643 (41%) | 1149 (45%) | |
| 3 | 492 (49%) | 909 (59%) | 1401 (5%) | |
| ER Status | | | | <0.001 |
| Negative | 223 (21%) | 504 (31%) | 727 (27%) | |
| Positive | 823 (79%) | 1096 (69%) | 119 (73%) | |
| HER2 Status | | | | <0.001 |
| Positive | 926 (90%) | 1310 (83%) | 2236 (86%) | |
| Negative | 99 (10%) | 258 (17%) | 357 (14%) | |
| Subtype | | | | (Luminal vs. non-luminal) <0.001 |
| Luminal A | 476 (50%) | 601 (40%) | 1077 (41.3%) | |
| Luminal B | 311 (32%) | 472 (31%) | 783 (30.1%) | |
| Her2-Enriched | 44 (5%) | 141 (10%) | 185 (7.1%) | |
| Triple Negative | 126 (13%) | 291 (19%) | 417 (16%) | (Triple negative vs. non-triple negative) <0.001 |
| Basal-like | 58 (6%) | 195 (13%) | 253 (9.7%) | |

Figure 6A:
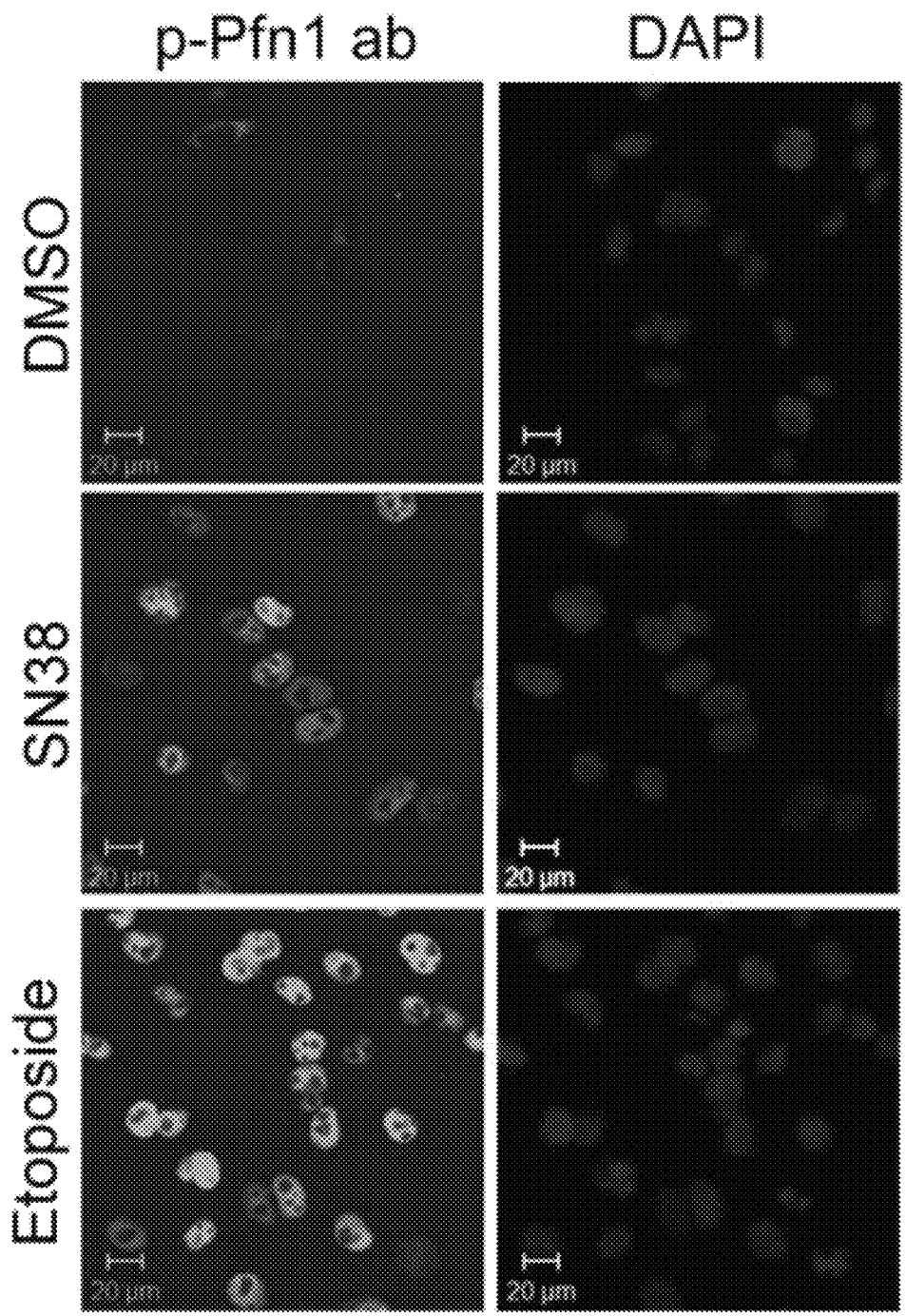
FIG. 6A-6I shows pSer$^{784}$-VCP is the DNA-Damage-Induced nuclear antigen of the pSer$^{137}$-Pfn1 antibody.
Figure 7A:
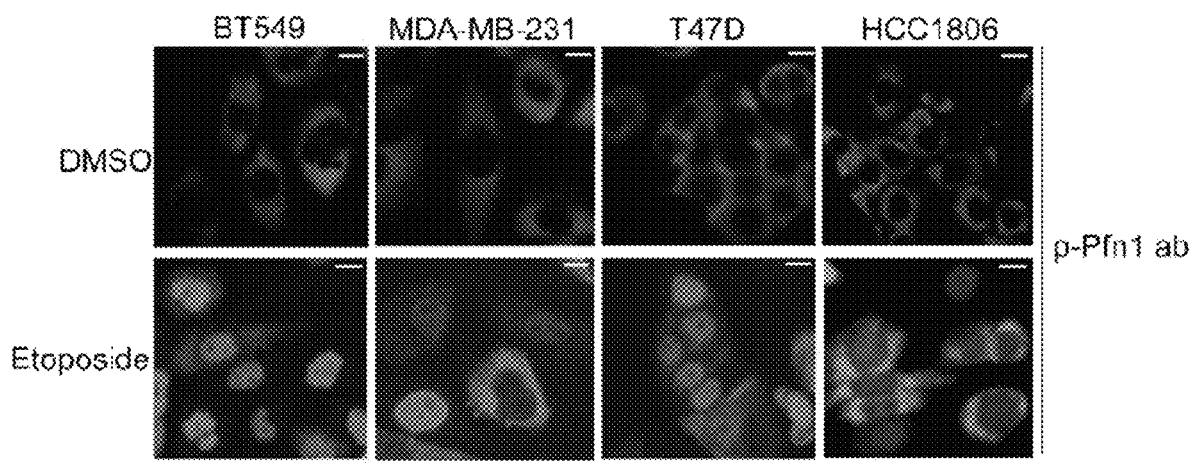
FIG. 7A-7D shows Genotoxin-induced nuclear antigen of the pSer$^{137}$-Pfn1 antibody is not Pfn1.
Figure 7B:
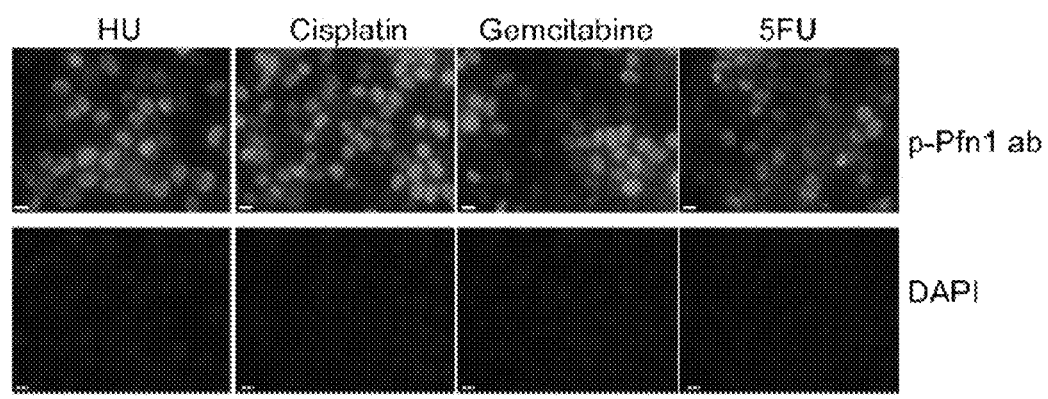
Figure 7C:
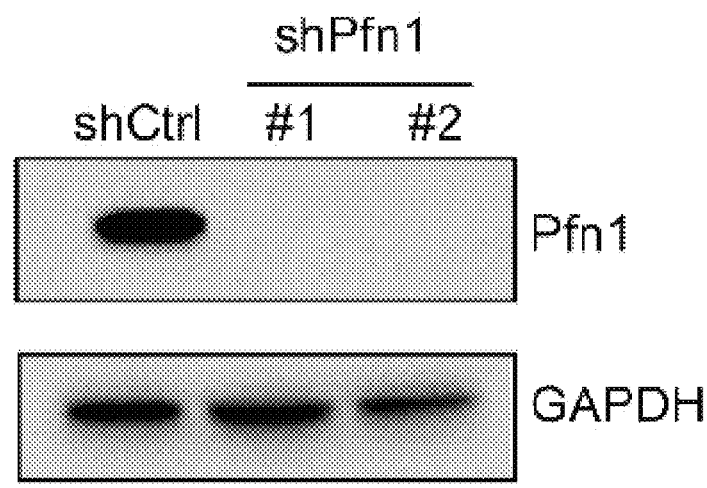
Figure 7D:
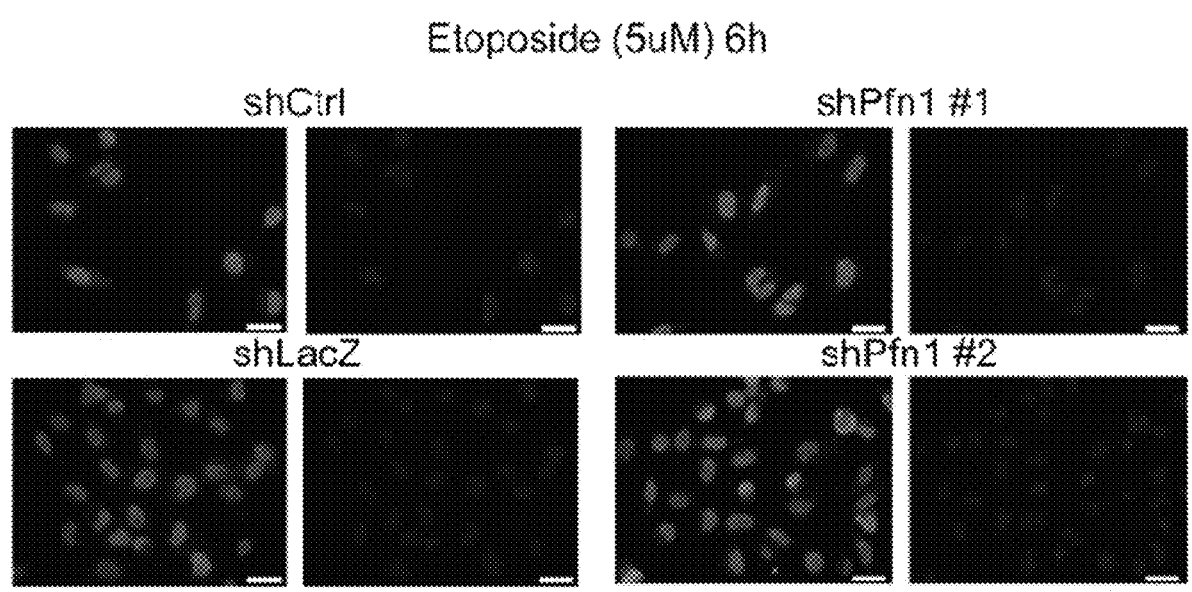

VCP Is the DNA-Damage-Induced Nuclear Antigen Detected by the pSer$^{137}$-Pfn1 Antibody: Nearly all the chemotherapy drugs used to treat patients in the BCCancer series are genotoxins (cyclophosphamide, methotrexate, 5-fluorouracil, and anthracycline). To investigate whether there is a link between the nuclear antigen of the pSer$^{137}$-Pfn1 antibody and the DNA-damage response, HeLa and several breast cancer cell lines (BT549, MDA-MB-231, T47D, and HCC1806) were treated with SN38 (DNA topoisomerase I inhibitor) and etoposide (DNA topoisomerase II inhibitor). Although the untreated cells mainly displayed cytoplasmic reactivity with the pSer$^{137}$-Pfn1 antibody, both drugs induced nuclear signals to various degrees (FIG. 6A and FIG. 7A). Similar nuclear signals were induced by genotoxic agents with different mechanisms of action (FIG. 7B) including hydroxyurea (HU), 5-fluorouracil (5FU), cisplatin, and gemcitabine. Unexpectedly, Pfn1 knockdown by two different short hairpin RNAs (shRNAs), although reducing Pfn1 to an undetectable level, showed no effect on etoposide-induced nuclear staining (FIG. 7C and FIG. 7D), suggesting that the nuclear antigen is a different protein.

Figure 5A:
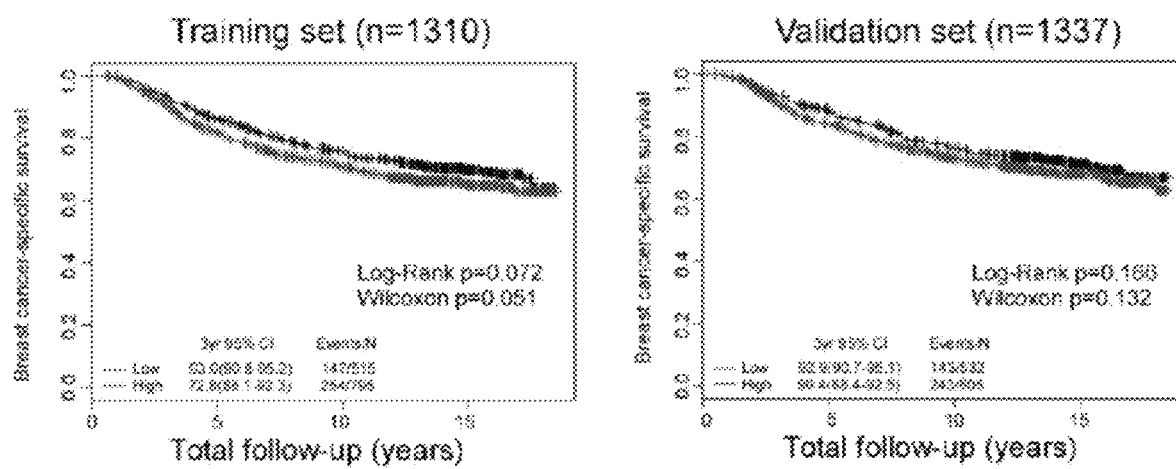
FIG. 5A-5C show nuclear antigen recognized by the pSer$^{137}$-Pfn1 antibody associates with worse outcome of breast cancer treated with chemotherapy in the BCCancer series, related to FIG. 2E.
Figure 5B:
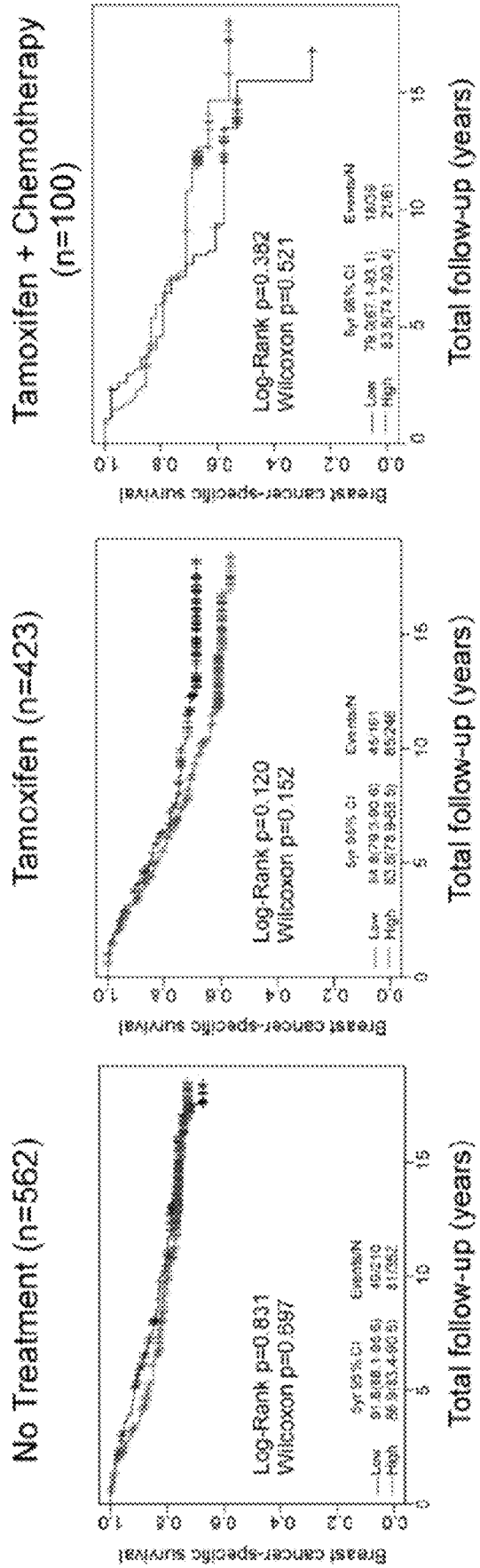
Figure 5C:
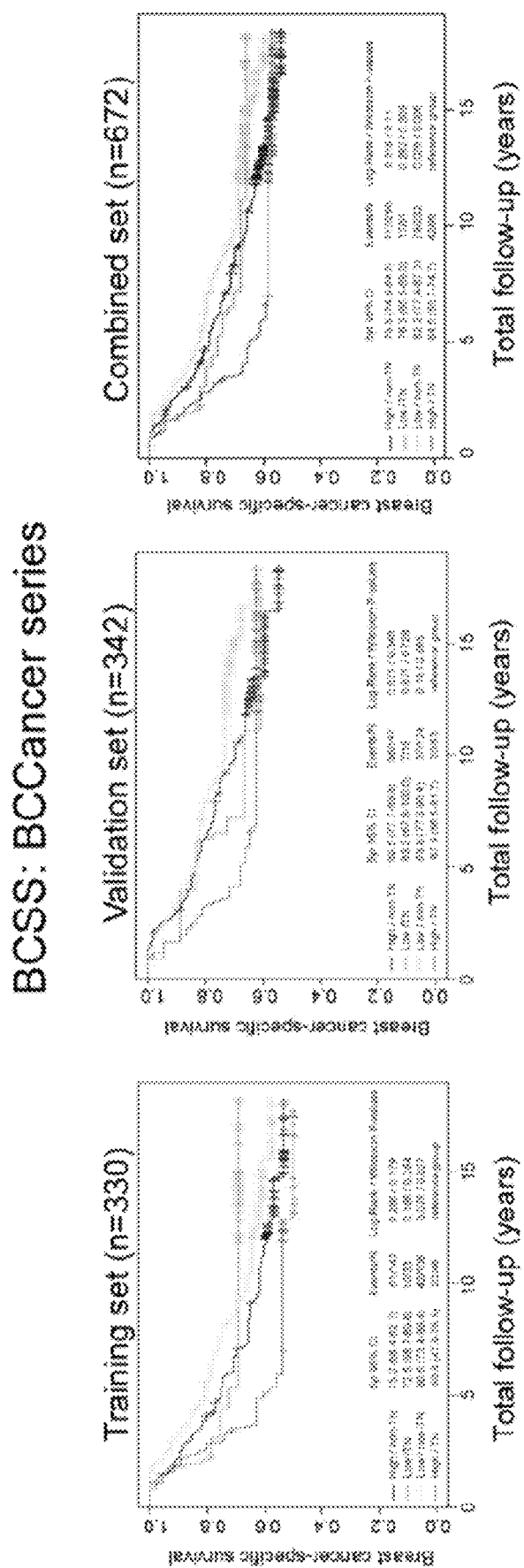

Because the nuclear score appeared to be particularly prognostic for TNBC in the UBC dataset (FIG. 2D), an exploratory analysis was performed to determine whether the combination of immunohistochemical (IHC) staining and TNBC status would provide additional information regarding survival in the cohort of patients treated with chemotherapy. It was found that tumors classified as "TNBC and with high nuclear scores" had the worst BCSS compared with the other subgroups (p=0.028, combined set; FIG. 5C). Thus, the data suggest that the level of nuclear staining by the pSer$^{137}$-Pfn1 antibody could potentially predict breast cancer response to chemotherapy treatments.

Figure 6B:
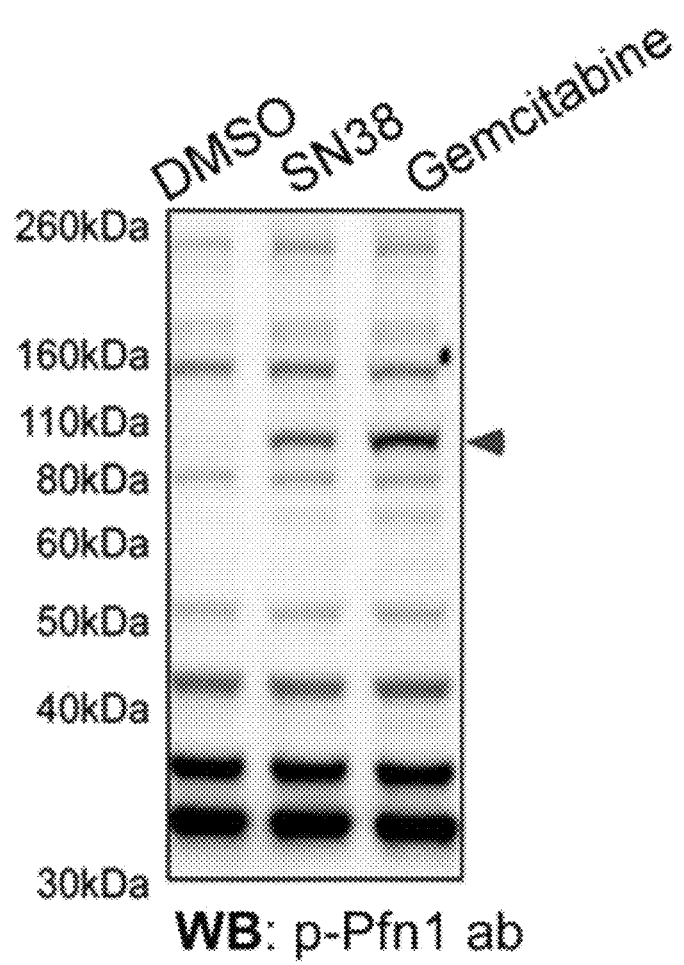
Figure 6C:
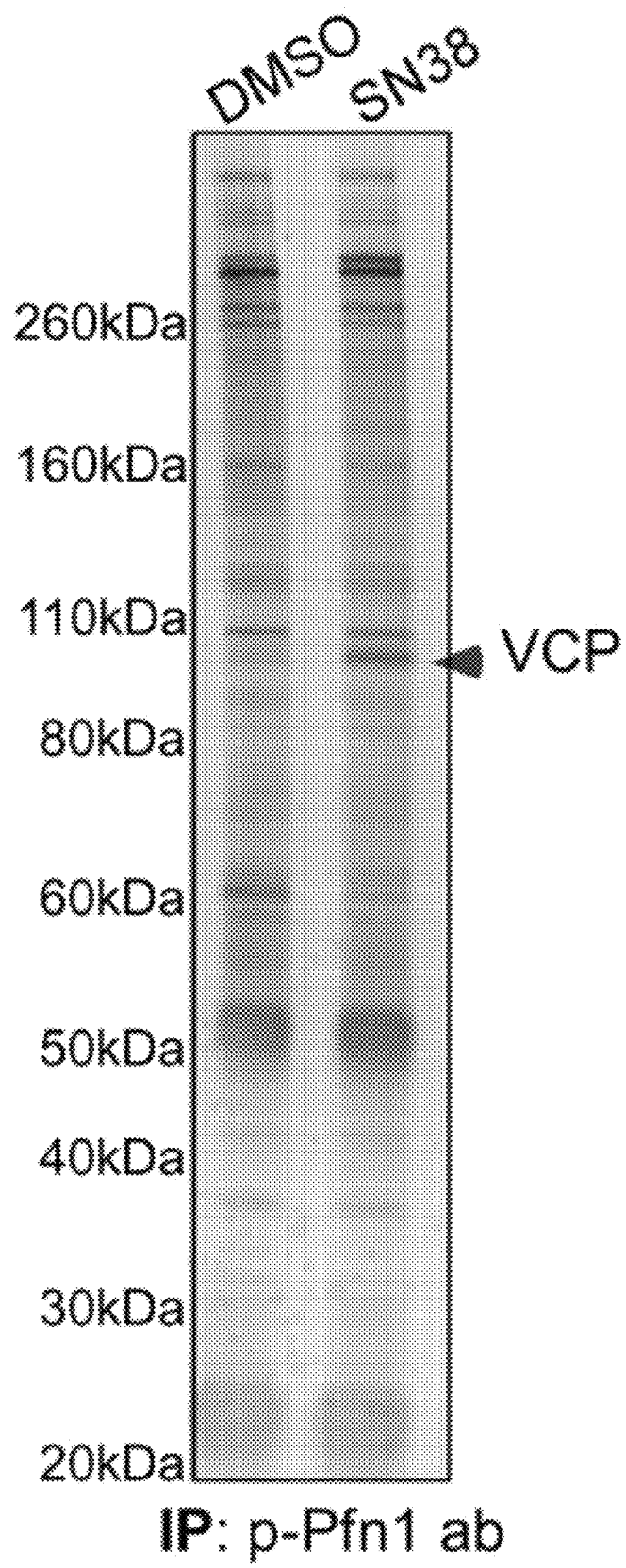
Figure 6D:
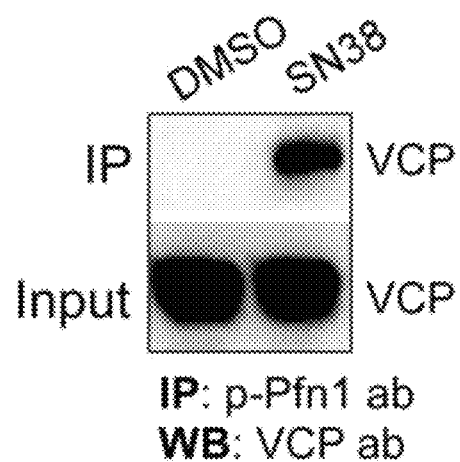
Figure 8A:
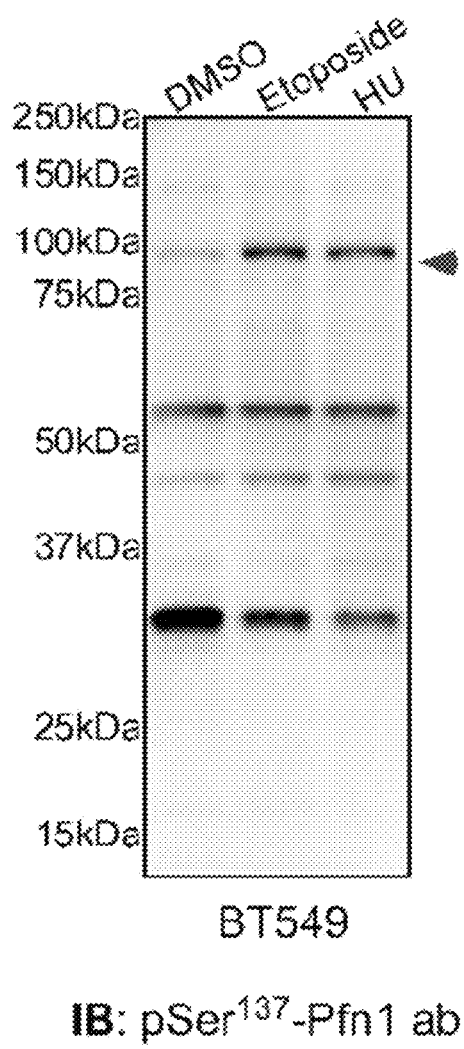
FIG. 8A-8G shows identification and characterization of pSer$^{784}$-VCP.
Figure 8B:
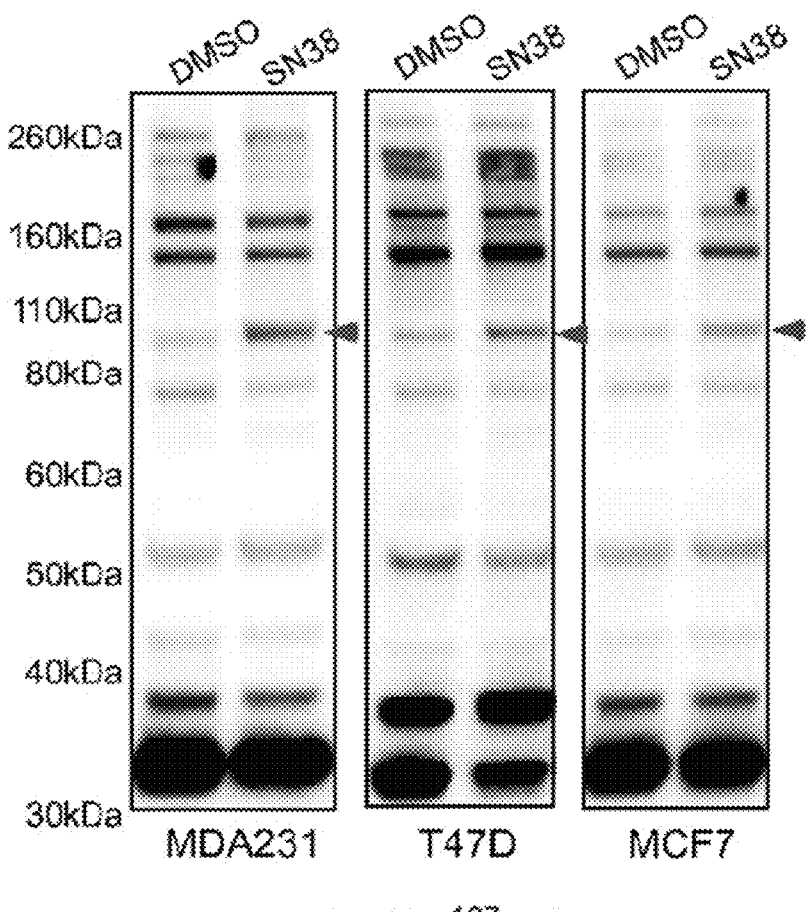
Figure 8C:
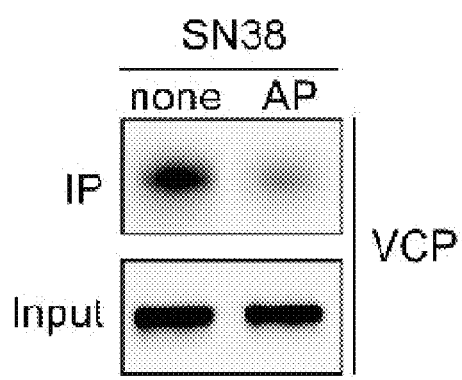

Because of its clinical importance (FIG. 2), the unknown nuclear antigen was sought to be identified. Treating multiple cell lines with different genotoxic agents reveals an ~100-kDa protein recognized by the pSer$^{137}$-Pfn1 antibody (FIG. 6B, FIG. 8A, and FIG. 8B). To identify that protein, the nuclear extracts of untreated or SN38-treated Hela cells were subjected to immunoprecipitation using the pSer$^{137}$-Pfn1 antibody. Silver staining reveals an ~100-kDa protein specifically present in the SN38-treated sample (FIG. 6C), which was identified by mass spectrometry to be the AAA+ ATPase VCP. This was confirmed by western blot using a VCP antibody (FIG. 6D). Incubating cell lysates with alkaline phosphatase before immunoprecipitation by the pSer$^{137}$-Pfn1 antibody significantly reduced the binding of VCP, confirming that the reactivity is phosphorylation dependent (FIG. 8C).

Figure 6E:
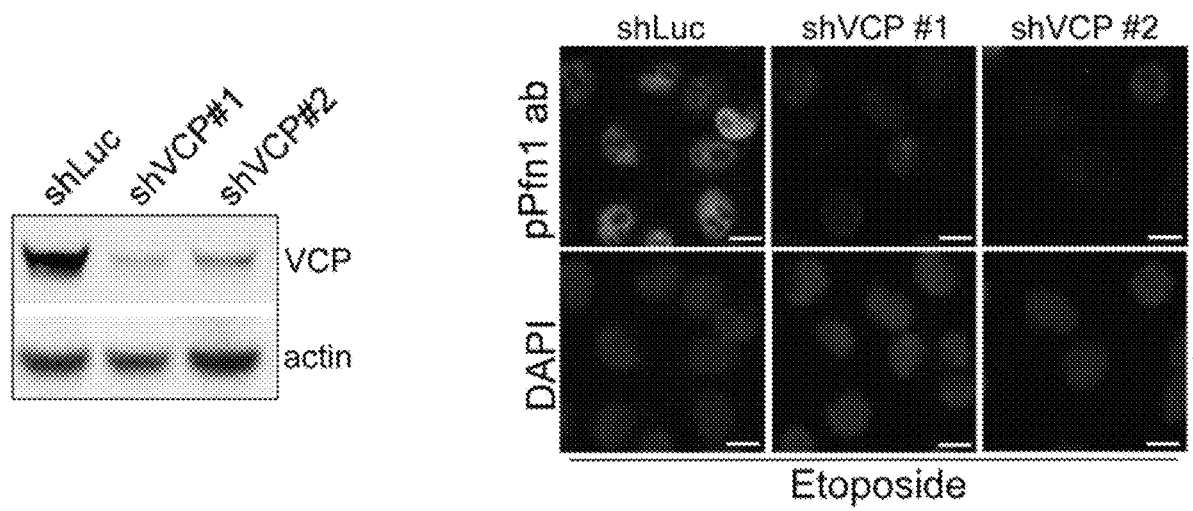
Figure 6F:
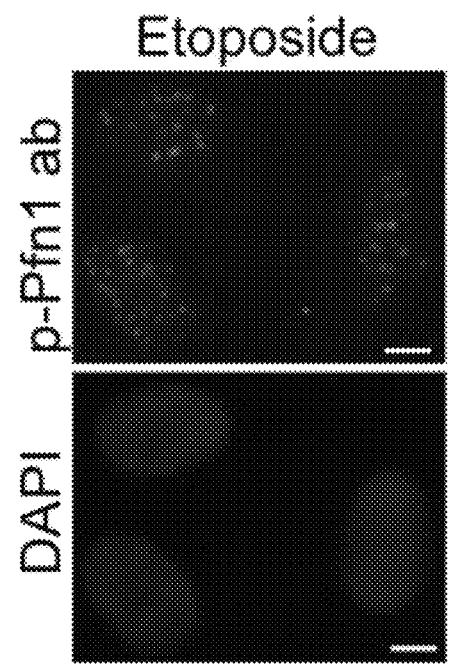

To confirm that VCP is the nuclear antigen of the pSer$^{137}$-Pfn1 antibody by immunostaining, VCP was silenced in Hela cells using two shRNAs, treated with SN38, and immunostaining performed with the pSer$^{137}$-Pfn1 antibody. Although nuclear signals are observed in cells infected with a control shRNA, little to no signals were present in the VCP knockdown cells (FIG. 6E). Notably, detergent extraction of etoposide-treated Hela cells before fixation and staining revealed discrete nuclear structures characteristic of DNA-damage foci (FIG. 6F). Thus, VCP is the DNA-damage-induced nuclear antigen of the pSer$^{137}$-Pfn1 antibody.

Figure 6G:
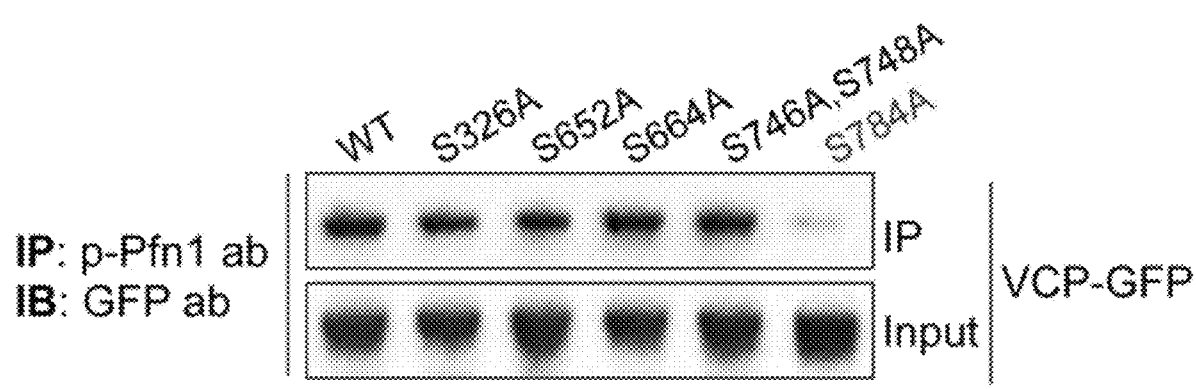
Figure 6H:

Ser784 Is the Phosphorylation Site of VCP Recognized by the pSer$^{137}$-Pfn1 Antibody: It was next sought to identify the VCP epitope that reacts with the pSer$^{137}$-Pfn1 antibody. Because there is no obvious similarity between the antigenic pSer$^{137}$-Pfn1 peptide and the VCP sequence, a candidate approach was taken by individually mutating five serines to alanines in a VCP-GFP construct and determining the ability of the pSer$^{137}$-Pfn1 antibody to recognize the VCP mutants upon DNA damage. The five serines are either preceded by 1-2 basic residues (R/KS) or followed by a glutamate (SQ) as Ser137 in the antigenic Pfn1 peptide. Upon transfection into HEK293T cells and SN38 treatment, the pSer$^{137}$-Pfn1 antibody was used to immunoprecipitate wild-type versus mutant VCP-GFP, followed by western blot using a GFP antibody. One mutant, S784A, although abundantly expressed, was not pulled down by the pSer$^{137}$-Pfn1 antibody (FIG. 6G). It also does not react with the antibody directly on western blot (FIG. 6H).

Phosphorylation of VCP at Ser784 has been reported to occur in response to different genotoxic treatments, but the functional significance remains completely unknown.

Figure 6I:
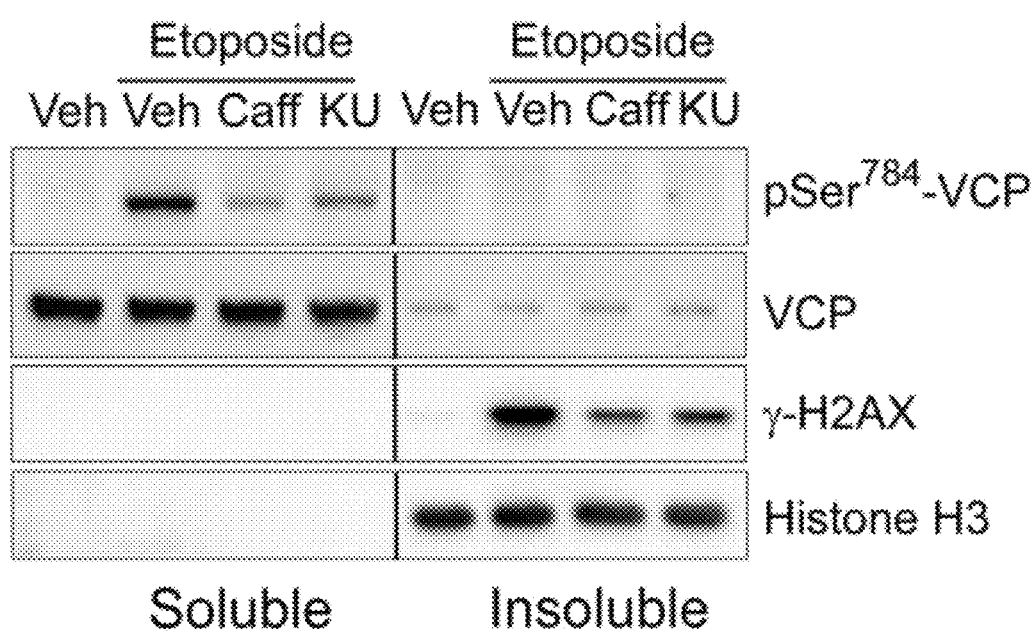

Residing in a pSQ motif, it is believed to be directly phosphorylated by the PIKK family members ATM, ATR, or DNA-PKcs, known as master DDR regulators. Consistent with that, treating Hela cells with caffeine (general ATM/ATR/DNA-PKcs inhibitor) and KU55933 (specific ATM inhibitor) significantly inhibits Ser784 phosphorylation caused by etoposide (predominantly inducing DSBs, which activate ATM) (FIG. 6I). Interestingly, when cells are lysed with SDS-free RIPA buffer (radioimmunoprecipitation assay buffer; 1% NP40 and 1% sodium deoxycholate), pSer$^{784}$-VCP is found exclusively in the soluble fraction, although a small fraction of total VCP is detected in the insoluble fraction (FIG. 6I).

Figure 8D:
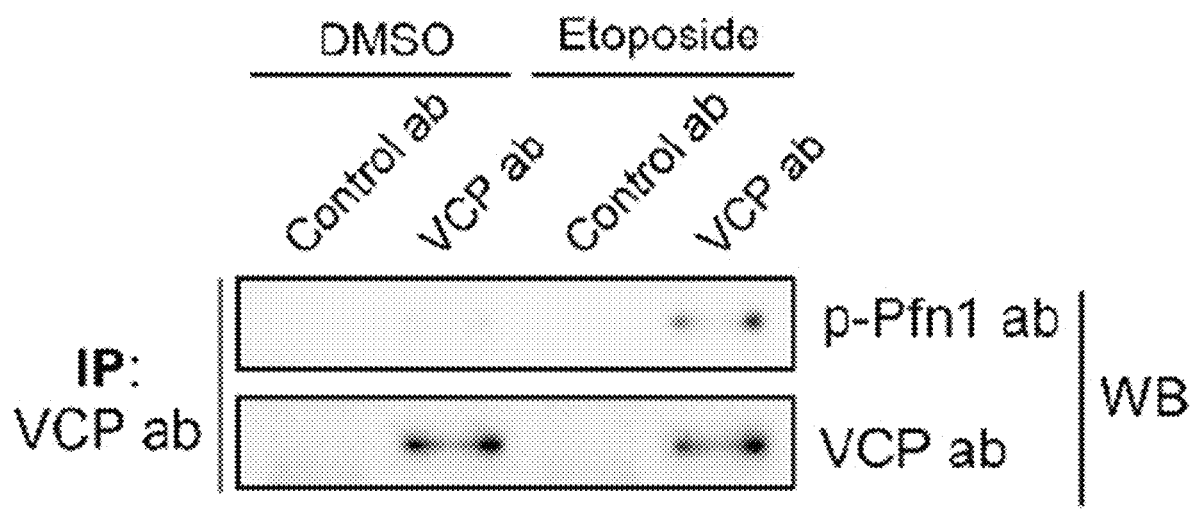
Figure 8E:
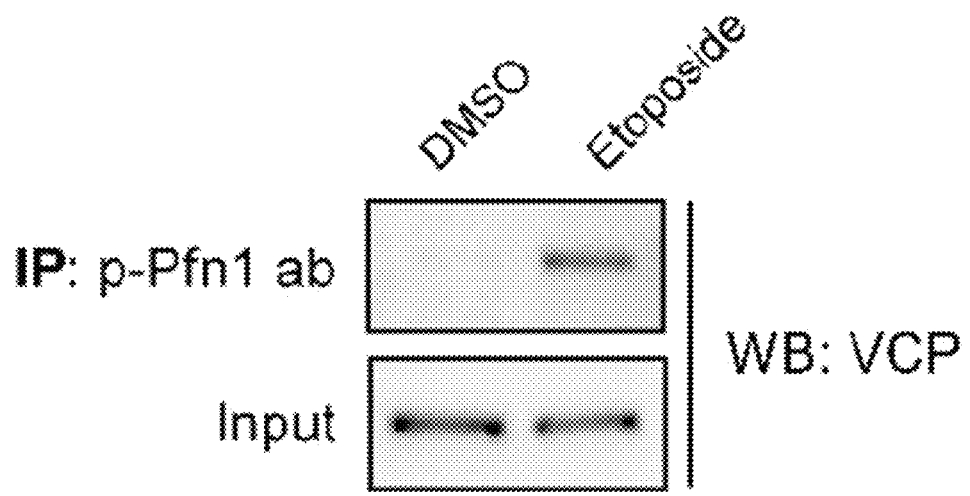
Figure 8F:
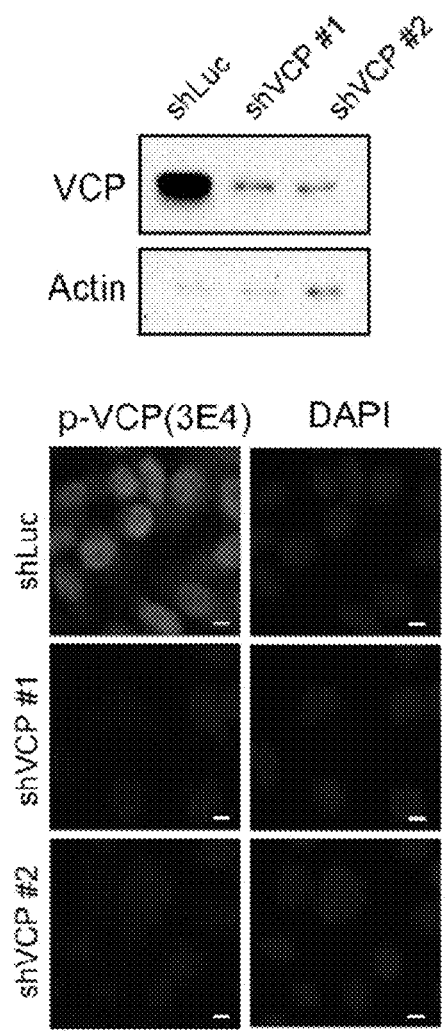
Figure 9A:
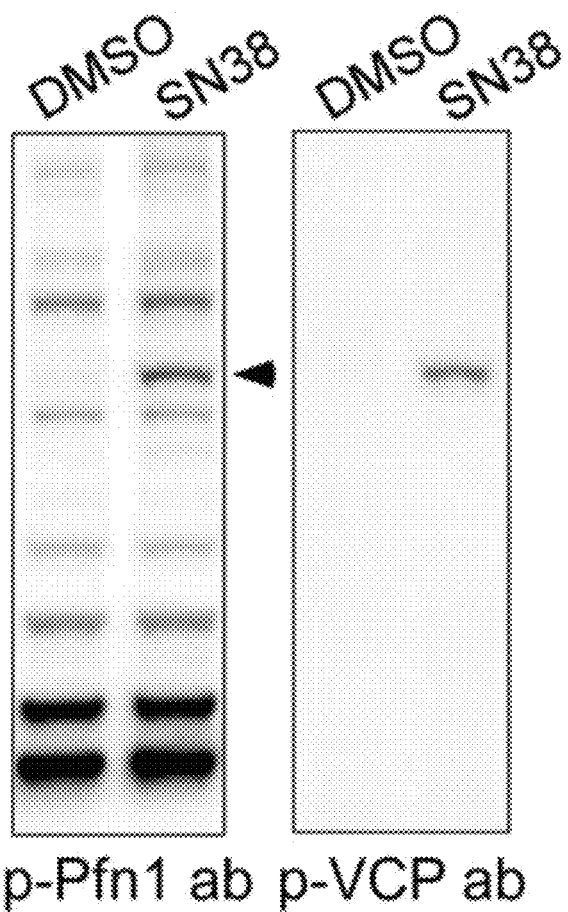
FIG. 9A-9J show monoclonal pSer$^{784}$-VCP antibody confirms the nuclear antigen of the pSer$^{137}$-Pfn1 antibody.
Figure 9B:
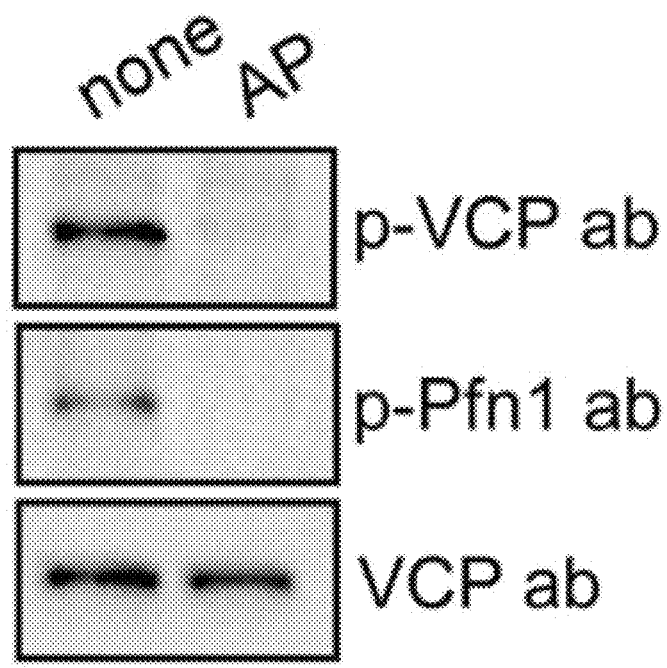
Figure 9C:
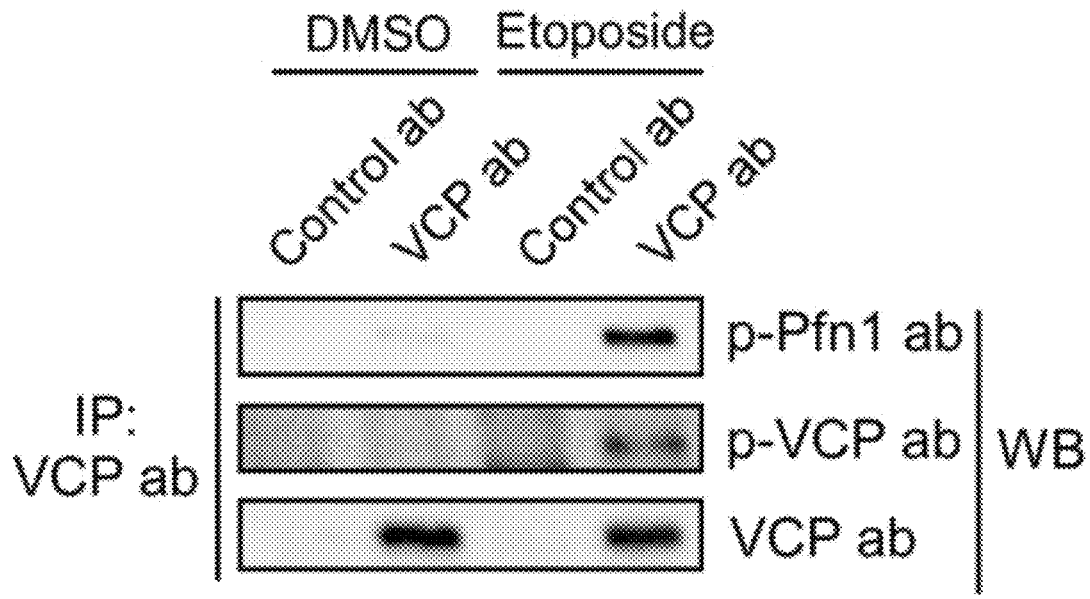
Figure 9D:
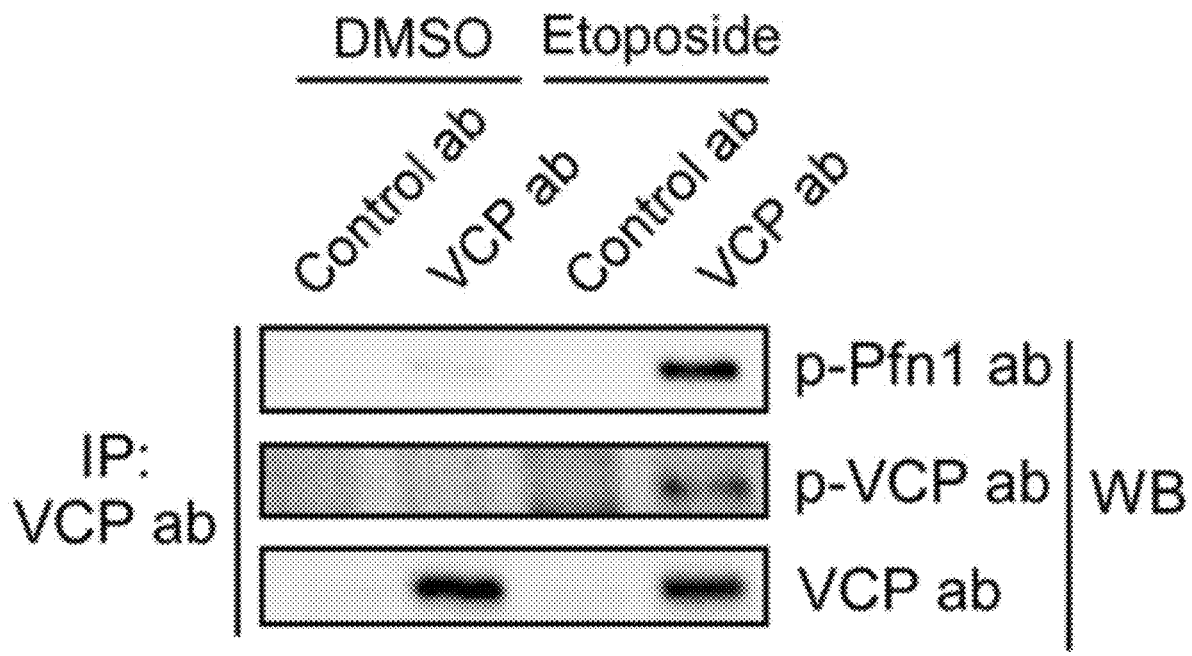
Figure 9E:
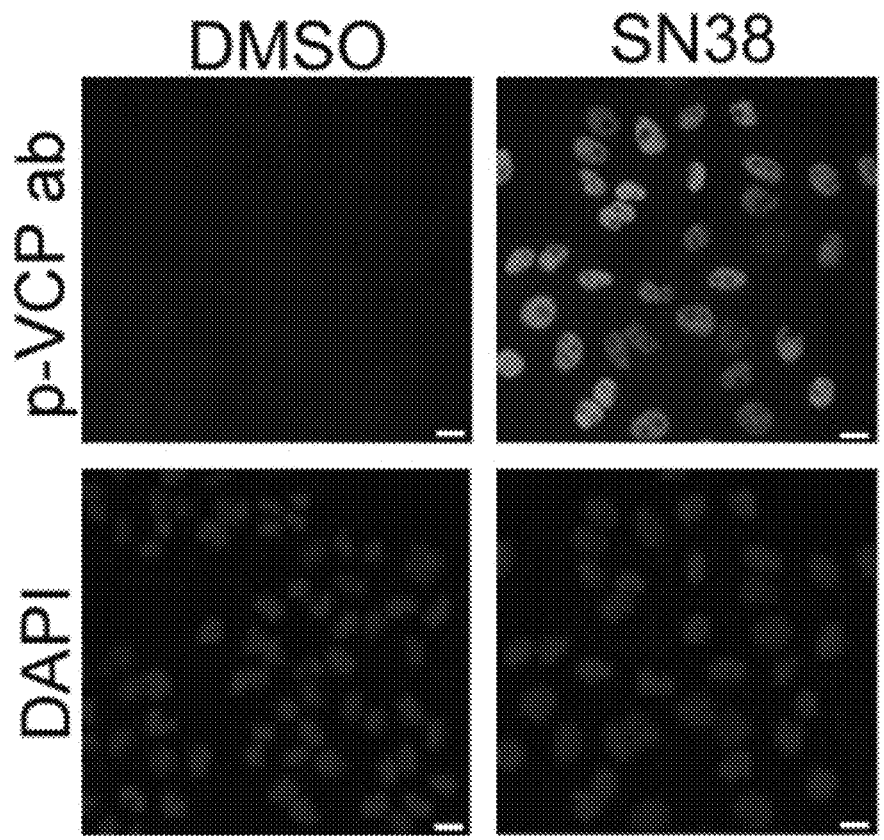

Generation and Characterization of the Monoclonal pSer784-VCP Antibody: To further confirm the results and better study pSer$^{784}$-VCP, monoclonal antibodies were generated using a synthetic VCP-peptide-harboring pSer784 (GGAGPpS784QGSGGG) (SEQ ID NO:1). One clone (3E4) was evaluated in parallel to the pSer$^{137}$-Pfn1 antibody. 3E4 shows superior specificity on western blot and detects the same 100-kDa protein recognized by the pSer$^{137}$-Pfn1 antibody under DNA-damaging conditions (FIG. 9A) in an alkaline-phosphatase-sensitive manner (FIG. 9B). This phospho-protein was confirmed to be VCP by anti-VCP pull-down under native and denaturing conditions followed by immunoblotting using the 3E4 or pSer$^{137}$-Pfn1 antibodies (FIG. 9C and FIG. 8D). In a reciprocal fashion, both antibodies pull down VCP specifically from genotoxin-treated cells under the native condition (FIG. 9D), and the pSer$^{137}$-Pfn1 antibody can also do this under the denaturing condition (FIG. 8E). For immunostaining, 3E4 specifically detects nuclei in a DNA-damage-dependent fashion, which is abolished by VCP knockdown (FIG. 8F), and shows no reactivity in untreated cells (FIG. 9E).

Figure 8G:
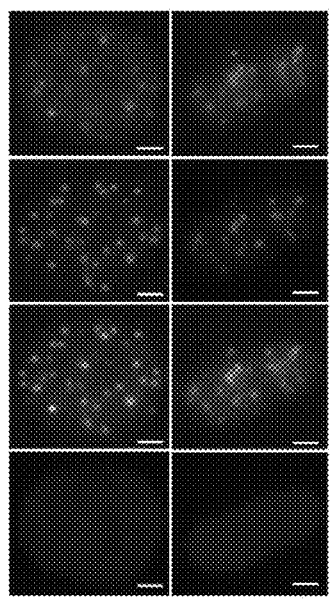
Figure 8G:
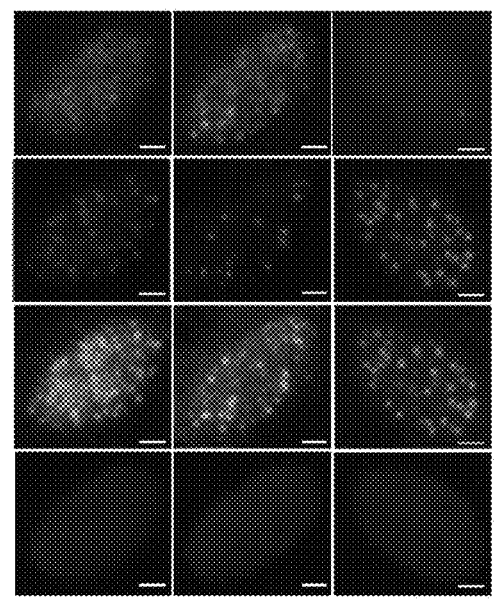
Figure 9F:
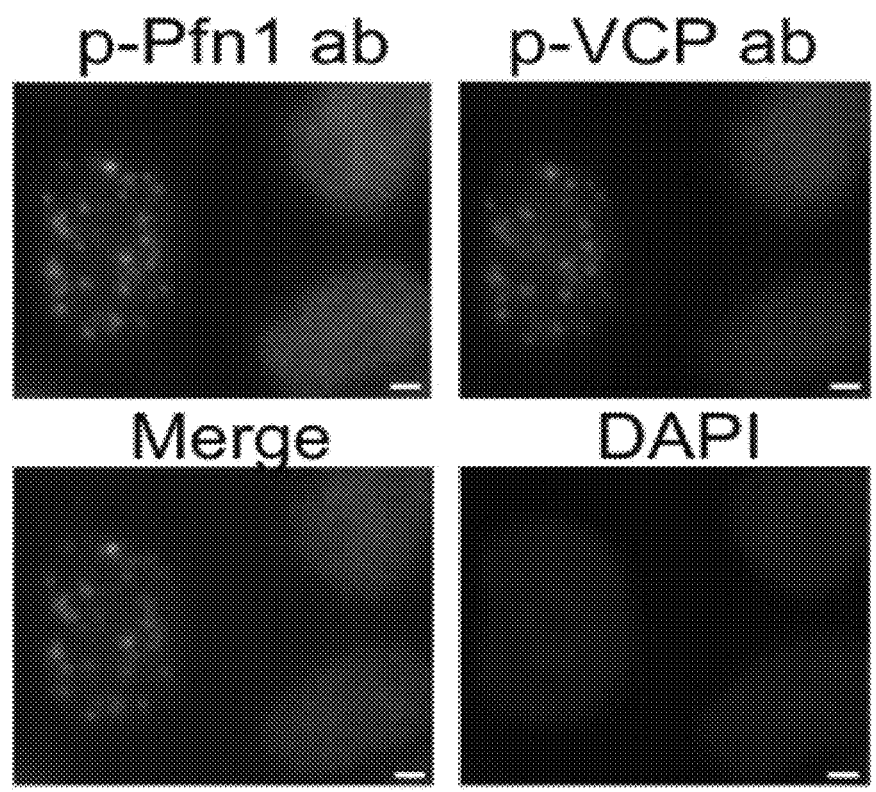
Figure 9G:
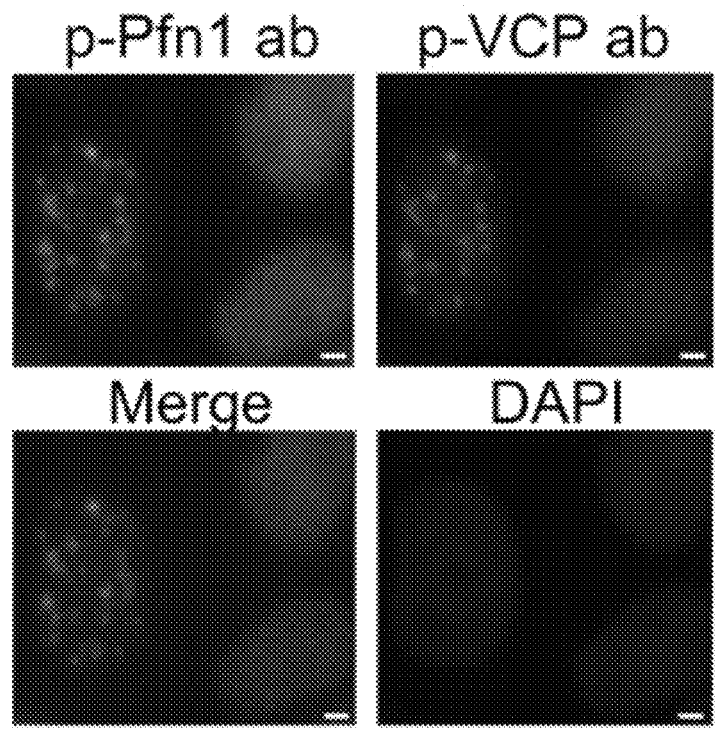
Figure 9H:
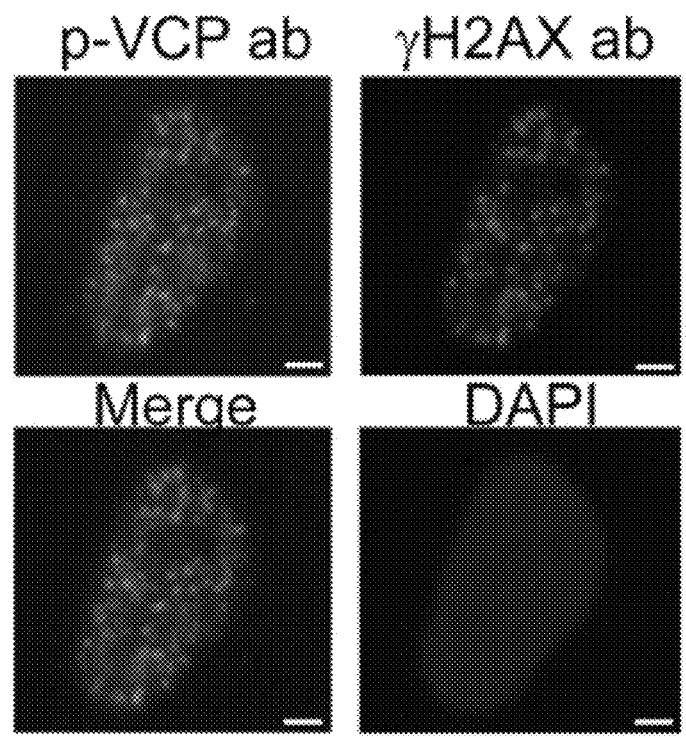

Next, it was tested whether the DNA-damage-induced nuclear foci detected by 3E4 and the pSer$^{137}$-Pfn1 antibody (FIG. 6F) are identical by double labeling of etoposide-treated, pre-extracted osteosarcoma U2OS cells. Complete co-localization of the nuclear foci recognized by the two antibodies were observed in all focus-containing cells (FIG. 9F). To confirm that they are DNA-damage foci, the cells were co-stained for well-known DSB markers (γH2AX) and repair factors (53BP1 and BRCA1). Co-localization of pSer$^{784}$-VCP was observed with nearly all the 53BP1-positive DNA-damage foci, consistent with the fact that DSB recruitment of 53BP1 requires VCP (FIG. 9G). Significant co-localization between pSer784-VCP and γH2AX was also detected in more than 50% of the focus-containing cells (FIG. 9H). Interestingly, minimal co-localization was detected between pSer$^{784}$-VCP and BRCA1. Fewer cells contained BRCA1-positive nuclear foci than pSer$^{784}$-VCP-positive foci, and of those positive for BRCA1, <10% showed only partial co-localization with pSer$^{784}$-VCP (FIG. 8G). Thus, pSer$^{784}$-VCP is physically present at a subset of DNA-damage sites containing selective DNA repair factors.

Figure 9I:
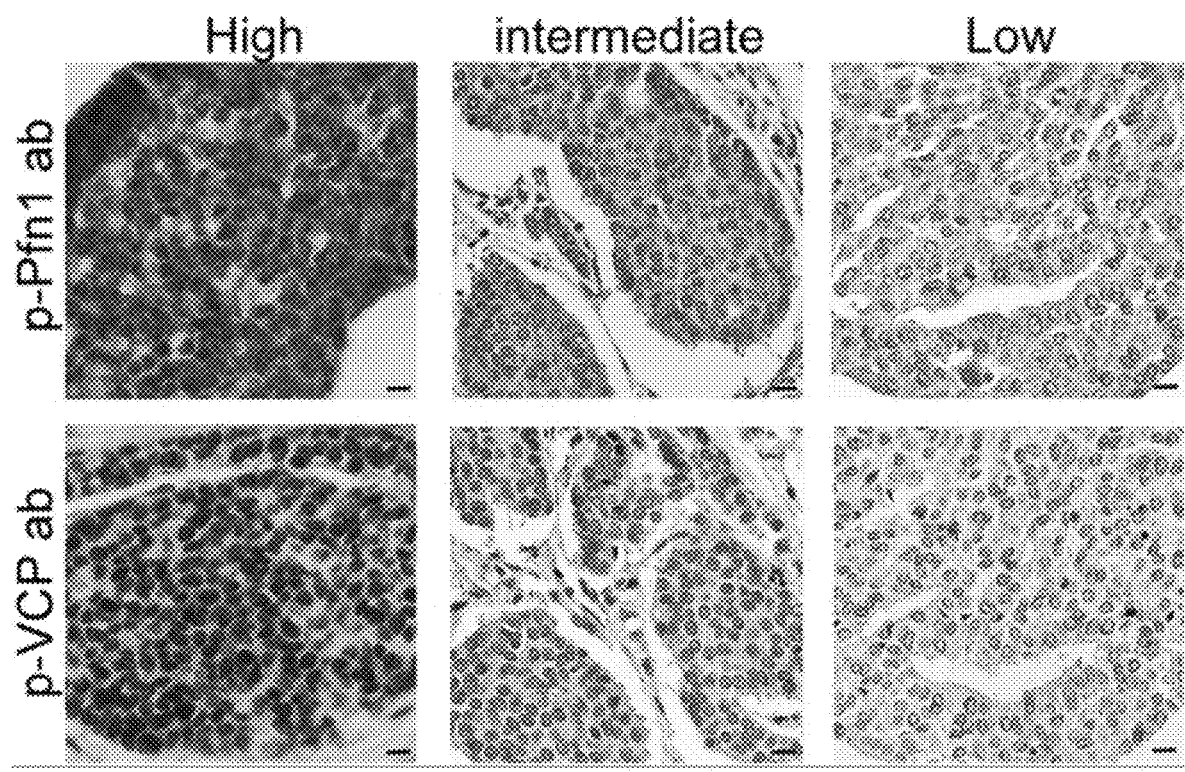
Figure 9J:
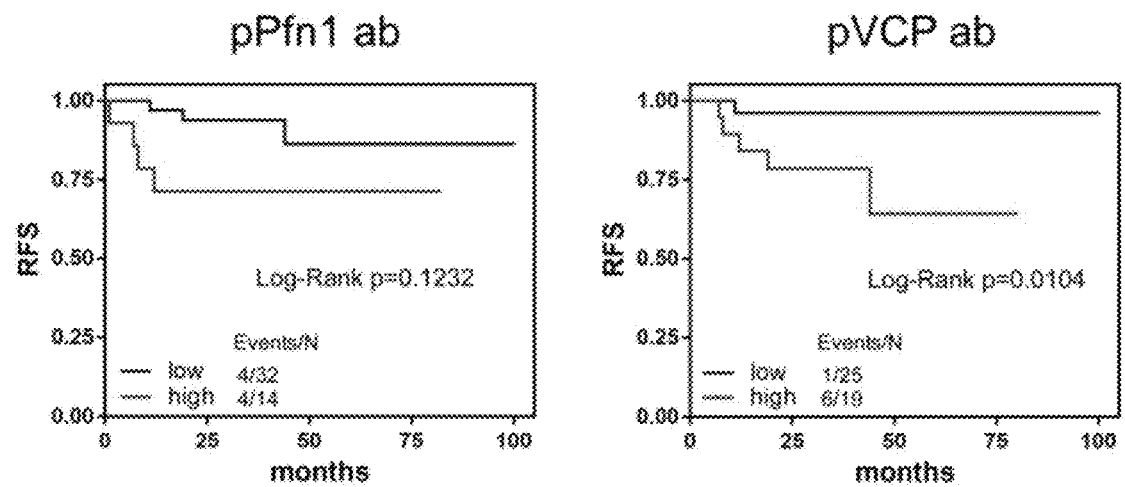

To further confirm that the nuclear antigen of the polyclonal pSer$^{137}$-Pfn1 antibody in human breast cancer tissues is pSer$^{784}$-VCP (FIG. 2), parallel staining using the SPECS TMA was performed. Comparison of nuclear Allred scores of the remaining tissues (n=69, fewer cases than earlier staining because of the extensive cutting of the block) revealed highly concordant staining patterns of 3E4 and the pSer$^{137}$-Pfn1 antibody (Pearson correlation coefficient, r2=0.9) (FIG. 9I). Univariate Kaplan-Meier analysis using further filtered cases containing a sufficient number of tumor cells revealed that nuclear staining by the monoclonal 3E4 antibody was significantly correlated with worse RFS (n=44, p=0.0104, log-rank test), in the same trend as nuclear staining by the polyclonal pSer$^{137}$-Pfn1 antibody (n=46, p=0.1232, log-rank test) (FIG. 9J). Despite the limited statistical power because of the few cases, these data collectively support that the two antibodies detect a common nuclear antigen, pSer$^{784}$-VCP.

Figure 10A:
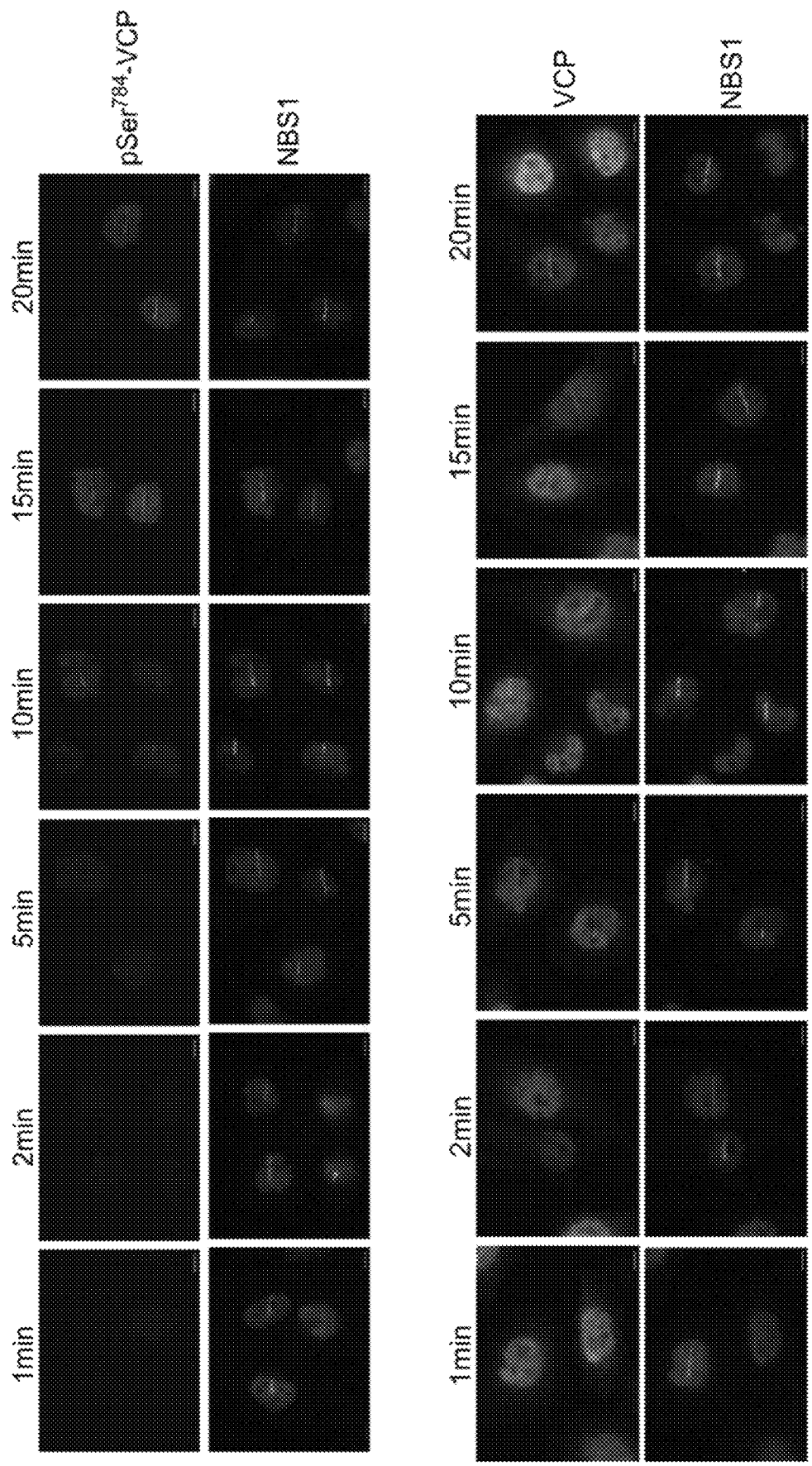
FIG. 10A-10B show Ser784 Phosphorylation is a late DNA-Damage-Induced event.
Figure 11A:
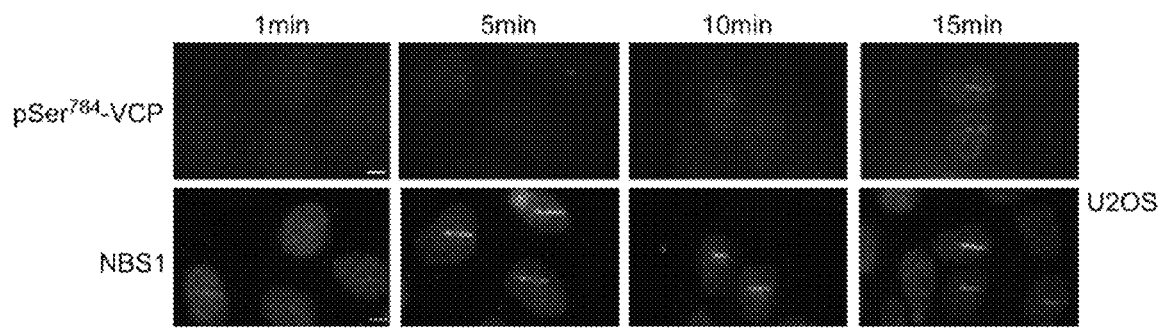
FIG. 11A-11C show pSer$^{784}$-VCP is a late DDR event.
Figure 11B:
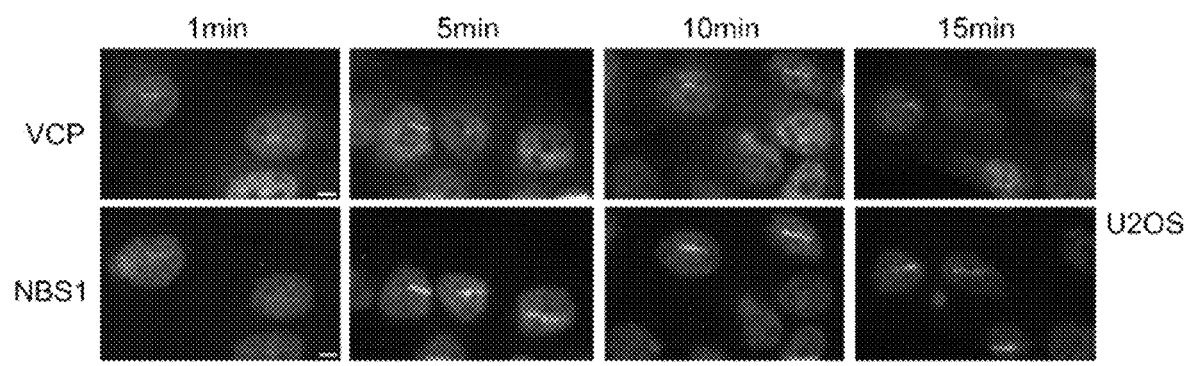

Ser784 Phosphorylation Is a Late DNA-Damage-Induced Event: VCP is well-known for its rapid recruitment to DNA-damage sites to remove K48-linked polyubiquitinated protein substrates. Upon laser-induced DSB in MRC5 fibroblast cells, the biological half-life (t1/2) of VCP-GFP recruitment is reported to be 2 min. To determine the kinetics of Ser784 phosphorylation upon DNA damage, laser microirradiation in U20S and BT549 cells were performed and the kinetics of damage site appearance of total VCP versus pSer$^{784}$-VCP compared by immunostaining at different times. VCP was detected at DNA-damage sites (indicated by NBS1, part of the DSB sensor MRN complex) as early as 1 min after laser irradiation in the U2OS cells and 5 min in the BT549 cells. In contrast, pSer$^{784}$-VCP was undetectable until 10-15 min in both cell lines. Interestingly, diffuse nucleoplasmic pSer$^{784}$-VCP, although undetectable before laser irradiation, appeared upon DNA damage and intensified in parallel to pSer$^{784}$-VCP at the laser-induced DNA wounds (FIG. 10A, FIG. 11A, and FIG. 11B). Thus, Ser784 phosphorylation occurs as a direct consequence of DNA damage and later than VCP recruitment to damage sites.

Figure 10B:
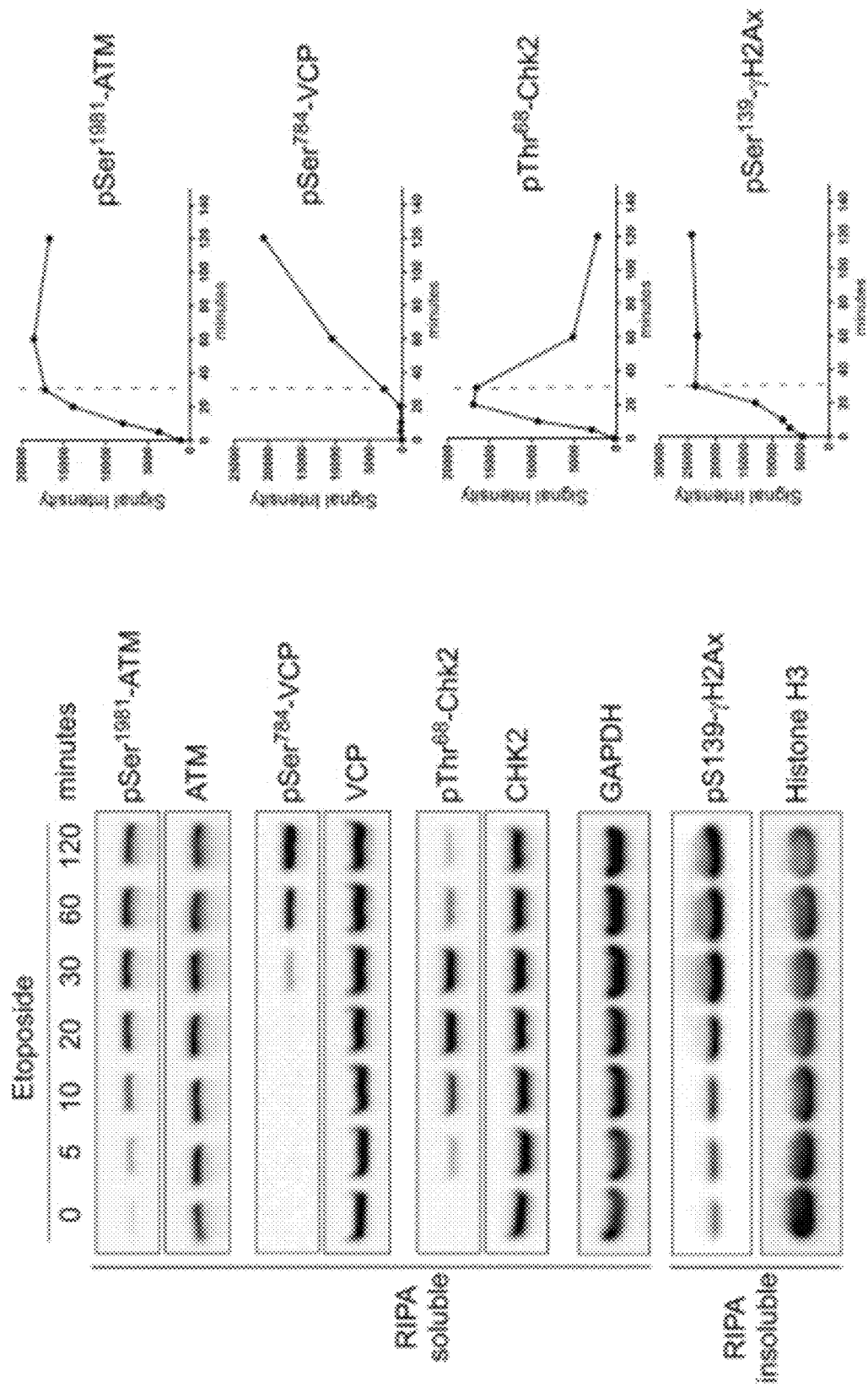
Figure 11C:
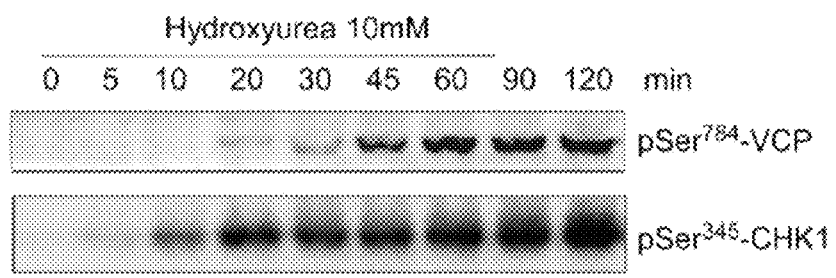

Next, DSB were chemically induced next in Hela cells using etoposide and monitored pSer$^{784}$-VCP by western blot at different times and compared it to well-known DDR signaling events including auto-phosphorylation of ATM (pSer$^{1981}$-ATM) and ATM-dependent phosphorylation of Chk2 (Thr68) and H2AX (Ser139). Although these known DDR phosphorylation events occur quickly before (pThr68-Chk2 and pSer1981-ATM) or around 5 min (γH2AX) of treatment and reach maximal intensities around 30 min, pSer$^{784}$-VCP is detectable after 20 min and gradually intensifies beyond 120 min. No changes in the total protein levels were observed (FIG. 10B). Similarly delayed pSer$^{784}$-VCP induction by hydroxyurea (inducing DNA replication stress and ATR activation) as compared with pSer$^{345}$-Chk1 (known ATR substrate) was also observed (FIG. 11C). Thus, Ser784 phosphorylation of VCP is a relatively late DDR event.

Figure 12A:
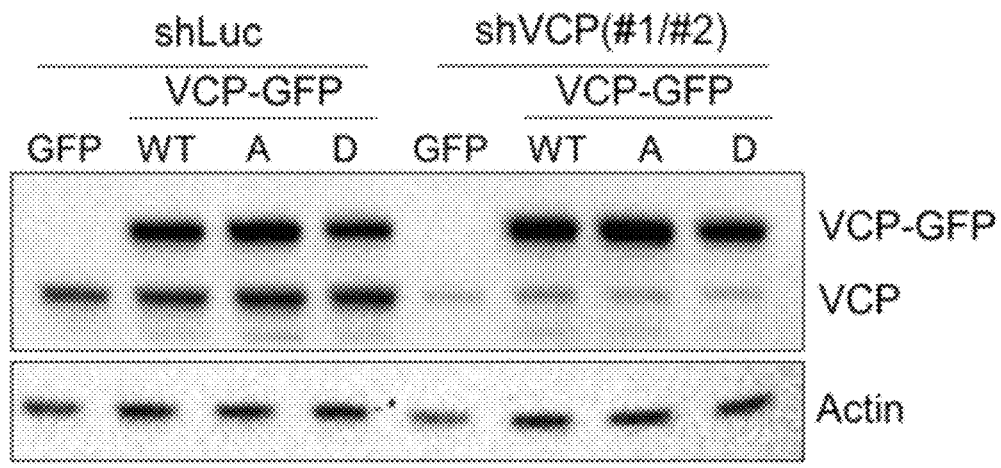
FIG. 12A-12E show Ser784 phosphorylation increases VCP activity specifically in the nucleus.
Figure 12B:
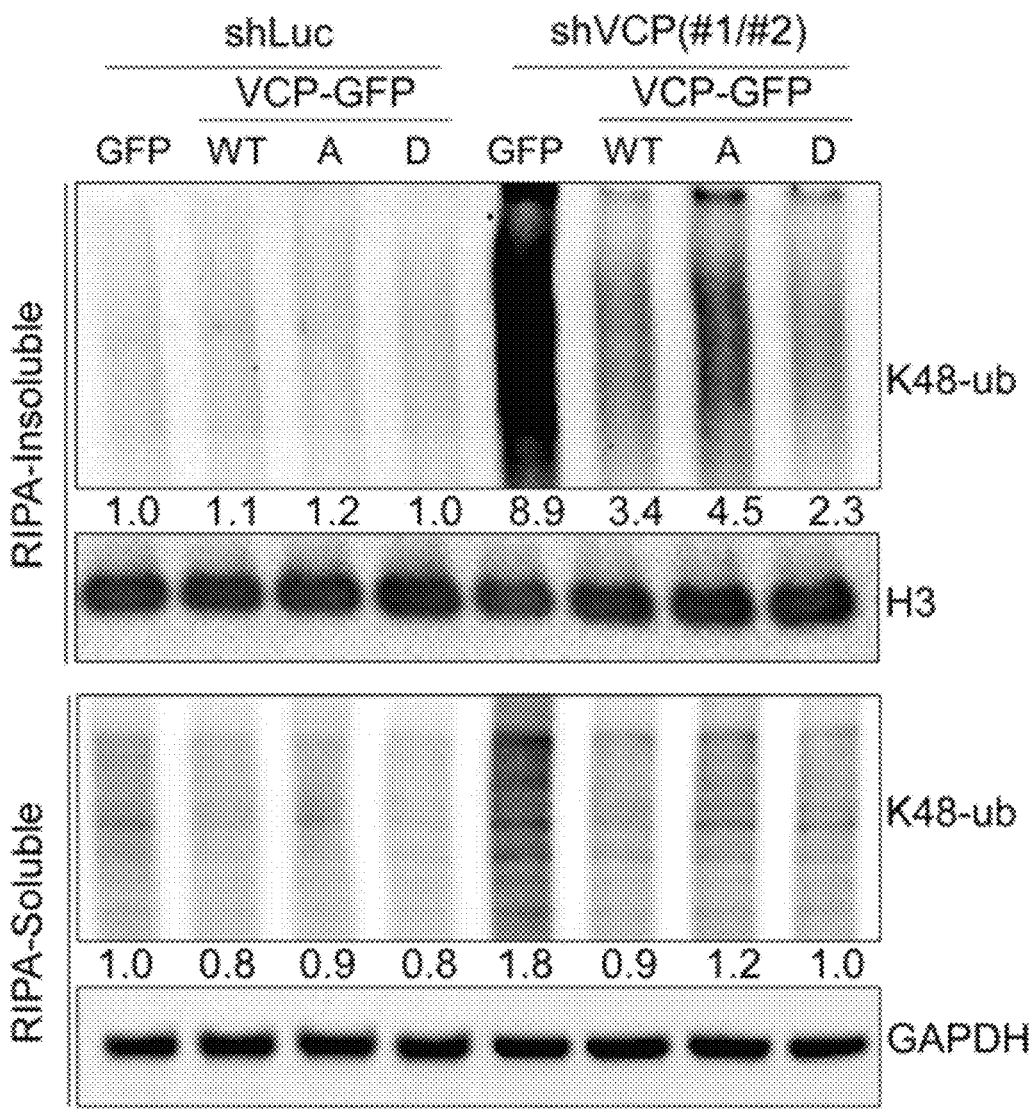
Figure 12C:
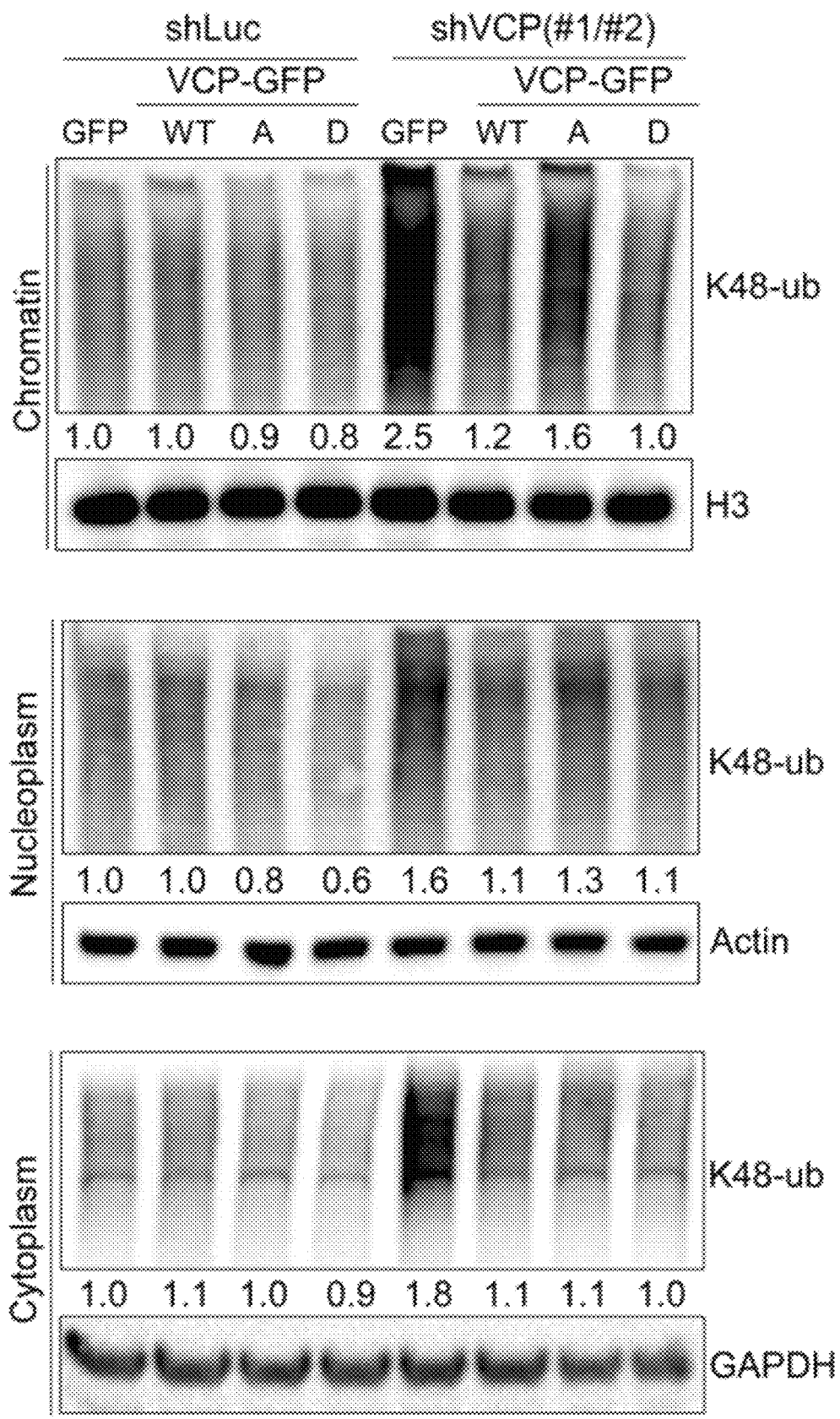
Figure 13A:
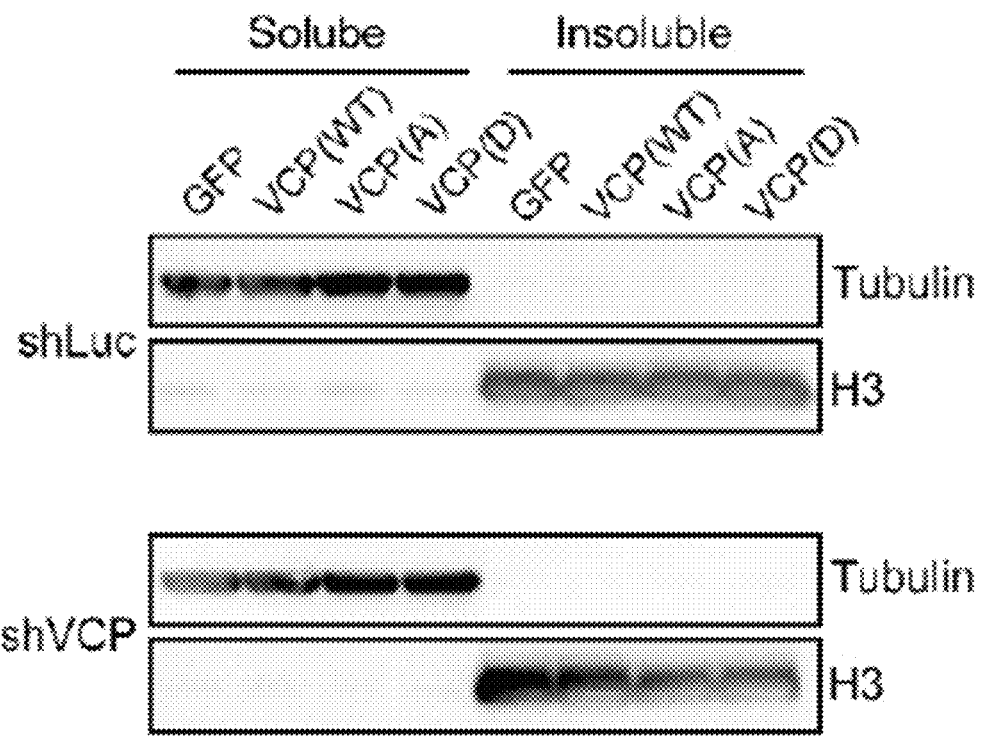
FIG. 13A-13I show Effects of Ser784 phosphorylation on VCP substrates.
Figure 13B:
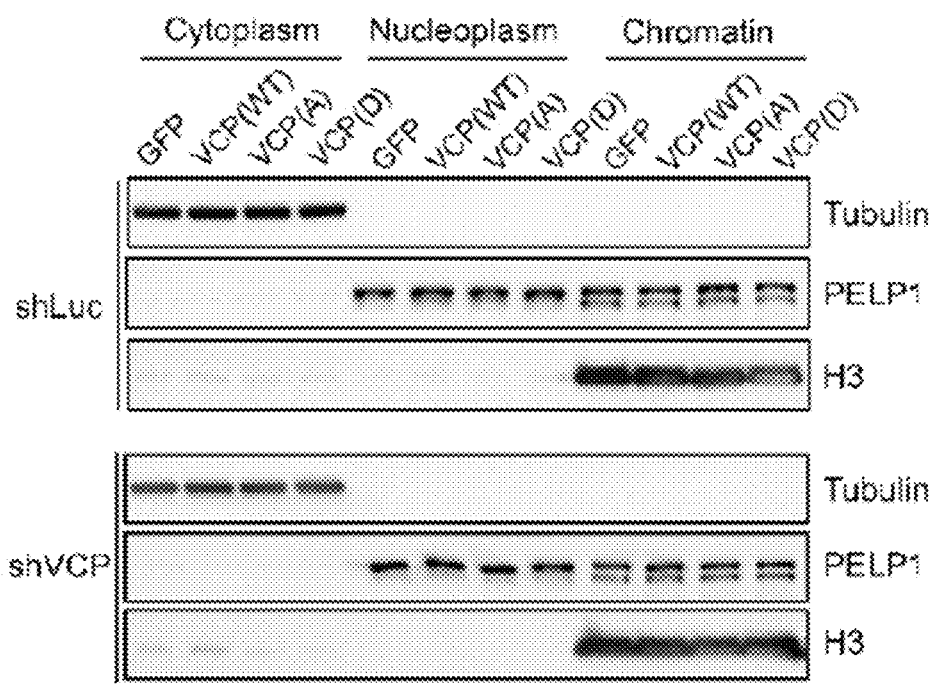
Figure 13C:
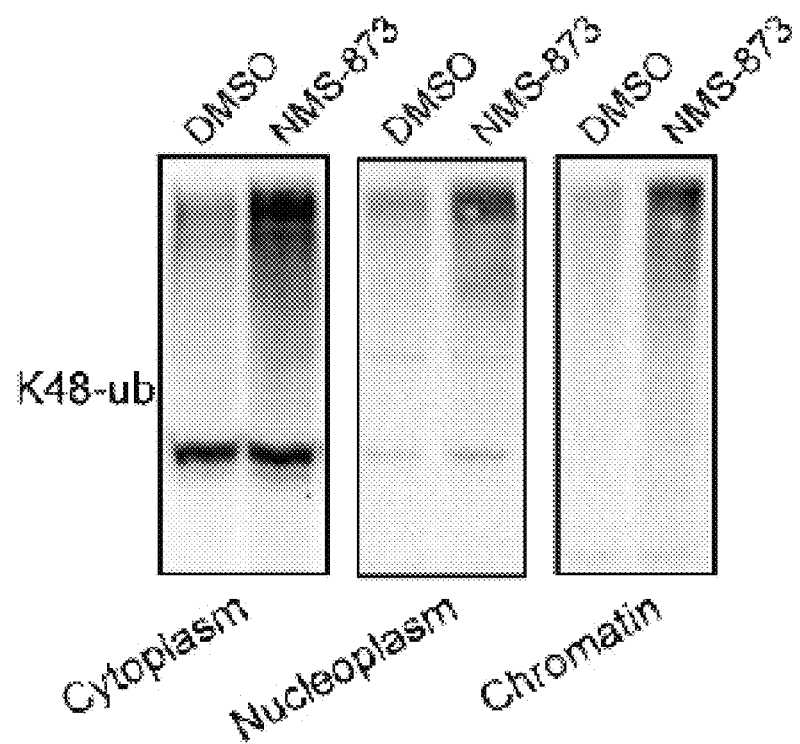
Figure 13D:
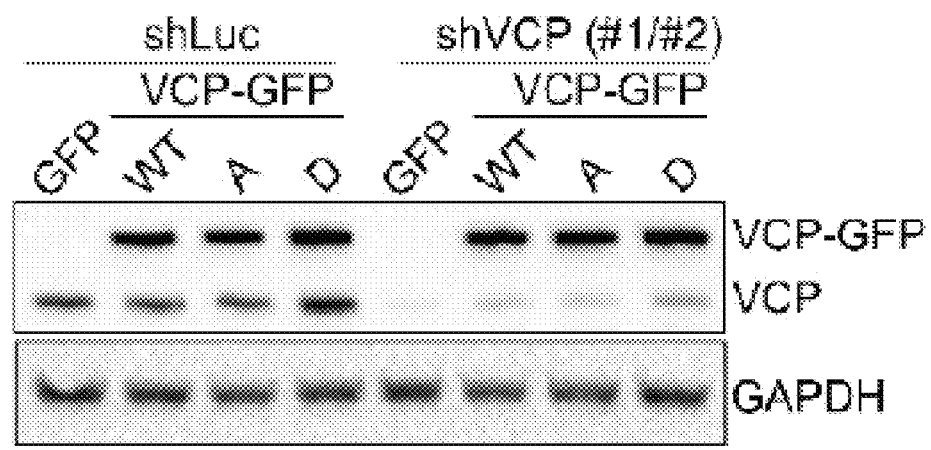
Figure 13E:
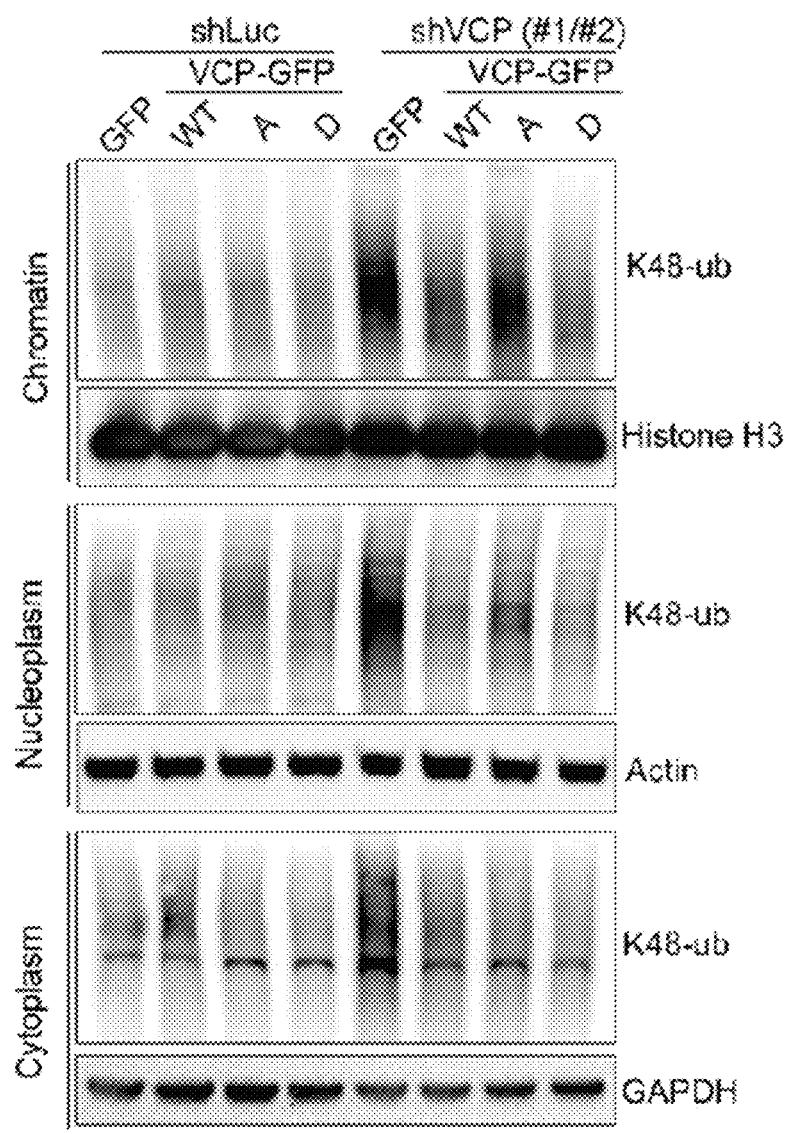

Ser784 Phosphorylation Increases VCP Activity on Chromatin: Given the essential function of VCP in the turnover of K48-polyubiquitinated proteins, it was asked whether Ser784 phosphorylation has a role in these processes in response to DNA damage. The S784A and S784D mutations were used to mimic the unphosphorylated and phosphorylated forms of VCP, respectively. They were introduced into a human VCP-GFP construct containing silent mutations, which confer resistance to two different shRNAs (shVCP 1 and 2). Wild-type and mutant VCP-GFP were stably expressed in Hela cells at similar levels to each other and relative to endogenous VCP (FIG. 5A). Upon VCP knockdown in the etoposide-treated GFP control cells, the level of K48-polyubiquitinated proteins increased significantly, both in the RIPA-soluble and insoluble fractions (FIGS. 5B and S7A). Interestingly, although the increase in the soluble fractions was similarly rescued by wild-type and mutant VCP-GFP, the increase in the insoluble fractions was rescued more effectively by VCP (S784D) and less effectively by VCP (S784A) compared with VCP (WT) (FIG. 5B). To test whether the K48-polyubiquitin signals in the RIPA-insoluble fractions represent chromatin-associated proteins, we divided the cells into cytoplasm, nucleoplasm, and chromatin fractions. VCP knockdown increased K48-polyubiquitin in all three fractions, consistent with its importance in global protein clearance (FIG. 12C and FIG. 13B). This was phenocopied by the specific VCP inhibitor NMS-873 (FIG. 13C). Interestingly, the most notable differences between the rescuing activity of VCP (S784D) (more active) and VCP (S784A) (less active) relative to VCP (WT) were detected in the chromatin fractions, followed by subtle differences in the nucleoplasmic fractions. No difference in the activity of wild-type versus mutant VCP was detected in the cytoplasmic fraction (FIG. 12C and FIG. 13B). Similar results were also observed in the U2OS cells (FIG. 13D and FIG. 13E).

Figure 12D:
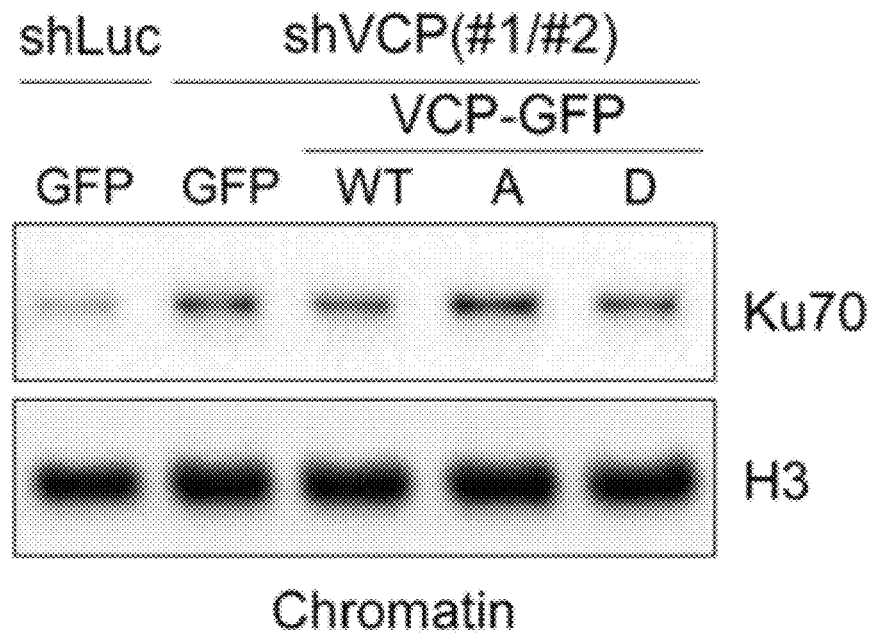
Figure 12E:
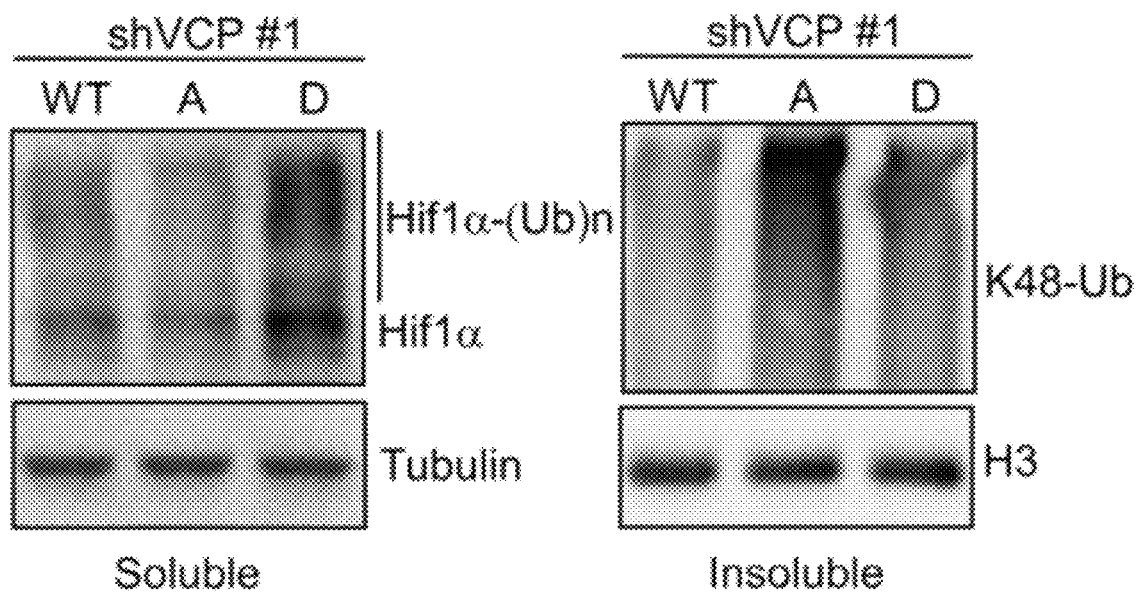
Figure 13F:
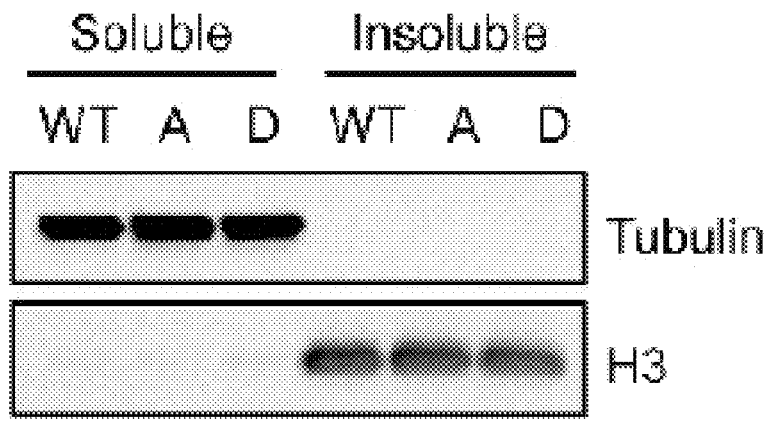
Figure 13G:
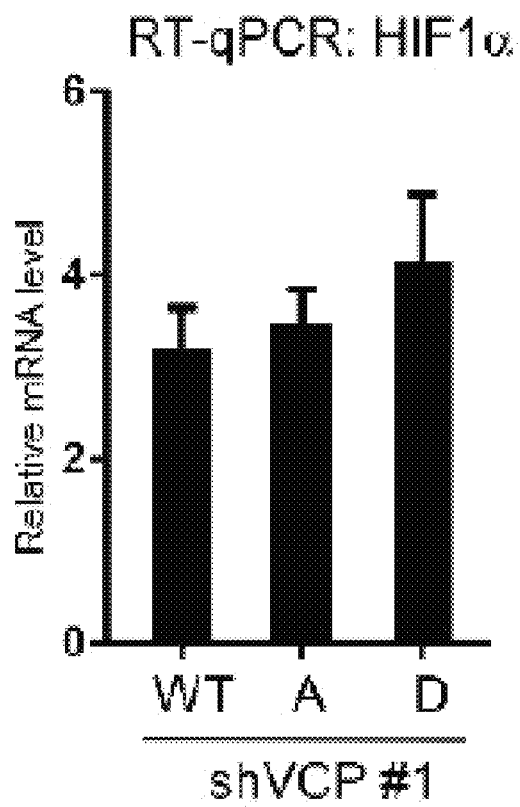

To confirm that the observed changes in K48-polyubiquitin represented VCP substrates, Ku70 was examined, the dimeric partner of Ku80, which is a known chromatin-associated VCP substrate essential for DSB repair. Chromatin-associated Ku70 level was increased by VCP knockdown in etoposide-treated HeLa cells, and that could be reduced by RNAi-resistant VCP (WT) and VCP (S784D) but not VCP (S784A) (FIG. 12D). Next, the level of HIF1α, a known soluble nuclear substrate of VCP was examined. Because of the high turnover rate of HIF1α under normal conditions, cells were treated with MG-132 for 2 h to reduce their proteasomal degradation before harvest. Interestingly, the level of RIPA-soluble HIF1α was significantly decreased by VCP (S784A) but increased by VCP (S784D) relative to VCP (WT), in clear contrast to the K48-ubiquitin levels in the insoluble fractions (FIG. 12E and FIG. 13F). qRT-PCR showed no changes in the mRNA level of HIF1α (FIG. 13G). These results suggest that Ser784 phosphorylation, induced by DNA damage, preferentially increases nuclear VCP ability to clear chromatin-associated but not soluble substrates.

Figure 14A:
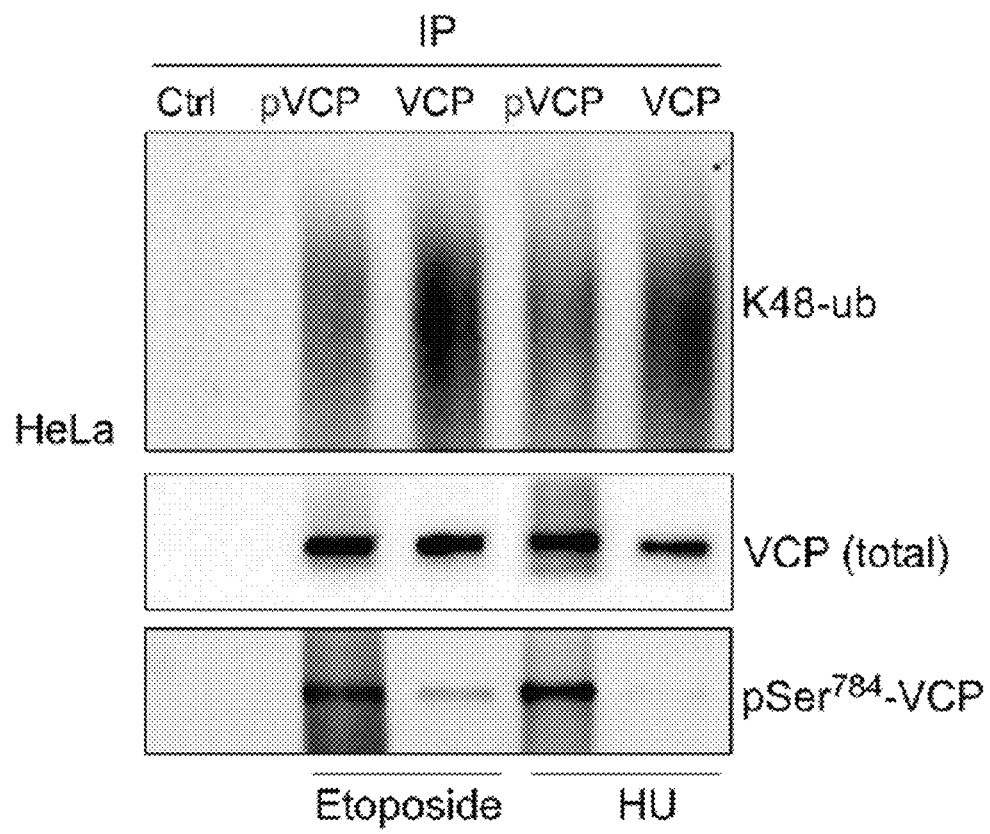
FIG. 14A-14D show Ser784 phosphorylation reduces VCP interaction with cofactors NPL4/UFD1 and K48-polyubiquinated proteins.
Figure 14B:
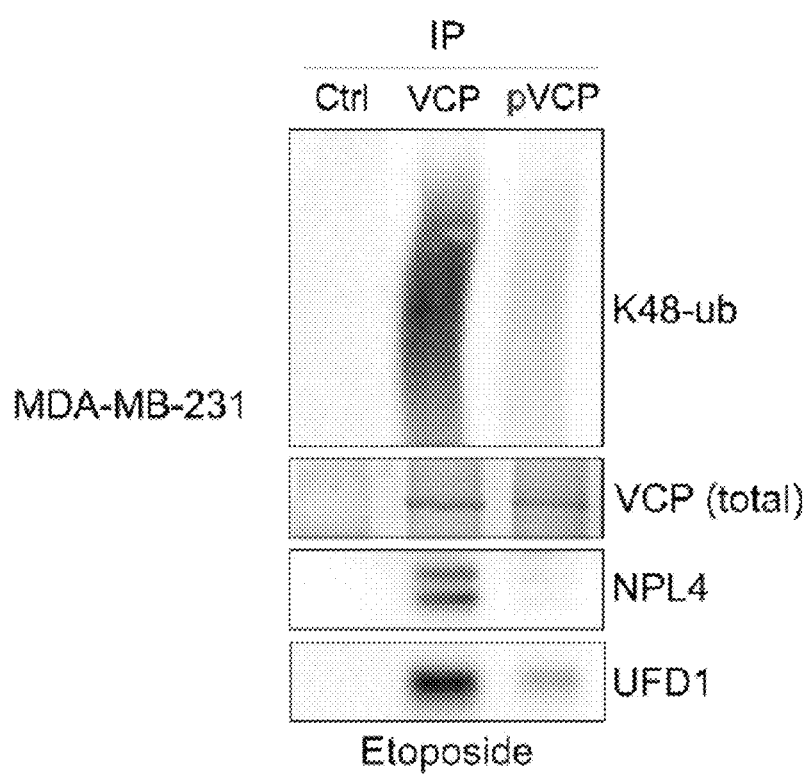
Figure 14C:
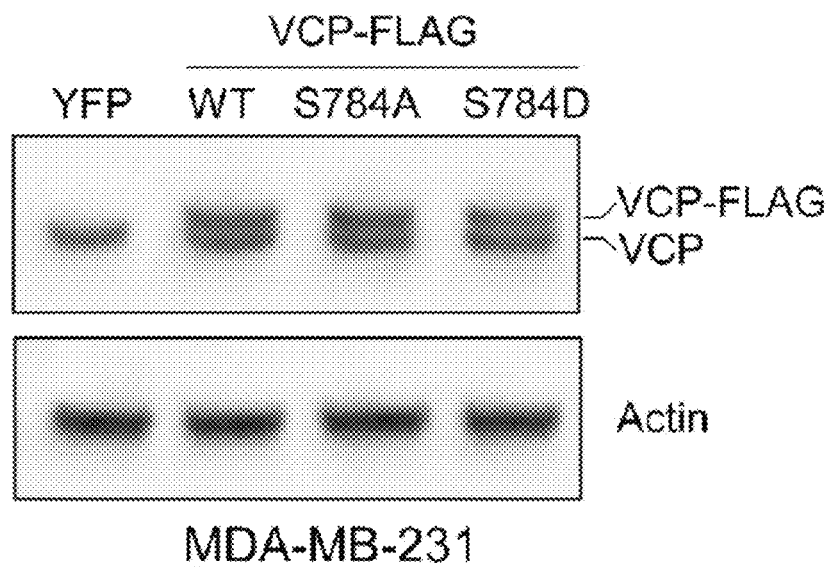
Figure 15A:
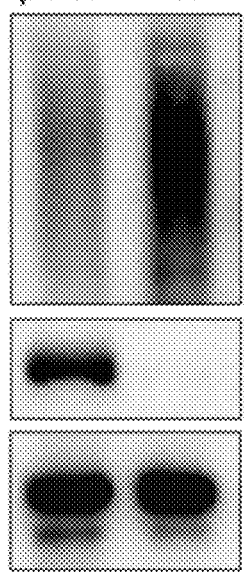
FIG. 15A-15D show Ser784 phosphorylation decreases VCP association with chromatin and polyubiquitinated proteins.
Figure 15A:
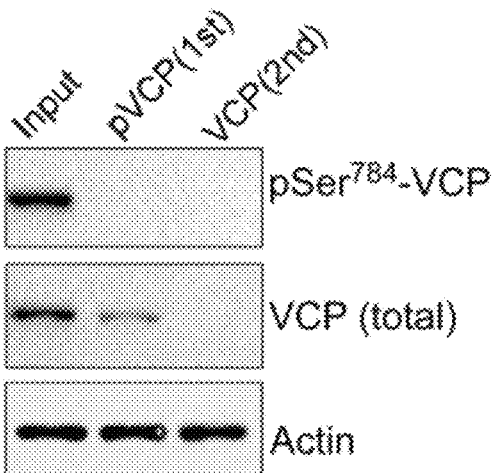
Figure 15B:
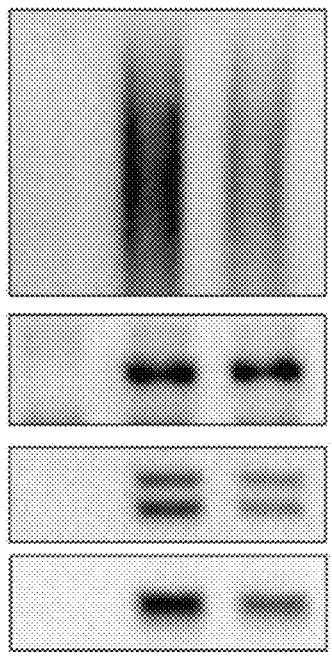

Ser784 Phosphorylation Decreases VCP Association with NPL4/UFD1 and Polyubiquitinated Proteins: To study the regulatory mechanism of Ser784 phosphorylation, the effects on the VCP interaction with protein substrates were first examined. Total VCP (by a pan-VCP antibody) or pSer$^{784}$-VCP (by 3E4) from etoposide or HU-treated HeLa cell lysates were immunoprecipitated and immunoblotted for co-absorbed K48-polyubiquitinated proteins. Despite the similar amounts of precipitated VCP, 3E4 significantly enriched pSer$^{784}$-VCP compared with the pan-VCP antibody. Interestingly, less K48-polyubiquitins were co-adsorbed by 3E4 than by the pan-VCP antibody, indicating that Ser784 phosphorylation may reduce VCP interaction with substrates (FIG. 14A). To better separate pSer$^{784}$-VCP from unphosphorylated VCP, sequential pull-downs were performed from etoposide-treated HeLa cell lysates to first deplete pSer784-VCP using 3E4 and subsequently capture the remaining unphosphorylated VCP by the pan-antibody. Significantly less binding of K48-polyubiquitins were detected to pSer$^{784}$-VCP than of unphosphorylated VCP. Based on the levels of VCP in the input and supernatants after each pull-down, it is evident that Ser784 is phosphorylated at high stoichiometry in response to DNA damage (>50% of total VCP after overnight etoposide treatment) (FIG. 15A). The reduced binding of K48-polyubiquitins by pSer$^{784}$-VCP was similarly observed in etoposide-treated MDA-MB-231 cells (FIG. 14B) and was recapitulated by S784D versus S784A mutants of VCP-FLAG (FIG. 15B). Interestingly, VCP interaction with NPL4 and UFD1, two core cofactors important for K48-polyubiquitin binding during chromatin-associated degradation, is similarly decreased by Ser784 phosphorylation (FIG. 15B and FIG. 14B).

Figure 13H:
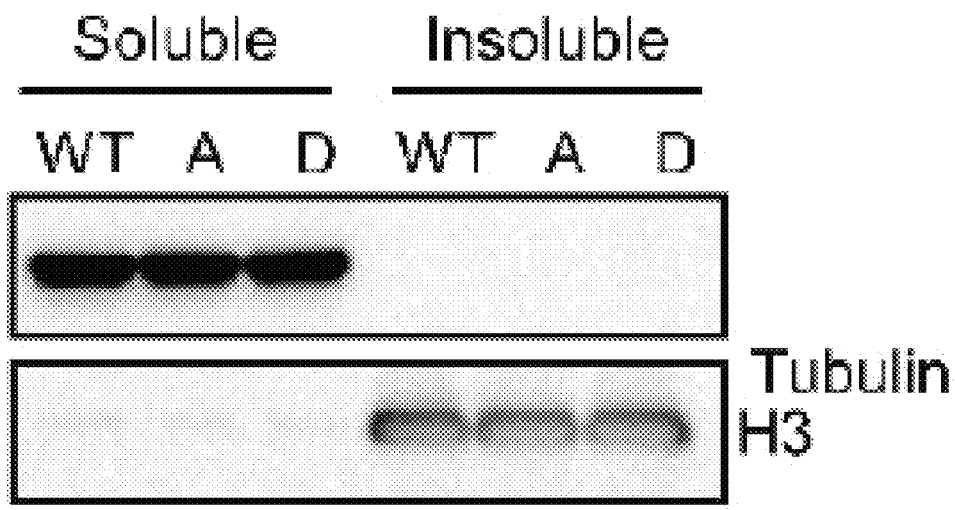
Figure 13I:
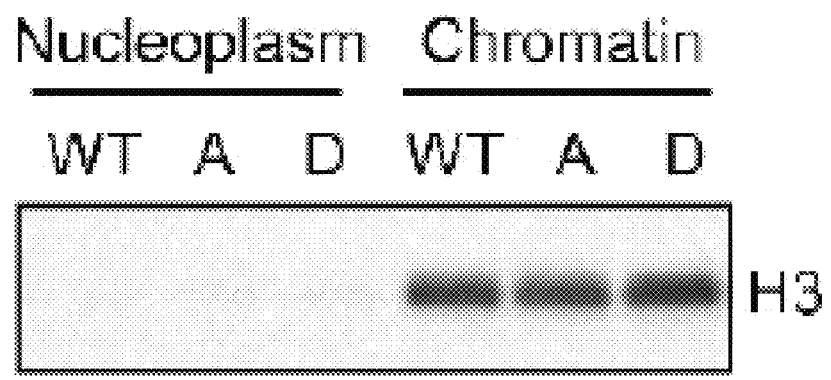
Figure 14D:
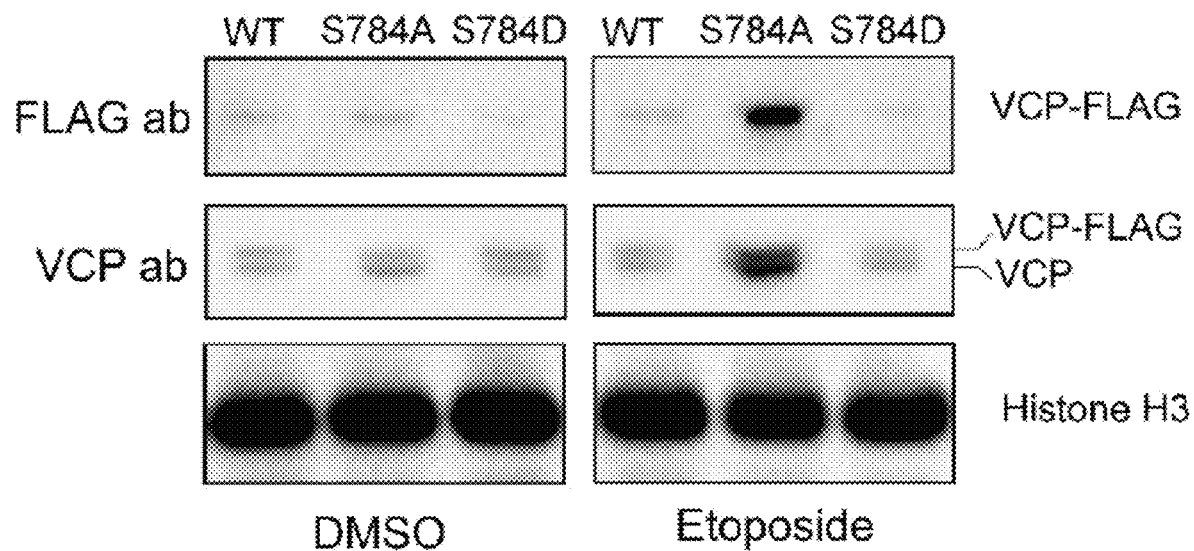
Figure 15C:
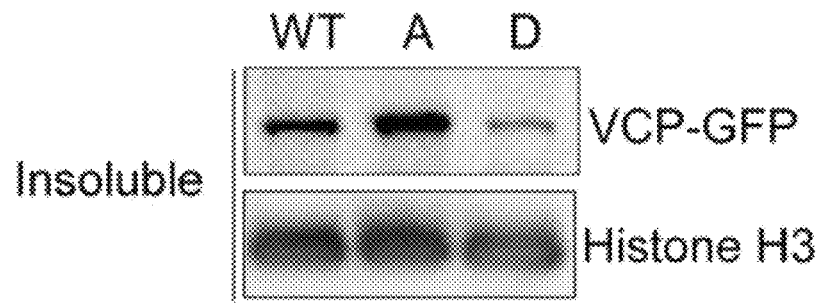
Figure 15C:
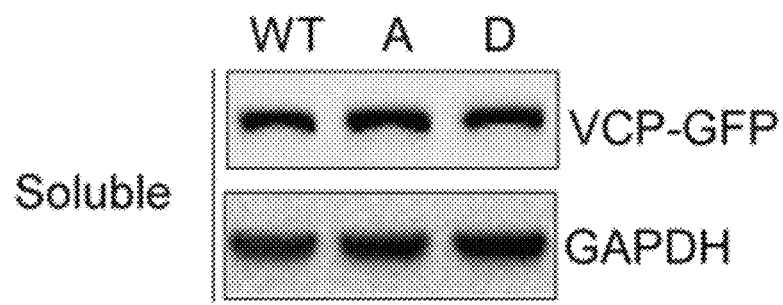
Figure 15D:
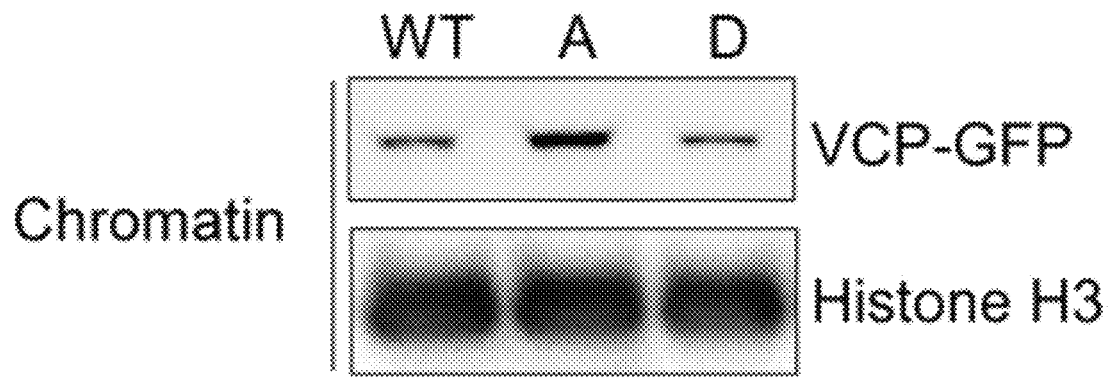
Figure 15D:
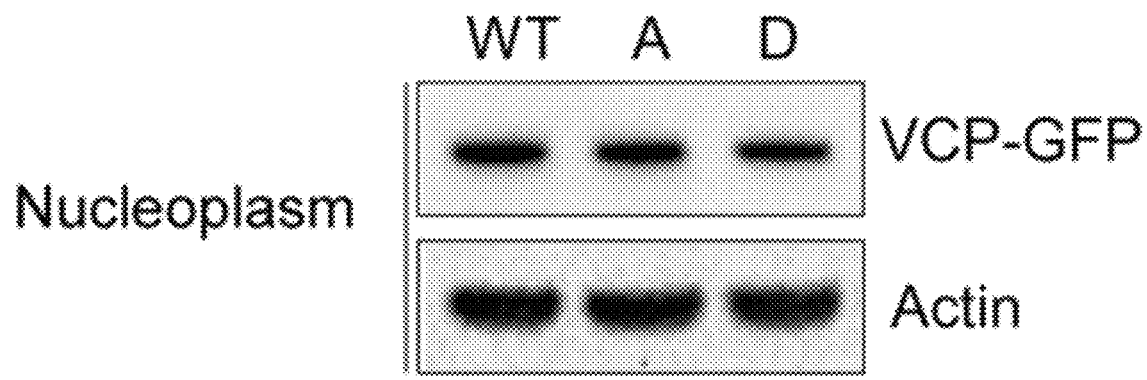

Next, the effect of Ser784 phosphorylation on VCP association with chromatin was examined. S784A mutation significantly increased VCP level in RIPA-insoluble, chromatin-enriched fractions of etoposide-treated VCP knockdown and rescue Hela cells. Conversely, S784D caused a decrease of RIPA-insoluble VCP (FIG. 15C and FIG. 13H). Consistent with that, subcellular fractionation showed more chromatin-associated VCP (S784A) than VCP (WT) and VCP (S784D) did, despite their similar nucleoplasmic levels (FIG. 15D and FIG. 13I). Similar results were also observed in etoposide-treated MDA-MB-231 cells expressing wild-type and mutant VCP-FLAG (FIG. 15C and FIG. 14D). Thus, the increased chromatin-selective activity of pSer784-VCP appears to correlate with decreased association with NPL4/UFD1 and polyubiquitinated substrates.

Figure 16A:
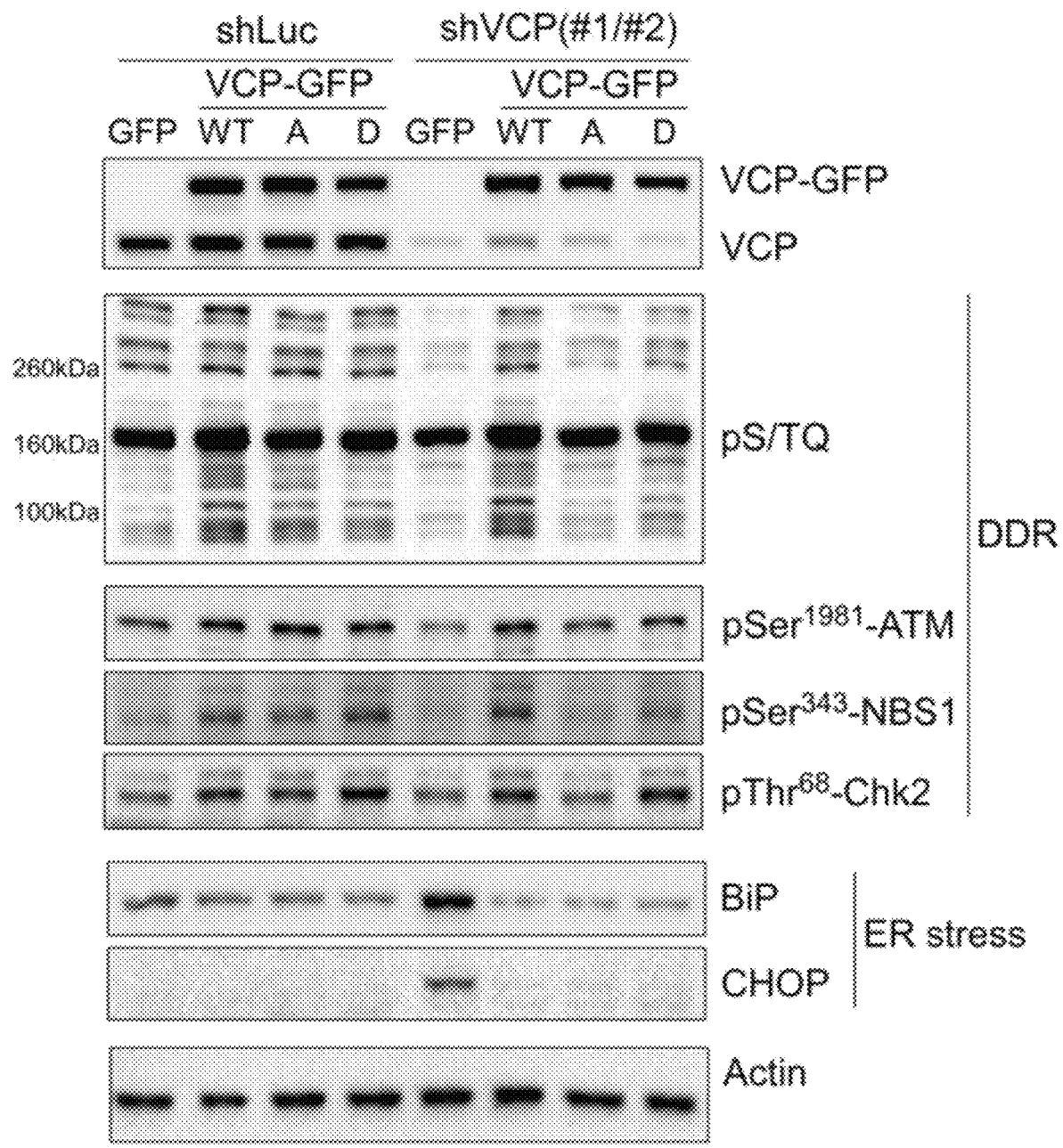
FIG. 16A-16D show Ser784 phosphorylation of VCP is important for DNA-Damage response and cell survival upon genotoxic stress.
Figure 17A:
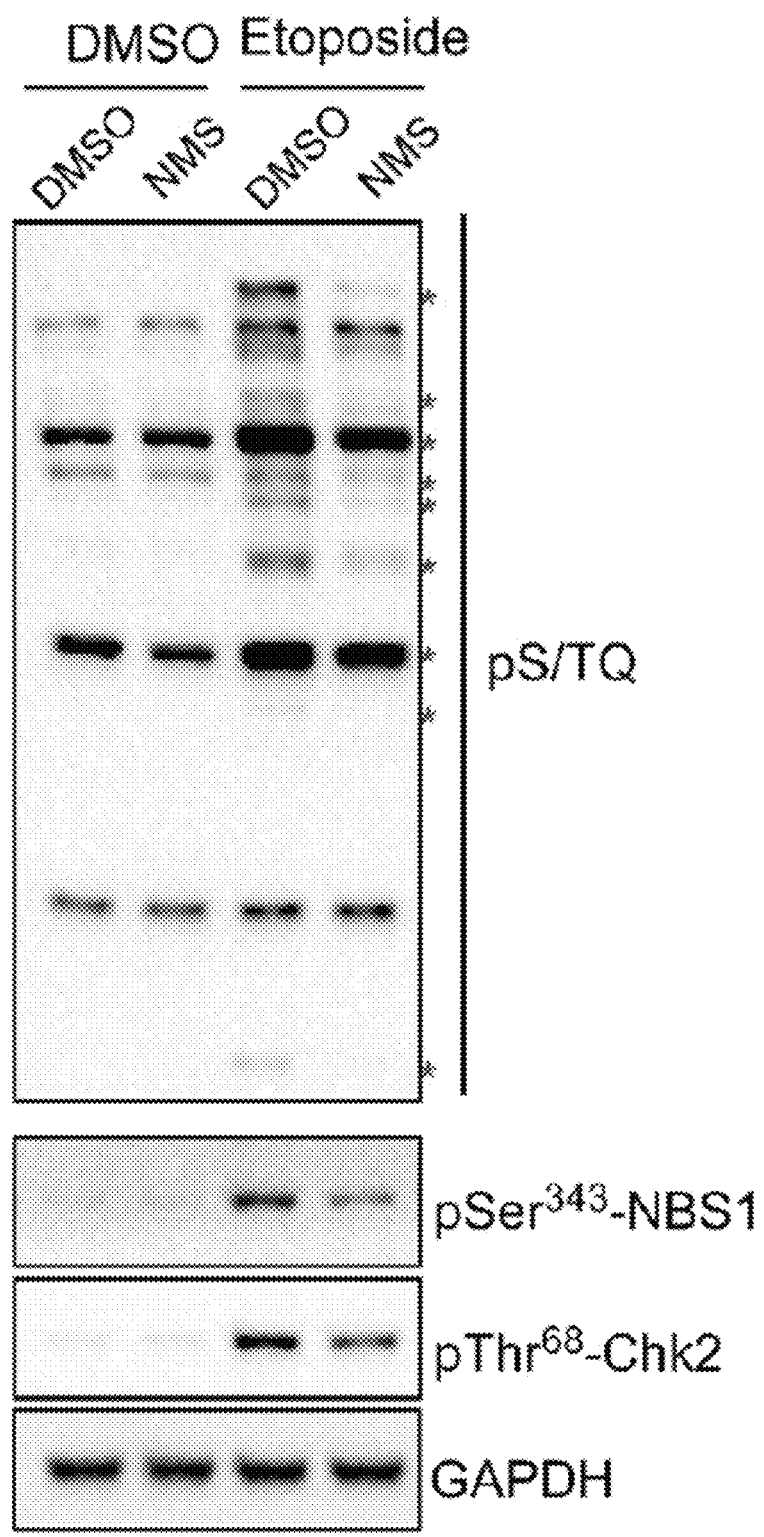
FIG. 17A-17F show the effects of Ser784 phosphorylation of VCP on PIKK signaling.
Figure 17B:
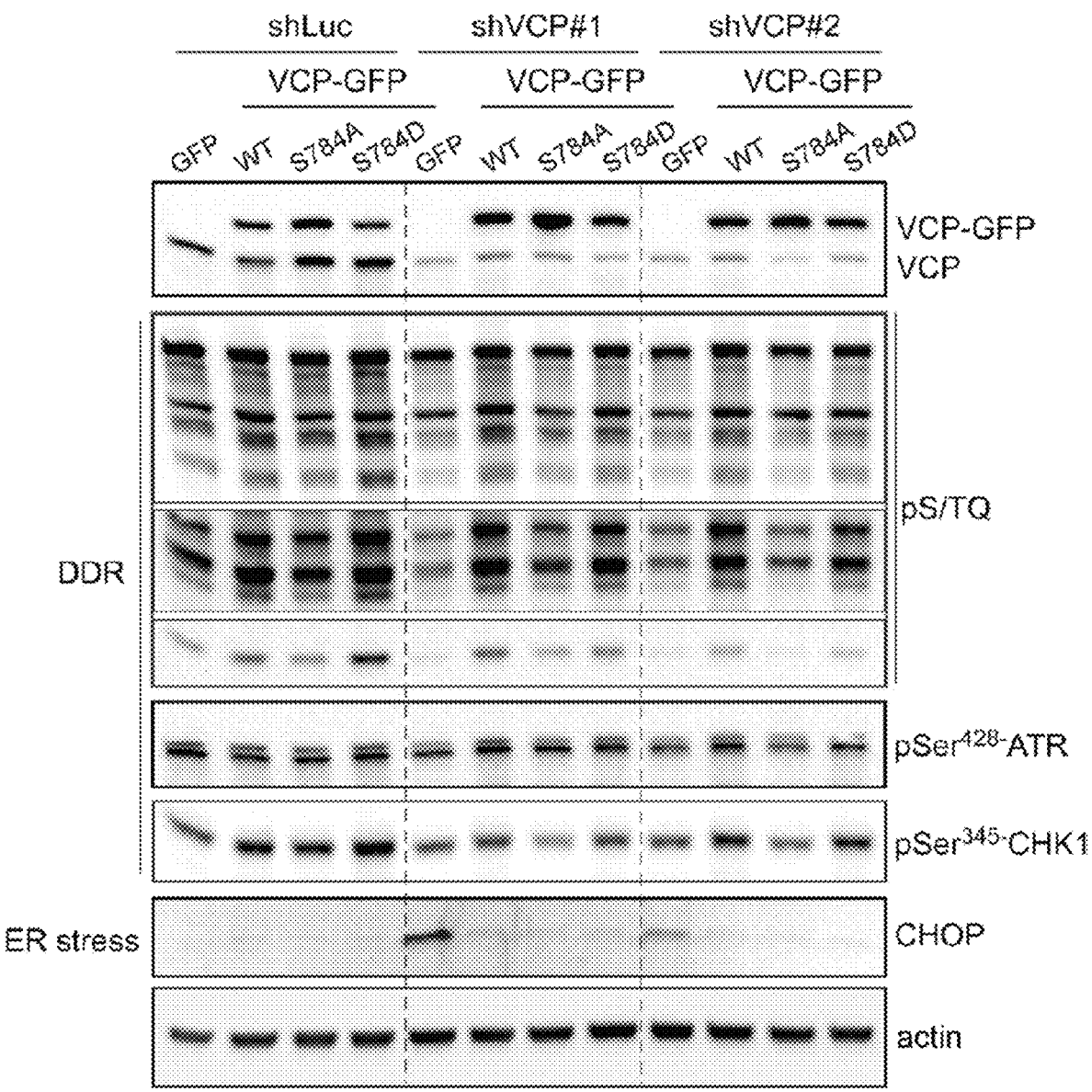

Ser784 Phosphorylation of VCP Is Important for DNA-Damage Response and Cell Survival upon Genotoxic Stress: To determine the functional significance of Ser784 phosphorylation for DNA-damage response, VCP knockdown and rescue was performed in etoposide-treated Hela cells, as described in FIG. 12. First, DDR signaling was examined by quantifying the phosphorylation events of the PIKK kinases. Using an antibody against the consensus pS/TQ motif and two well-known ATM substrates pSer343-NBS1 and pThr68-Chk2 functionally important for DSB repair and cell cycle checkpoint, a significant decrease in PIKK signaling upon VCP knockdown were detected within RIPA-soluble fractions (in GFP control cells), which was fully rescued by wild-type VCP (FIG. 16A). Chemical inhibition of VCP by NMS-873 similarly decreased PIKK signaling (FIG. 17A). Interestingly, although VCP (S784D) showed similar rescuing activity as VCP (WT) did, VCP (S784A) was nearly inactive (FIG. 16A). Similar results were observed in HU-treated Hela cells (FIG. 17B). In contrast, the increase in endoplasmic reticulum stress, indicated by Bip1 and CHOP induction, as a result of VCP knockdown can be fully rescued by both wild-type and mutant VCP (FIG. 16A), consistent with their similar abilities to clear cytosolic polyubiquitinated proteins (FIG. 12B).

Figure 17C:
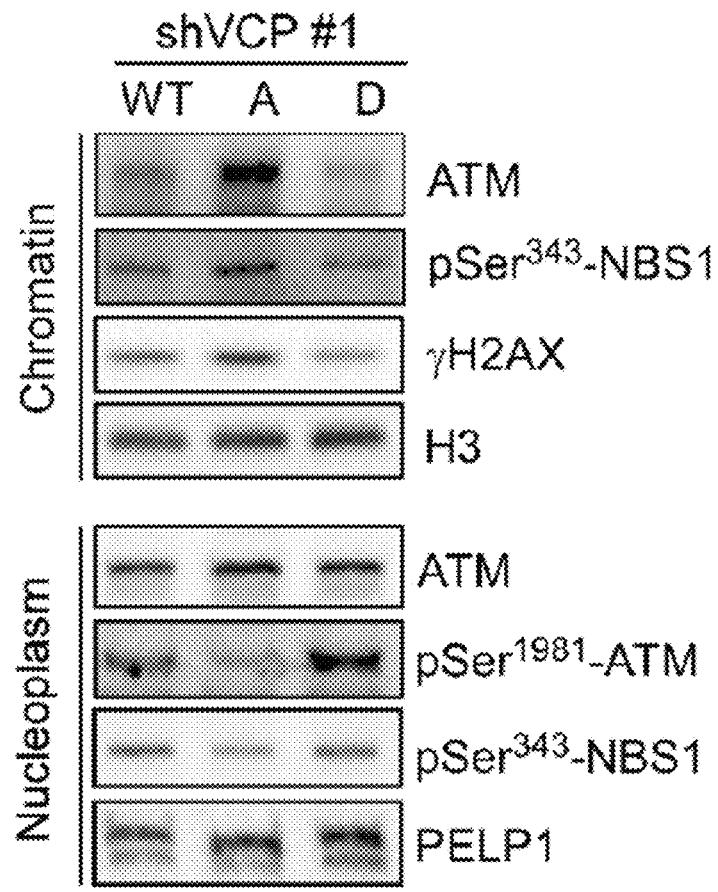
Figure 17D:
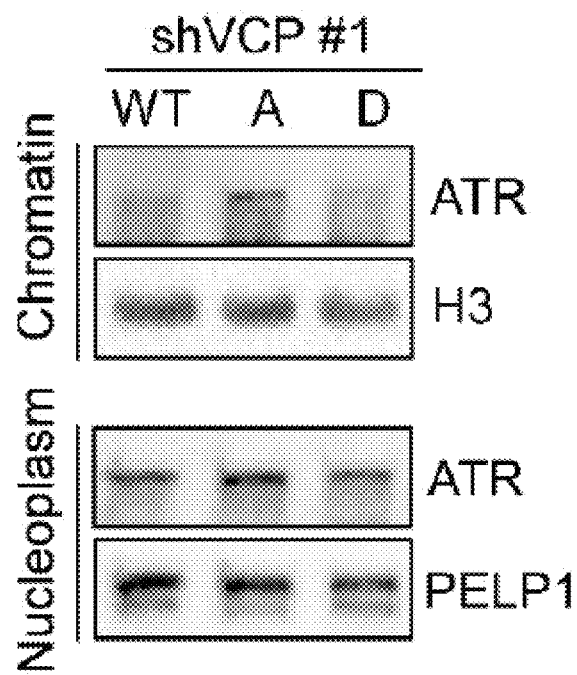
Figure 17E:
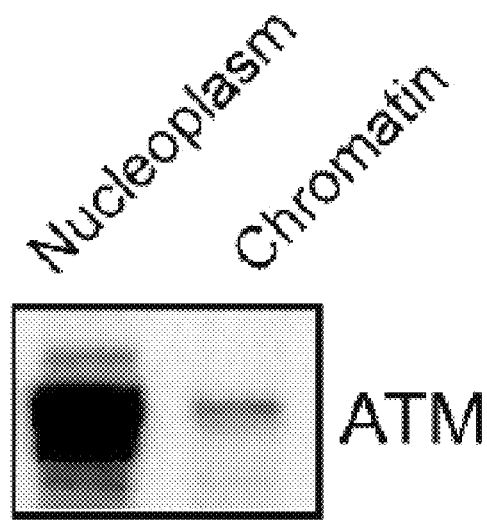
Figure 17F:
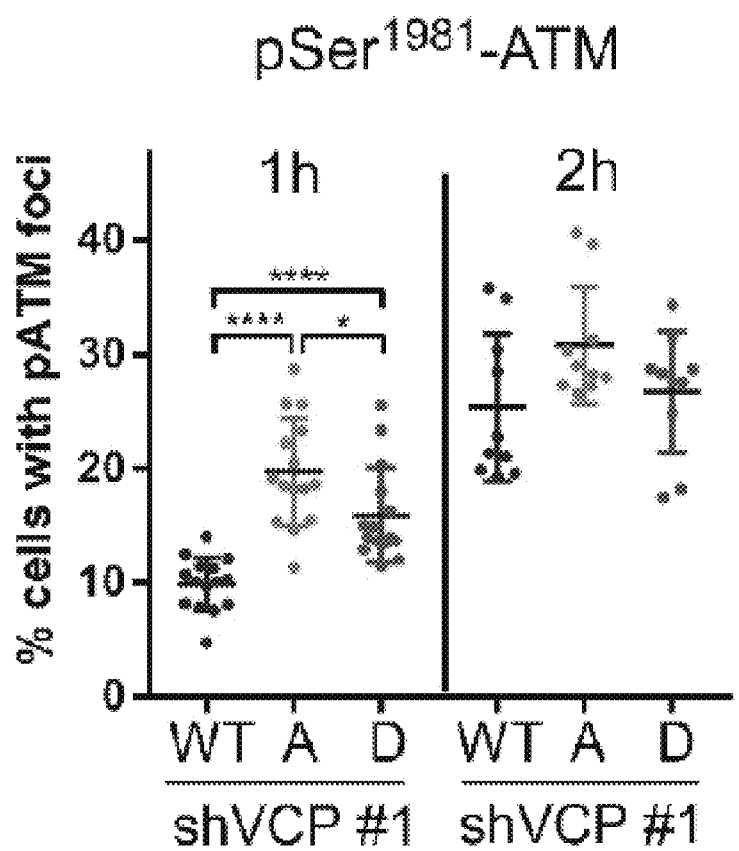

Next, it was tested whether Ser784 phosphorylation of VCP regulates PIKK signaling by affecting its chromatin binding upon DNA damage. Unexpectedly, in the etoposide or HU-treated VCP knockdown Hela cells rescued by VCP (S784A), more chromatin-associated ATM and ATR were detected, respectively, than in the cells expressing VCP (WT) and VCP (S784D) (FIGS. 17C and 17D). Higher levels of phosphorylated ATM substrates, pSer343-NBS1 and γH2AX, are found in chromatin fractions of the VCP (S784A) cells (FIG. 17C). This is in contrast to the reduced pSer1981-ATM and pSer343-NBS1 in the soluble nucleoplasm of VCP (S784A) cells compared with those expressing VCP (WT) and VCP (S784D) (FIG. 17C). We could not detect pSer1981-ATM in the chromatin fractions, possibly because only a small fraction of total ATM is retained on chromatin after fractionation (FIG. 17E). Nonetheless, immunostaining revealed more VCP (S784A)-rescued cells containing pSer1981-ATM-positive DNA-damage foci (FIG. 17F). Thus, Ser784 phosphorylation of VCP appears to differentially affect PIKK signaling within DNA-damage sites on chromatin versus in the soluble nucleoplasm.

Figure 16B:
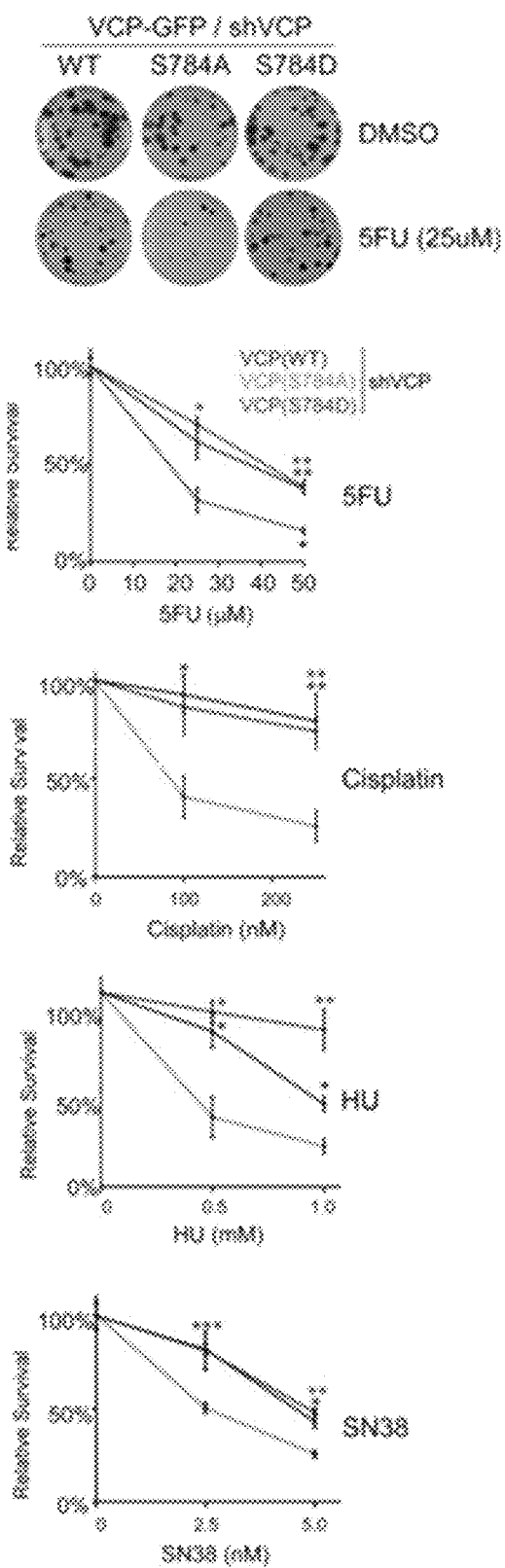
Figure 18A:
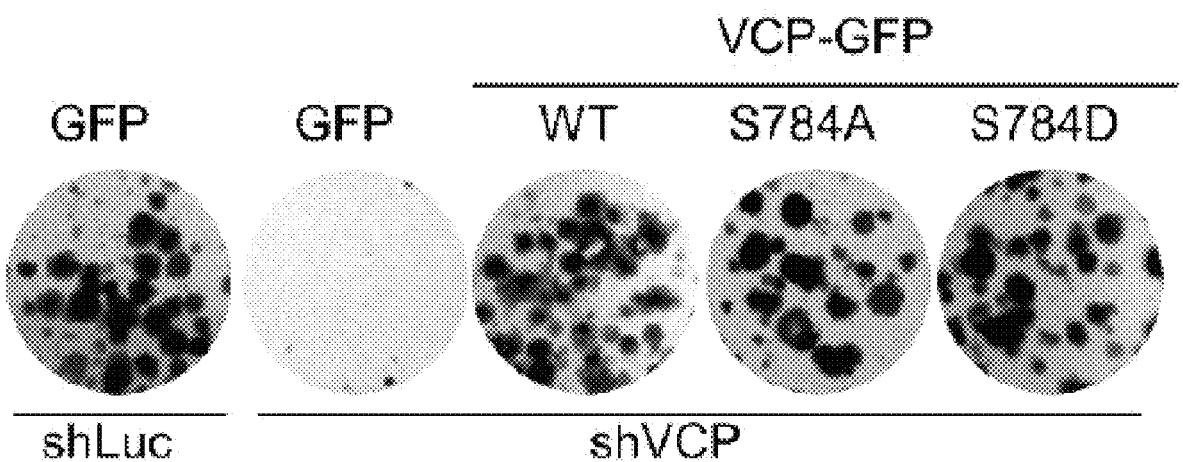
FIG. 18A-18D show Ser784 phosphorylation is important for VCP function specifically in the presence of genotoxic stress.
Figure 18B:
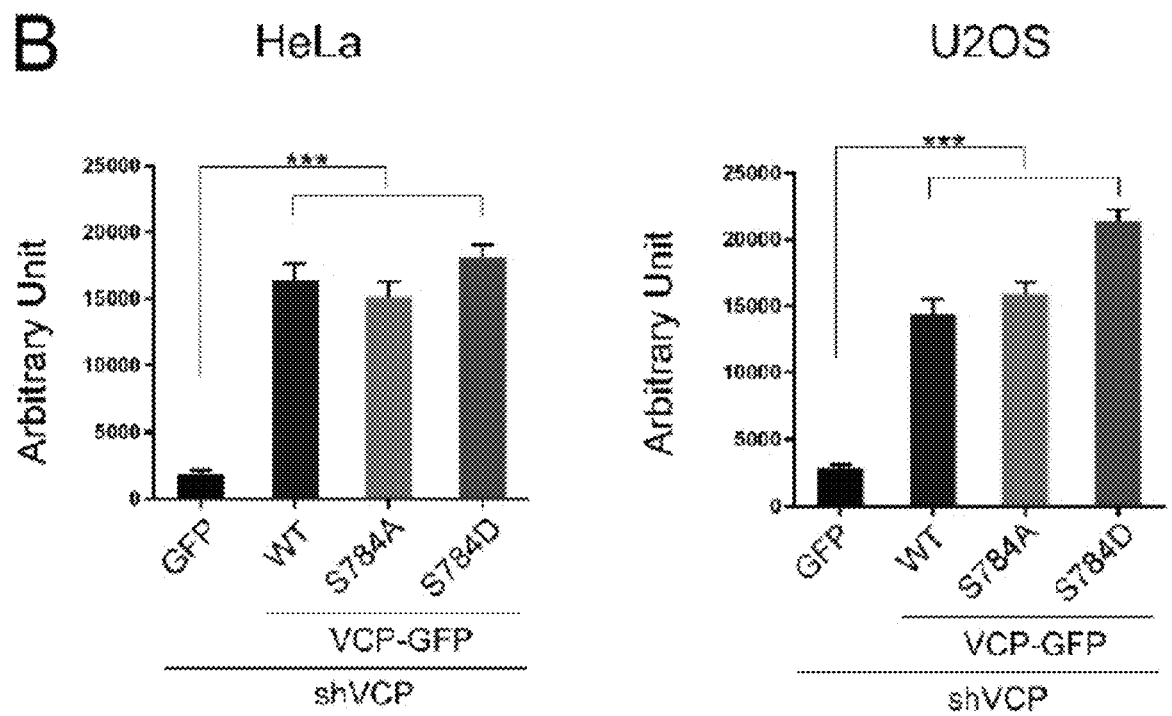
Figure 18C:
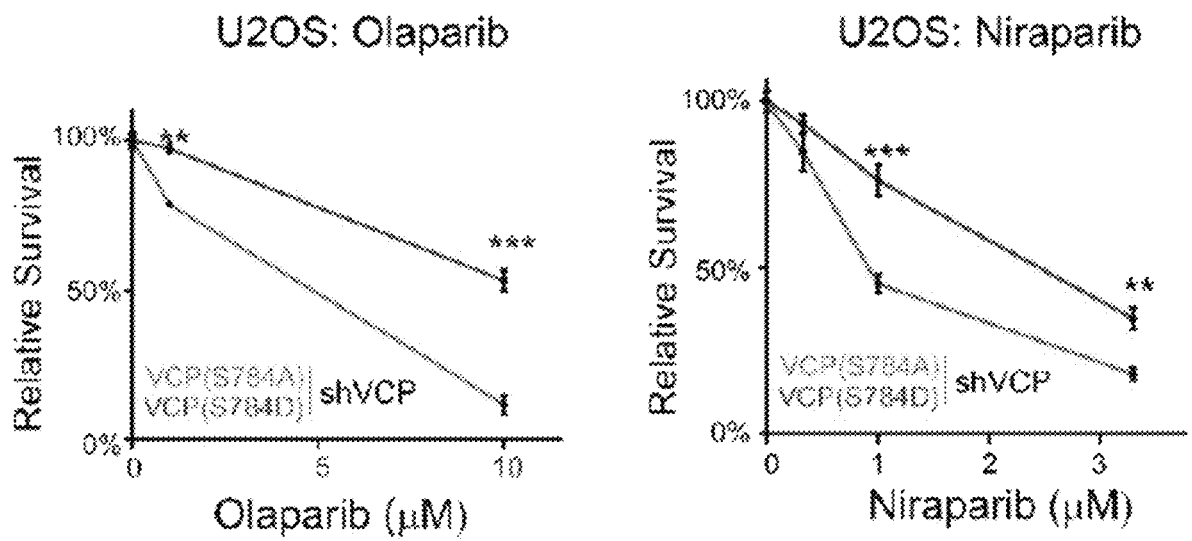
Figure 18D:
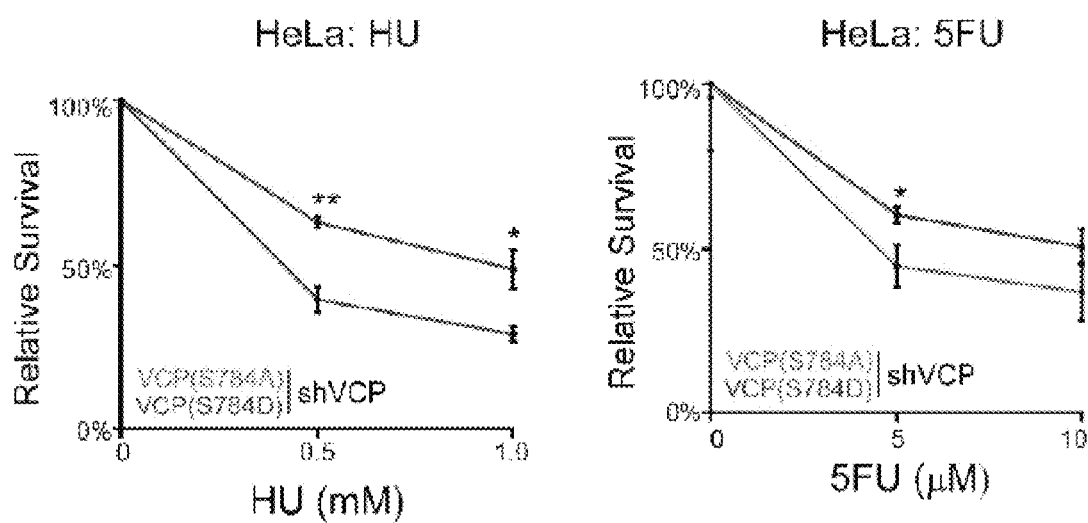

Next, whether Ser784 phosphorylation of VCP affects cell survival after DNA damage was investigated. Consistent with its essentiality, VCP knockdown caused cell death within 5-7 days without genotoxic stress, and that could be rescued by VCP, regardless of Ser784 mutations (FIGS. 18A and 18B). This enabled us to use the knockdown and rescue strategy (as in FIG. 12) to "replace" endogenous VCP with RNAi-resistant wild-type and mutant VCP and specifically to study the effect of Ser784 phosphorylation on DNA-damage-induced cell death. Treating the resultant U2OS cells with a panel of genotoxic agents (5FU, HU, cisplatin, SN38, and PARP inhibitors olaparib and niraparib) revealed that cells expressing VCP (S784A) survive significantly less than those expressing VCP (WT) and VCP (S784D) (FIG. 16B and FIG. 18C). Similar effects were also observed in Hela cells (FIG. 18D).

Figure 16C:
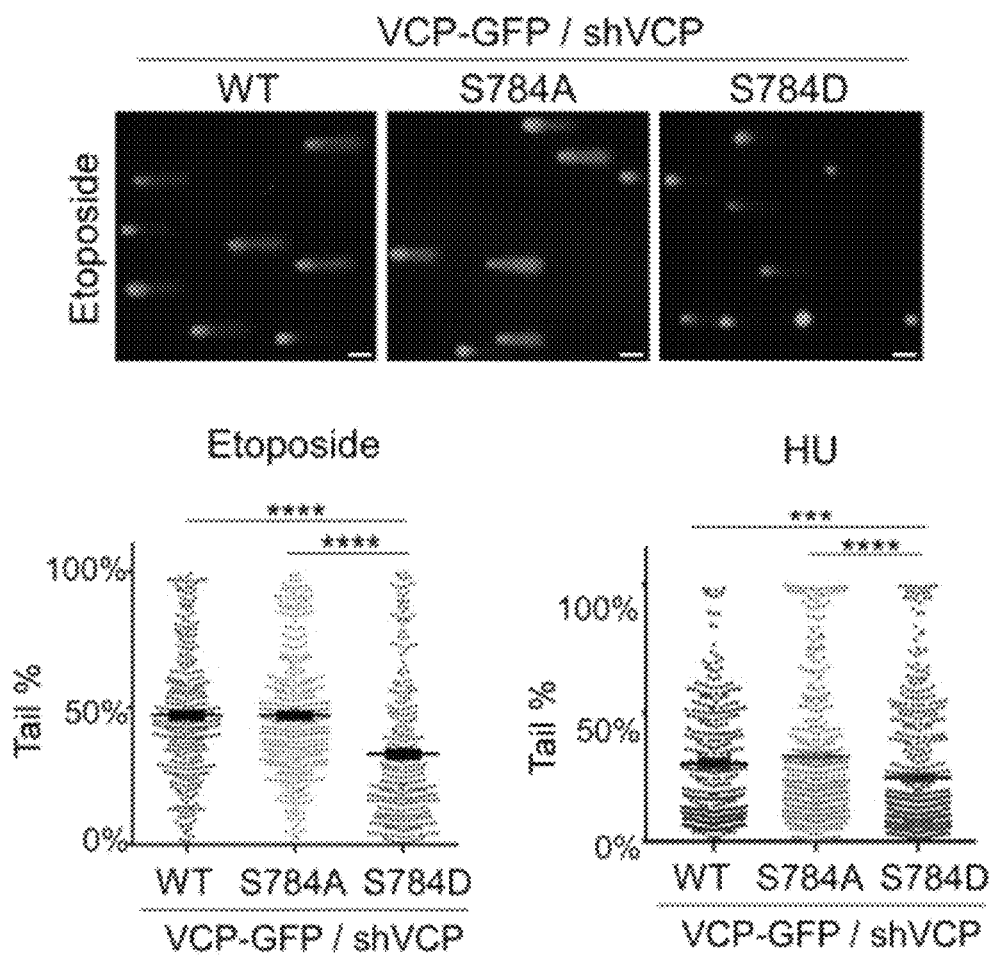

Last, we tested whether the pro-survival effect of pSer784-VCP upon genotoxic stress correlates with increased DNA-damage repair. We treated the VCP knockdown and rescue U2OS cells with etoposide and HU and used the comet assay to quantify single- and double-stranded DNA breaks under alkaline conditions. In response to both drugs, significantly fewer DNA breaks were detected in VCP (S784D) than detected in VCP (WT) and VCP (S784A) cells (FIG. 16C). Collectively, these results demonstrate the functional importance of VCP phosphorylation at Ser784 for DNA-damage repair, global PIKK-dependent DDR signaling, and cell survival, further supporting the idea that pSer$^{784}$-VCP may be used to predict the outcome of chemotherapy-treated patients with breast cancer.

Discussion

In this example, it was established that Ser784 phosphorylation is an important regulatory event of VCP, specifically for its nuclear DDR functions. This work was motivated by the serendipitous finding that an unknown nuclear phosphoprotein, cross-reacting with the pSer$^{137}$-Pfn1 antibody, significantly correlated with poor survival for breast cancer patients receiving genotoxic chemotherapies. This unexpected, yet clinically important, finding led to the identification of pSer$^{784}$-VCP as the underlying nuclear antigen and our subsequent investigation that revealed its functional importance for DDR.

Although several phosphorylation events of VCP have been reported, Ser784 is the only DNA-damage-induced phospho-site unbiasedly and independently detected by different studies. It was first described by Livingstone et al. Cancer Res. 2005; 65:7533-7540 (2005) in a similarly serendipitous fashion, using a cross-reacting phospho-Chk2 antibody, which detected pSer$^{784}$-VCP at DNA-damage foci in response to various genotoxic treatments. Subsequently, two unbiased proteomic studies independently confirmed Ser784 phosphorylation (the only detectable phospho-site on VCP) in response to IR and UV (Matsuoka et al., Science 316:1160-1166 2007, Stokes et al., Proc. Natl. Acad. Sci. USA. 2007). However, its physiological significance remained unknown before the present disclosure.

More than a decade later, the present disclosure provides clinical and mechanistic evidence for the functional importance of Ser784 phosphorylation in DDR. Clinically, the present example provides that the level of nuclear pSer$^{784}$-VCP, recognized by the cross-reacting pSer$^{137}$-Pfn1 antibody, is associated with poor outcome among patients with breast cancer who received genotoxic therapies (cyclophosphamide, methotrexate, 5FU, and anthracyclines) but not among those receiving the ER-antagonist tamoxifen or no adjuvant systemic therapy at all. Notably, pSer$^{784}$-VCP level used for our analysis is in the surgical tumor samples taken before the adjuvant treatments. In other words, it is the baseline pSer$^{784}$-VCP level induced by endogenous DNA damage that predicts the survival for patients subsequently treated with adjuvant genotoxic chemotherapy. However, discrepancy is conceivable between the "baseline" and the "drug-induced" pSer$^{784}$-VCP levels. For instance, certain tumors containing low levels of endogenous DNA damage would present low baseline pSer$^{784}$-VCP levels, but may phosphorylate Ser784 to high levels upon exogenous drug treatments. Thus, although valid, our data likely underestimates the true chemo-predictive ability of pSer$^{784}$-VCP. Future studies can better assess this by treating patients neoadjuvantly (before surgery) with genotoxic agents and staining biopsy samples for "induced" pSer$^{784}$-VCP to correlate with short-term neoadjuvant tumor response and long-term survival during or after adjuvant treatment. Moreover, because Ser784 phosphorylation occurs in cell lines derived from various tissues (FIGS. 7A and 7B) and protects them from a wide range of DNA-damaging agents, including PARP inhibitors (FIG. 16B), it is likely a general predictor of genotoxic chemotherapy susceptibility for a broad range of cancer types.

Although our data suggest that tumors containing low levels of "induced" pSer$^{784}$-VCP can be treated effectively by chemotherapy, they also implicate those containing high levels of pSer$^{784}$-VCP as perhaps being sensitized by PIKK inhibitors, such as those against ATM and ATR. Multiple ATM and ATR inhibitors have entered clinical trials for different cancer types as monotherapies or radio- and chemo-sensitizers, supported by strong preclinical data (Brandsma et al., Expert Opin. Investig. Drugs. 2017; 26:1341-1355, Durant et al., Sci. Adv. 2018; 4: eaat1719, Weber and Ryan, Pharmacol. Ther. 2015; 149:124-138). However, because both kinases phosphorylate hundreds of proteins upon DNA damage, identifying the "driver" substrates with the functional capability of determining cell fate is important. VCP may be one such candidate because it is phosphorylated by both kinases and protects genome stability against a broad range of insults (FIG. 16B, FIG. 18C, and FIG. 18D). Nevertheless, inhibiting VCP function pharmacologically triggers global proteostatic stress throughout the cell and will likely cause dose-limiting toxicity when used in patients. Instead, the present disclosure shows that nuclear, but not cytoplasmic, VCP can be selectively activated by ATM- and ATR-mediated Ser784 phosphorylation. Thus, pSer$^{784}$-VCP levels may be an indicator of cellular reliance on ATM and ATR activities, and inhibiting ATM and ATR in pSer$^{784}$-VCP-high tumors may be an effective chemo-sensitizing approach.

As a substrate of PIKKs, VCP is reciprocally important for PIKK activation upon DNA damage (FIG. 16A and FIG. 17B). Interestingly, this requires Ser784 phosphorylation in a context-dependent manner. Preventing Ser784 phosphorylation, although decreasing phosphorylation of soluble substrates of ATM/ATR, actually increases ATM/ATR presence and activity on chromatin (FIG. 17C-17F). Although somewhat surprising, this finding highlights the complexity of the regulatory mechanisms for PIKK signaling and suggests that the chromatin-associated and soluble signaling events can be differentially regulated. Ser784 phosphorylation may increase the ability of VCP to mobilize chromatin-activated PIKKs or increase their dynamic exchange between chromatin and nucleoplasm to more efficiently phosphorylate soluble substrates. Additionally, by increasing the ability of VCP to extract chromatin-associated substrates, such as KRAB-associated protein 1 (KAP1), Ser784 phosphorylation may promote the global chromatin relaxation necessary for fully activating ATM beyond the DNA-damage sites. As for ATR, because it is frequently activated at single and double DNA junctions during ATM-dependent DSB resections, similar regulatory mechanisms by pSer$^{784}$-VCP may exist as well.

Figure 16D:
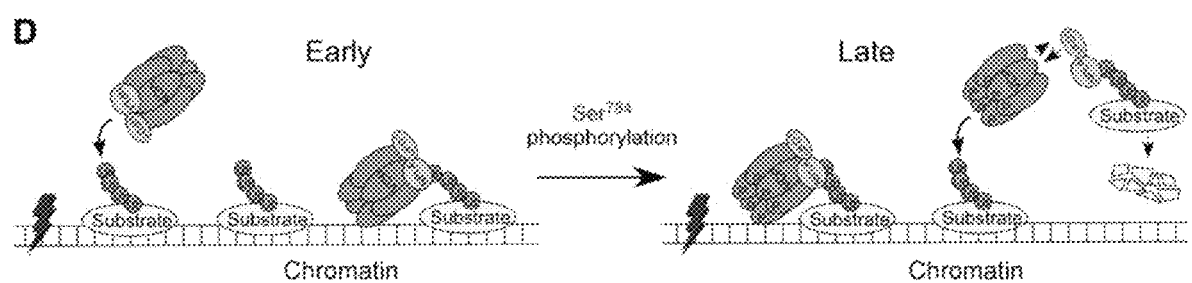

The finding that Ser$^{784}$ phosphorylation specifically increases VCP activity on chromatin is surprising, given that pSer$^{784}$-VCP interacts with NPL4/UFD1 with lower affinity (FIG. 15B and FIG. 14B). NPL4 and UFD1 are the core cofactors of VCP that directly bind polyubiquitins on many substrates and are important for chromatin-associated degradation. Thus, a reduced interaction with NPL4/UFD1 would be expected to inhibit VCP access to its substrates and can logically explain the higher level of HIF1α in cells expressing the phosphomimetic VCP (S784D) (FIG. 12E). However, the increased activity of pSer$^{784}$-VCP toward its chromatin-associated substrates seems counter-intuitive and mechanistically puzzling. In addition to the reduced interaction with NPL4/UFD1 and polyubiquitinated substrates, pSer$^{784}$-VCP also seems to associate with chromatin with less affinity, biochemically speaking (FIGS. 15C and 15D), but is readily detected at DNA-damage sites by immunostaining (FIG. 9G, FIG. 9H, and FIG. 10A). Based on all these data, the present disclosure provides that Ser784 phosphorylation may promote chromatin protein extraction by accelerating VCP dissociation from chromatin and NPL4/UFD1 to facilitate substrate release during the late stage of extraction (FIG. 16D). Indeed, phosphorylation triggers chromatin release of several known DDR factors, including KAP1, Rad9, and Chk1, each for a distinct purpose. However, the opposing effects of Ser784 phosphorylation on soluble (e.g., HIF1α) versus chromatin substrates of VCP and the clear presence of pSer$^{784}$-VCP at DNA-damage sites suggest the involvement of additional cofactors that enable chromatin access of pSer$^{784}$-VCP independently of NPL4/UFD1. An example of such cofactors during DNA-replication stress is DVC1, which delivers VCP to stalled replication forks to extract trans-lesion DNA polymerase.

The fact that Ser784 phosphorylation, within the C-terminal tail of VCP (763-806 amino acids [aa]), weakens the interaction with NPL4/UFD1 at the N-terminal domain suggests long-range conformational changes. Indeed, inter-domain communication is well-known for VCP and crucial for its ATP-dependent segregase activity. For example, nucleotide binding and hydrolysis in the central ATPase domains alter the relative position of the N-terminal domain, which presumably produces the mechanical force during protein extraction. Conversely, conformation of the N-terminal domain and its occupancy by cofactors influence the enzymatic activity of the ATPase domains. The C-terminal tail of VCP is poorly understood, both structurally and functionally. However, it can directly interact with several proteins, including PNGase, PLAA/UFD3, and UFD2, although none has been linked to DDR. Interestingly, Tyr806 phosphorylation occurs in the C-terminal tail in response to T-cell receptor activation and abolishes the interaction with PNGase and PLAA. These studies raise the possibility that Ser784 phosphorylation, in response to DNA damage, may alter the local interaction of VCP with certain C-terminally associated proteins and, in turn, cause long-range a conformational change to weaken the binding of NPL4/UFD1 at the N terminus.

In summary, the present example provides clinical and experimental evidence that pSer$^{784}$-VCP is a cancer prognostic biomarker that can predict chemotherapy response because of its importance for DDR.

Methods

Experimental Model And Subject Details: All cell lines were originally purchased from ATCC. HeLa, HEK293T, and U2OS cells were grown in high glucose DMEM supplemented with 5% or 10% fetal bovine serum and 50 µg/mL gentamicin. MDA-MB-231, BT549, T47D, and HCC1806 were grown in RPMI 1640 containing 5% or 10% fetal bovine serum (FBS) with gentamicin and supplements (50 µg/mL gentamycin, 1 mM sodium pyruvate, 10 mM HEPES and glucose to 4.5 g/L). Transient transfection was performed using Fugene HD or Lipofectamine 2000. Lentiviruses were generated using HEK293T cells as previously described (Diamond et al., 2015). Stable HeLa and U2OS cells expressing GFP or VCP-GFP (WT and mutants) were generated by transfection, 2 weeks of G418 (0.8 µg/ml) selection, and FACS. Stable MDA-MB-231 cells expressing YFP-FLAG and VCP-FLAG (WT and mutants) were generated by viral lentivirus and puromycin selection.

Antibodies: Custom-made polyclonal rabbit pSer$^{137}$-Pfn1 antibody was generated previously. The monoclonal pSer$^{784}$-VCP antibody was custom generated by Genscript. Briefly, a peptide (GGAGPpSQGSGGGTGC (SEQ ID NO: 1), C-terminal cysteine was added) containing phospho-Ser784 of VCP was synthesized, KLH conjugated, used to immunize BALB/c mice. Two rounds of cell fusions were performed followed by screening of 20,000 clones by indirect ELISA (using the antigenic phospho-peptide and the control peptide without the phosphate on Ser784). Five positive clones were selected for subcloning and supernatants of each clone were tested for pSer$^{784}$-VCP specificity by western blot. One clone (3E4) was selected, expanded, and grown in serum-free hydridoma-SFM media (GIBCO, cat #12045-076) followed by purification using the HiTrap protein G column according to manufacturer's protocol (GE healthcare, cat #17040403). Commercial antibodies used for western blot include GFP (CST, #2956), VCP (Santa Cruz, sc-57492 and sc-136273), actin (Santa Cruz, sc-47778), GAPDH (Santa Cruz, sc-365062), histone H3 (CST, #4499), tubulin (Sigma, T9026), PELP1 (Bethyl, #A300-180A), γH2AX (CST, #9718), Ku70 (Santa Cruz, sc-17789), ATM (Santa Cruz, sc-377293), pSer1981-ATM (CST, #5883; Rockland, #200-301-400), pSer428-ATR (CST, #2853), ATR (CST, #13934), Chk2 (CST, #3440), pThr68-Chk2 (CST, #2197), pSer345-Chk1 (CST, #2348), NBS1 (CST, #14956), pSer343-NBS1 (CST, #3011), K48-ubiquitin (CST, #4289; CST, #8081), FLAG tag (BioLegend, #637301), NPL4 (Bethyl, #A304-102A), UFD1 (Bethyl, #A301-875A), CHOP (CST, #2895), BiP (CST, #3177), phospho-ATM/ATR substrate motif (CST, #6966), Pfn1 (CST, #3246), HIF1α (CST, #79233). Antibodies for immunofluorescence staining include BRCA1 (Santa Cruz, sc-6954), 53BP1 (BD Biosciences, #612522), γH2AX (CST, #9718), VCP (Santa Cruz, sc-57492), pSer1981-ATM (Rockland, #200-301-400) custom-made pSer$^{137}$-Pfn1, pSer$^{784}$-VCP, and NBS1 as previously described (You et al., 2005). Commercial antibodies for immunoprecipitation include VCP (sc-57492) and anti-FLAG M2 affinity gel (Sigma, A2220).

Drugs: Drugs were purchased from Selleckchem (NMS-873, S7285; Etoposide, S1225; KU55933, S1092; Niraparib, S7625; Olaparib, S1060; Cisplatin, S1166, Gemcitabine, S1714, MG-132, S2619), Sigma (Hydroxyurea, H8627; 5-Fluoracil, F6627; SN38, H1065).

DNA and shRNA constructs: Human VCP (wt)-GFP in the pEGFP-N1 vector was purchased from Addgene (#23971). VCP was digested out of pEGFP-N1 with BglII (5') and Age I (3') and cloned into the same sites in the lentiviral pFLRu-FH vector to generate VCP (wt)-FLAG-6His. S784A and S784D were introduced using Quick-Change site-directed mutagenesis. S784A sense primer: TGGAGCTGGCCCCGCTCAGGGCAGTGGA (SEQ ID NO: 2); antisense primer: TCCACTGCCCT-GAGCGGGGCCAGCTCCA (SEQ ID NO: 3). S784D sense primer: TGGAGCTGGCCCCGATCAGGGCAGTGGA (SEQ ID NO: 4); antisense primer: TCCACTGCCCT-GATCGGGGCCAGCTCCA (SEQ ID NO: 5). Two human VCP-specific shRNAs in the pLKO. 1 vector were purchased from the RNAi consortium at the Genome Institute at Washington University: CCTGATGT-GAAGTACGGCAAA (SEQ ID NO: 6) (#1) and AGG-GAGGTAGATATTGGAATT (SEQ ID NO: 7) (#2). To confer shRNA resistance, multiple synonymous mutations were introduced within the target sequences of VCP by Genewiz: CCAGACGTCAAATATGGTAAG (SEQ ID NO: 8) (#1) and CGCGAAGTTGAGATAGGAATT (SEQ ID NO: 9) (#2). Two human Pfn1-specific shRNAs were described previously.

Immunohistochemistry staining and scoring: Formalin-fixed and paraffin-embedded human breast cancer TMAs were purchased from US Biomax or custom generated as described previously. The UBC series refers to patients diagnosed with invasive breast cancer at the University of British Columbia hospitals between 1989 and 2002 as previously described. The BCCancer series was derived from 4543 samples from patients diagnosed with invasive breast cancer in the province of British Columbia in the period January 1986-September 1992. These cases are linked to well-annotated clinical data regarding age, staging, histology, pathological factors, long-term follow-up and information on adjuvant systemic therapy as previously published. Tissues were subjected to standard rehydration and antigen retrieval by boiling in 10 mM Tris-HCl, pH 9.0 for 10 min. Following quenching with 3% hydrogen peroxide for 10 min, they were washed with TBS/0.1% Tween 20 (TBST), and blocked for 1 hr at room temperature with 5% normal goat serum and 4% BSA in TBST, and incubated with the primary antibodies (pSer137-Pfn1 at 1:1000; pSer784-VCP at 1:50) in blocking buffer at 4° C. overnight. After TBST wash, they were incubated with HRP-conjugated secondary antibodies (SignalStain Boost IHC Detection Reagent Mouse, #8125 and rabbit, #8114) for 2 hr at room temperature, and washed with TBST. They were developed using the ImmPACT DAB kit (Vectorlabs, SK-4105), counterstained with hematoxylin, dehydrated, and mounted. Bright field images were taken on an upright BX51 fluorescence microscope using the CellSens software. Nuclear staining was scored using the Allred scoring system, defined as the sum of the scores for average intensity (0: non, 1: weak, 2: moderate, 3: strong) and proportion of positive nuclei (0: none, 1: <1%, 2:1-10%, 3: 10%-33%, 4:33-66%, 5: >67%) scores (Harvey et al., 1999).

Immunofluorescence staining and image acquisition: Cultured cells grown on plastic or poly-D-lysine-coated glass coverslips were treated with vehicle ($H_2O$ or DMSO) or DNA damaging agents (in $H_2O$ or DMSO) for various times, rinsed with PBS, and fixed by 4% paraformaldehyde at room temperature for 20 min. For detergent pre-extraction, cells were incubated with cytoskeletal buffer (25 mM HEPES, PH 7.5, 50 mM NaCl, 1 mM EDTA, 3 mM $MgCl_2$, 300 mM sucrose and 0.5% Triton X-100) for 1-5 min, followed by PBS rinse and fixation with 4% paraformaldehyde. They were washed 4× with PBS/0.1% Triton X-100, blocked with 5% normal goat serum and 2% bovine serum albumin (BSA) in PBS/0.1% Triton X-100. Primary antibodies (pSer$^{137}$-Pfn1 at 1:1000; pSer$^{784}$-VCP at 1:500; 53BP1 at 1:1000; γH2AX at 1:1000; BRCA1 at 1:1000; NBS1 at 1:500; pSer$^{1981}$-ATM at 1:1000 in the same blocking buffer were added and incubated at 4° C. overnight. Cells were washed 4× with PBS/0.1% Triton X-100, and incubated with Alexa 488 or 594-conjugated secondary antibodies in the same blocking buffer for 2 hr at room temperature. They were subsequently washed, counterstained with DAPI (1 μg/ml), and mounted using the ProLong Gold antifade reagent (Invitrogen). Fluorescent images were acquired on an inverted Olympus IX70 and an upright BX51 fluorescence microscopes using the CellSens software.

Immunoprecipitation: Cells (5-10×106) were harvested by scraping in PBS, and pelleted at 500 g for 5 min at 4° C. For native conditions, they were lysed by 200-500 μl ice-cold 1×RIPA buffer (CST, #9806) with added protease (Pierce, A32955) and phosphatase inhibitors (Pierce, A32957) or fractionated to obtain the nucleoplasm (see below for details). For denaturing conditions, they were suspended in ~50 μl pre-heated lysis buffer (1% SDS, 20 mM Tris-HCl, pH 7.4, 150 mM NaCl), heated at 95° C. for 10 min, and diluted 20-fold with ice cold buffer containing 20 mM Tris-HCl, pH 7.4, 150 mM NaCl, protease and phosphatase inhibitors. Samples under native or denatured conditions were clarified at >16,000 g at 4° C. for 10 min and supernatants were mixed with agarose pre-conjugated with various primary antibodies (10-20 μl agarose with 1-10 μg antibodies per sample) for 2-4 hr at 4° C. by gentle rotation. For sequential immunoprecipitations, supernatant from the first pulldown was collected by gently pelleting the beads (500 g, 5 min), and added to the second antibody. Beads were washed and samples were denatured in SDS sample buffer.

Mass spectrometry: The unknown ~100 kDa protein band induced by DNA damage and immunoprecipitated by the pSer$^{137}$-Pfn1 antibody was excised from silver-stained SDS gel and subjected to standard in-gel trypsin digest as previously described. Tryptic peptides were analyzed on a TripleTOF 5600 nano LC-MS system (AB SCIEX). Mass spectrometry data were searched against the Uniprot Human Reference Proteome using Mascot to identify proteins. Search parameters were 25 ppm mass tolerance (MS1), 0.1 dalton (MS2), 2 missed cleavages and trypsin/P protease specificity, fixed carbamidomethylation (Cys) and variable methionine oxidation and protein N-terminal acetylation.

Subcellular fractionation: Cells were scraped from tissue culture dishes after rinsing with PBS and centrifuged for 5 min at 500 g at 4° C., and subjected to fractionation using the protocol described by Mendez and Stillman, 2000. Briefly, cell pellets (2-5×10$^6$) were resuspended in 200 μl buffer A (10 mM HEPES, pH 7.9, 10 mM KCl, 1.5 mM $MgCl_2$, 0.34 M Sucrose, 10% Glycerol, 1 mM DTT, Protease and Phosphatase inhibitor cocktails), and Triton X-100 was added to a final concentration of 0.1%. After 8 min incubation on ice, samples were centrifuged at 1,300 g at 4° C. for 5 min, and supernatant was removed and saved as cytosolic fractions. Pellets were washed once with buffer A without Triton X-100 and centrifuged at 1,300 g again at 4° C. for 5 min. Supernatant was removed and discarded, and 100 μl buffer B (3 mM EDTA, 0.2 mM EGTA, 1 mM DTT, Protease and Phosphatase inhibitor cocktails) was used to resuspend the pellets. Samples were incubated on ice for 30 min with intermittent mixing, and centrifuged at 1,700 g at 4° C. for 5 min. Supernatant was removed and saved as the nucleoplasmic fraction. Pellets were washed once with buffer B and centrifuged again at 1,700 g at 4° C. for 5 min. Supernatant was discarded and pellets were solubilized in SDS sample buffer as the chromatin fraction.

Laser Microirradiation: A customized laser microirradiation system consisting of an inverted microscope (Nikon), a laser ablation unit (Photonic Instruments) and microscope automation and imaging software (Metamorph, Molecular Devices) was used. To introduce DNA damage to cells, a 551-nm dye laser was directed to irradiate cells cultured on 35-mm glass-bottomed dishes (MatTek Cultureware, P35G-15-14-C) in a line pattern. The laser energy delivered to each focused spot was set by an attenuator plate (50% transmission) and the number of pulses per spot. Cells were laser irradiated at the confluency of 50%, fixed, and immunofluorescence stained at different time points following irradiation as previously described (Chen et al., 2013, You et al., 2005). Total VCP and pSer784-VCP primary antibodies were used at 1:150, and NBS1 antibodies were used at 1:500. Cells were imaged using the Nikon microscope and MetaMorph software.

Comet assay: The experiment was performed using the kit for Single Cell Gel Electrophoresis Assay from Trevigen (cat #4250-050-K). In brief, cells were diluted to 1×105/ml in PBS, combined with pre-melt LMAgarose (at 37° C.) at a ratio of 1:10 (v/v) and immediately pipetted onto Comet-Slide (50 µl). Slides were placed flat at 4° C. in the dark for 30 min for sample adherence and subsequently immersed in 4° C. lysis solution (cat #4250-050-01) for 2 h. Excess lysis buffer was drained, and slides were immersed in freshly prepared alkaline unwinding solution, pH >13 (200 mM NaOH, 1 mM EDTA) for 20 min at RT. They were then subjected to gel electrophoresis using with the same alkaline electrophoresis solution at 21 V for 30 minutes. Slides were washed twice with dH2O and then 70% ethanol for 5 minutes. Samples were kept at 37° C. until the gel circle was completely melted and stained with 100 µL 1×SYBR® Gold (diluted in TE Buffer, pH 7.5 containing 10 mM Tris-HCl pH 7.5 and 1 mM EDTA) for 30 min at RT. Slides were completely dried at 37° C. Fluorescent images were taken using the Cellsens software on a 10× objective of an Olympus IX70 microscope and analyzed by ImageJ under the OpenComet plugin. Data were expressed by the tail DNA percentage (tail intensity out of total DNA intensity).

Colony formation assays: Cells were plated at low density (100-1000) in 24-well plates, allowed to adhere for several hours to overnight, and treated in triplicates with various drugs for overnight unless otherwise specified. They were washed twice with PBS and maintained in drug-free growth media for 10-14 days during which viable cells were periodically quantified using the Alamar blue assay. At the end of the experiments, cells were fixed by 4% paraformaldehyde and stained by 0.001% crystal violet followed by bright field image acquisition. Colonies were manually counted or semi-automatically quantified based on colony area.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All references, patents and patent applications disclosed herein are incorporated by reference with respect to the subject matter for which each is cited, which in some cases may encompass the entirety of the document.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," "less than or equal to," or "at most" precedes the first numerical value in a series of two or more numerical values, the term "no more than," "less than" or "less than or equal to," or "at most" applies to each of the numerical values in that series of numerical values. For example, less than or equal to 3, 2, or 1 is equivalent to less than or equal to 3, less than or equal to 2, or less than or equal to 1.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

What is claimed is:

1. An isolated antibody that specifically binds to the pSer$^{784}$ phosphorylation site of valosin-containing protein (pSer$^{784}$-VCP) wherein the antibody comprises: (a) a light chain variable region comprising a complementarity determining region 1 (CDR1) comprising the amino acid sequence set forth in SEQ ID NO:13; a CDR2 comprising the amino acid sequence set forth in SEQ ID NO: 14, and a CDR3 comprising the amino acid sequence set forth in SEQ ID NO: 15; and (b) a heavy chain variable region comprising a CDR1 comprising the amino acid sequence set forth in SEQ ID NO: 10, CDR2 comprising the amino acid sequence set forth in SEQ ID NO: 11, a CDR3 comprising the amino acid sequence set forth in SEQ ID NO: 12.

2. The isolated antibody of claim 1, wherein the antibody comprises the amino acid sequence set forth in SEQ ID NO: 16.

3. The isolated antibody of claim 1, wherein the antibody comprises the amino acid sequence set forth in SEQ ID NO: 17.

4. The isolated antibody of claim 1, wherein the antibody is encoded by a nucleic acid sequence comprising the sequence set forth in SEQ ID NO: 18 or SEQ ID NO:19.

5. The isolated antibody of claim 1, wherein the antibody is selected from a single-chain antibody, an antibody fragment, a chimeric antibody, and a humanized antibody.

6. An immunoassay comprising at least one isolated antibody of claim 1.

\* \* \* \* \*

SEQUENCE LISTING

```
<160> NUMBER OF SEQ ID NOS: 20

<210> SEQ ID NO 1
<211> LENGTH: 12
<212> TYPE: PRT
<213> ORGANISM: Artificial Sequence
<220> FEATURE:
<223> OTHER INFORMATION: Synthesized

<400> SEQUENCE: 1

Gly Gly Ala Gly Pro Ser Gln Gly Ser Gly Gly Gly
1               5                   10

<210> SEQ ID NO 2
<211> LENGTH: 28
<212> TYPE: DNA
<213> ORGANISM: Artificial Sequence
<220> FEATURE:
<223> OTHER INFORMATION: Synthesized

<400> SEQUENCE: 2
tggagctggc cccgctcagg gcagtgga                                          28

<210> SEQ ID NO 3
<211> LENGTH: 28
<212> TYPE: DNA
<213> ORGANISM: Artificial Sequence
<220> FEATURE:
<223> OTHER INFORMATION: Synthesized

<400> SEQUENCE: 3
tccactgccc tgagcgggc cagctcca                                           28

<210> SEQ ID NO 4
<211> LENGTH: 28
<212> TYPE: DNA
<213> ORGANISM: Artificial Sequence
<220> FEATURE:
<223> OTHER INFORMATION: Synthesized

<400> SEQUENCE: 4
tggagctggc cccgatcagg gcagtgga                                          28

<210> SEQ ID NO 5
<211> LENGTH: 28
<212> TYPE: DNA
<213> ORGANISM: Artificial Sequence
```

```
<220> FEATURE:
<223> OTHER INFORMATION: Synthesized

<400> SEQUENCE: 5
tccactgccc tgatcggggc cagctcca                                      28

<210> SEQ ID NO 6
<211> LENGTH: 21
<212> TYPE: DNA
<213> ORGANISM: Artificial Sequence
<220> FEATURE:
<223> OTHER INFORMATION: Synthesized

<400> SEQUENCE: 6
cctgatgtga agtacggcaa a                                             21

<210> SEQ ID NO 7
<211> LENGTH: 21
<212> TYPE: DNA
<213> ORGANISM: Artificial Sequence
<220> FEATURE:
<223> OTHER INFORMATION: Synthesized

<400> SEQUENCE: 7
agggaggtag atattggaat t                                             21

<210> SEQ ID NO 8
<211> LENGTH: 21
<212> TYPE: DNA
<213> ORGANISM: Artificial Sequence
<220> FEATURE:
<223> OTHER INFORMATION: Synthesized

<400> SEQUENCE: 8
ccagacgtca aatatggtaa g                                             21

<210> SEQ ID NO 9
<211> LENGTH: 21
<212> TYPE: DNA
<213> ORGANISM: Artificial Sequence
<220> FEATURE:
<223> OTHER INFORMATION: Synthesized

<400> SEQUENCE: 9
cgcgaagttg agataggaat t                                             21

<210> SEQ ID NO 10
<211> LENGTH: 5
<212> TYPE: PRT
<213> ORGANISM: Artificial Sequence
<220> FEATURE:
<223> OTHER INFORMATION: Synthesized

<400> SEQUENCE: 10

Asp Tyr Ala Met His
1               5

<210> SEQ ID NO 11
<211> LENGTH: 17
<212> TYPE: PRT
<213> ORGANISM: Artificial Sequence
<220> FEATURE:
<223> OTHER INFORMATION: Synthesized

<400> SEQUENCE: 11

Trp Thr Asn Thr Glu Thr Gly Glu Pro Thr Tyr Ala Asp Asp Phe Lys
```

-continued

```
1               5                   10                  15

Gly

<210> SEQ ID NO 12
<211> LENGTH: 6
<212> TYPE: PRT
<213> ORGANISM: Homo sapiens

<400> SEQUENCE: 12

Gly Trp Ser Phe Ala Tyr
1               5

<210> SEQ ID NO 13
<211> LENGTH: 16
<212> TYPE: PRT
<213> ORGANISM: Artificial Sequence
<220> FEATURE:
<223> OTHER INFORMATION: Synthesized

<400> SEQUENCE: 13

Lys Ser Ser Gln Ser Leu Leu Tyr Ser Asn Gly Lys Thr Tyr Leu Asn
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: Synthesized

<400> SEQUENCE: 14

Leu Val Ser Lys Leu Asp Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Synthesized

<400> SEQUENCE: 15

Val Gln Gly Thr His Phe Pro Arg Thr
1               5

<210> SEQ ID NO 16
<211> LENGTH: 115
<212> TYPE: PRT
<213> ORGANISM: Homo sapiens

<400> SEQUENCE: 16

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ala Met His Trp Val Lys Gln Ala Pro Gly Lys Gly Leu Lys Trp Met
        35                  40                  45

Gly Trp Thr Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95
```

Ala Arg Gly Trp Ser Phe Ala Tyr Trp Gly Gln Gly Thr Leu Val Thr
            100                 105                 110

Val Ser Ala
        115

<210> SEQ ID NO 17
<211> LENGTH: 112
<212> TYPE: PRT
<213> ORGANISM: Artificial Sequence
<220> FEATURE:
<223> OTHER INFORMATION: Synthesized

<400> SEQUENCE: 17

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Arg Thr Phe Gly Gly Gly Thr Lys Leu Glu Ile Lys
            100                 105                 110

<210> SEQ ID NO 18
<211> LENGTH: 345
<212> TYPE: DNA
<213> ORGANISM: Artificial Sequence
<220> FEATURE:
<223> OTHER INFORMATION: Synthesized

<400> SEQUENCE: 18
cagatccagt tggtgcagtc tggacctgag ctgaagaagc ctggagagac agtcaagatc     60
tcctgcaagg cctctggtta taccttcaca gactatgcaa tgcactgggt gaagcaggct    120
ccaggaaagg gtttaaagtg gatgggctgg acaaacactg agactggtga gccaacatat    180
gcagatgact tcaagggacg gtttgccttc tctttggaaa cctctgccag cactgcctat    240
ttgcagatca caaccctcaa aaatgaggac acggctacat atttctgtgc taggggctgg    300
tcgtttgctt actggggcca agggactctg gtgactgtct ctgca                    345

<210> SEQ ID NO 19
<211> LENGTH: 336
<212> TYPE: DNA
<213> ORGANISM: Artificial Sequence
<220> FEATURE:
<223> OTHER INFORMATION: Synthesized

<400> SEQUENCE: 19
gatgttgtga tgacccagac tccactcact ttgtcggtta ccattggaca accagcctct     60
atctcttgca agtcaagtca gagcctctta tatagtaatg gaaaaaccta tttgaattgg    120
ttattacaga ggccaggcca gtctccaaag cgcctaatct atctggtgtc taaactggac    180
tctggagtcc ctgacaggtt cactggcagt ggatcaggaa cagattttac actgaaaatc    240
agcagagtgg aggctgagga tttgggagtt tattactgcg tgcaaggtac acattttcct    300
cggacgttcg gtggaggcac caagctggaa atcaaa                                   336

<210> SEQ ID NO 20
<211> LENGTH: 806
<212> TYPE: PRT
<213> ORGANISM: Homo sapiens

<400> SEQUENCE: 20

Met Ala Ser Gly Ala Asp Ser Lys Gly Asp Asp Leu Ser Thr Ala Ile
1               5                   10                  15

Leu Lys Gln Lys Asn Arg Pro Asn Arg Leu Ile Val Asp Glu Ala Ile
            20                  25                  30

Asn Glu Asp Asn Ser Val Val Ser Leu Ser Gln Pro Lys Met Asp Glu
        35                  40                  45

Leu Gln Leu Phe Arg Gly Asp Thr Val Leu Leu Lys Gly Lys Lys Arg
    50                  55                  60

Arg Glu Ala Val Cys Ile Val Leu Ser Asp Asp Thr Cys Ser Asp Glu
65                  70                  75                  80

Lys Ile Arg Met Asn Arg Val Val Arg Asn Asn Leu Arg Val Arg Leu
                85                  90                  95

Gly Asp Val Ile Ser Ile Gln Pro Cys Pro Asp Val Lys Tyr Gly Lys
            100                 105                 110

Arg Ile His Val Leu Pro Ile Asp Asp Thr Val Glu Gly Ile Thr Gly
        115                 120                 125

Asn Leu Phe Glu Val Tyr Leu Lys Pro Tyr Phe Leu Glu Ala Tyr Arg
    130                 135                 140

Pro Ile Arg Lys Gly Asp Ile Phe Leu Val Arg Gly Gly Met Arg Ala
145                 150                 155                 160

Val Glu Phe Lys Val Val Glu Thr Asp Pro Ser Pro Tyr Cys Ile Val
                165                 170                 175

Ala Pro Asp Thr Val Ile His Cys Glu Gly Glu Pro Ile Lys Arg Glu
            180                 185                 190

Asp Glu Glu Glu Ser Leu Asn Glu Val Gly Tyr Asp Asp Ile Gly Gly
        195                 200                 205

Cys Arg Lys Gln Leu Ala Gln Ile Lys Glu Met Val Glu Leu Pro Leu
    210                 215                 220

Arg His Pro Ala Leu Phe Lys Ala Ile Gly Val Lys Pro Pro Arg Gly
225                 230                 235                 240

Ile Leu Leu Tyr Gly Pro Pro Gly Thr Gly Lys Thr Leu Ile Ala Arg
                245                 250                 255

Ala Val Ala Asn Glu Thr Gly Ala Phe Phe Phe Leu Ile Asn Gly Pro
            260                 265                 270

Glu Ile Met Ser Lys Leu Ala Gly Glu Ser Glu Ser Asn Leu Arg Lys
        275                 280                 285

Ala Phe Glu Glu Ala Glu Lys Asn Ala Pro Ala Ile Ile Phe Ile Asp
    290                 295                 300

Glu Leu Asp Ala Ile Ala Pro Lys Arg Glu Lys Thr His Gly Glu Val
305                 310                 315                 320

Glu Arg Arg Ile Val Ser Gln Leu Leu Thr Leu Met Asp Gly Leu Lys
                325                 330                 335

Gln Arg Ala His Val Ile Val Met Ala Ala Thr Asn Arg Pro Asn Ser
            340                 345                 350

Ile Asp Pro Ala Leu Arg Arg Phe Gly Arg Phe Asp Arg Glu Val Asp
    355                 360                 365

```
Ile Gly Ile Pro Asp Ala Thr Gly Arg Leu Glu Ile Leu Gln Ile His
    370                 375                 380

Thr Lys Asn Met Lys Leu Ala Asp Asp Val Asp Leu Glu Gln Val Ala
385                 390                 395                 400

Asn Glu Thr His Gly His Val Gly Ala Asp Leu Ala Ala Leu Cys Ser
                405                 410                 415

Glu Ala Ala Leu Gln Ala Ile Arg Lys Lys Met Asp Leu Ile Asp Leu
                420                 425                 430

Glu Asp Glu Thr Ile Asp Ala Glu Val Met Asn Ser Leu Ala Val Thr
            435                 440                 445

Met Asp Asp Phe Arg Trp Ala Leu Ser Gln Ser Asn Pro Ser Ala Leu
450                 455                 460

Arg Glu Thr Val Val Glu Val Pro Gln Val Thr Trp Glu Asp Ile Gly
465                 470                 475                 480

Gly Leu Glu Asp Val Lys Arg Glu Leu Gln Glu Leu Val Gln Tyr Pro
                485                 490                 495

Val Glu His Pro Asp Lys Phe Leu Lys Phe Gly Met Thr Pro Ser Lys
            500                 505                 510

Gly Val Leu Phe Tyr Gly Pro Pro Gly Cys Gly Lys Thr Leu Leu Ala
            515                 520                 525

Lys Ala Ile Ala Asn Glu Cys Gln Ala Asn Phe Ile Ser Ile Lys Gly
    530                 535                 540

Pro Glu Leu Leu Thr Met Trp Phe Gly Glu Ser Glu Ala Asn Val Arg
545                 550                 555                 560

Glu Ile Phe Asp Lys Ala Arg Gln Ala Ala Pro Cys Val Leu Phe Phe
                565                 570                 575

Asp Glu Leu Asp Ser Ile Ala Lys Ala Arg Gly Gly Asn Ile Gly Asp
            580                 585                 590

Gly Gly Gly Ala Ala Asp Arg Val Ile Asn Gln Ile Leu Thr Glu Met
            595                 600                 605

Asp Gly Met Ser Thr Lys Lys Asn Val Phe Ile Ile Gly Ala Thr Asn
610                 615                 620

Arg Pro Asp Ile Ile Asp Pro Ala Ile Leu Arg Pro Gly Arg Leu Asp
625                 630                 635                 640

Gln Leu Ile Tyr Ile Pro Leu Pro Asp Glu Lys Ser Arg Val Ala Ile
                645                 650                 655

Leu Lys Ala Asn Leu Arg Lys Ser Pro Val Ala Lys Asp Val Asp Leu
            660                 665                 670

Glu Phe Leu Ala Lys Met Thr Asn Gly Phe Ser Gly Ala Asp Leu Thr
            675                 680                 685

Glu Ile Cys Gln Arg Ala Cys Lys Leu Ala Ile Arg Glu Ser Ile Glu
    690                 695                 700

Ser Glu Ile Arg Arg Glu Arg Glu Arg Gln Thr Asn Pro Ser Ala Met
705                 710                 715                 720

Glu Val Glu Glu Asp Pro Val Pro Glu Ile Arg Arg Asp His Phe
                725                 730                 735

Glu Glu Ala Met Arg Phe Ala Arg Arg Ser Val Ser Asp Asn Asp Ile
            740                 745                 750

Arg Lys Tyr Glu Met Phe Ala Gln Thr Leu Gln Gln Ser Arg Gly Phe
            755                 760                 765

Gly Ser Phe Arg Phe Pro Ser Gly Asn Gln Gly Gly Ala Gly Pro Ser
    770                 775                 780
```

```
Gln Gly Ser Gly Gly Gly Thr Gly Gly Ser Val Tyr Thr Glu Asp Asn
785                 790                 795                 800

Asp Asp Asp Leu Tyr Gly
                805
```